(12) United States Patent
Luo et al.

(10) Patent No.: US 9,429,581 B2
(45) Date of Patent: Aug. 30, 2016

(54) IP-10 ANTIBODY DOSAGE ESCALATION REGIMENS

(71) Applicant: BRISTOL-MYERS SQUIBB COMPANY, Princeton, NJ (US)

(72) Inventors: Allison Y. Luo, East Hanover, NJ (US); Wendy L. Trigona, Newtown, PA (US); Jinshan Shen, Skillman, NJ (US); Li-An Xu, Branchburg, NJ (US); Yan Zhang, Princeton, NJ (US); Bruce Stouffer, Branchburg, NJ (US); Haibin Chen, San Jose, CA (US); Haichun Huang, Fremont, CA (US); Xiaolu Tao, Hopewell, NJ (US); Catherine Brockus, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1 day.

(21) Appl. No.: 14/055,238

(22) Filed: Oct. 16, 2013

(65) Prior Publication Data
US 2014/0127229 A1    May 8, 2014

Related U.S. Application Data

(63) Continuation-in-part of application No. PCT/US2012/035457, filed on Apr. 27, 2012.

(60) Provisional application No. 61/480,938, filed on Apr. 29, 2011, provisional application No. 61/714,402, filed on Oct. 16, 2012.

(51) Int. Cl.
| | |
|---|---|
| *G01N 33/68* | (2006.01) |
| *C07K 16/24* | (2006.01) |
| *C07K 16/42* | (2006.01) |
| *A61K 39/395* | (2006.01) |
| *A61K 39/00* | (2006.01) |

(52) U.S. Cl.
CPC ........ *G01N 33/686* (2013.01); *A61K 39/3955* (2013.01); *C07K 16/24* (2013.01); *C07K 16/4208* (2013.01); *A61K 2039/505* (2013.01); *C07K 2317/21* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| | | |
|---|---|---|
| 6,652,854 B2 | 11/2003 | Mohler et al. |
| 7,084,260 B1 | 8/2006 | Lonberg et al. |
| 7,786,268 B2 | 8/2010 | Fischer et al. |
| 7,935,793 B2 | 5/2011 | Balasa et al. |
| 7,964,194 B2 | 6/2011 | Lillard, Jr. et al. |
| 8,258,266 B2 | 9/2012 | Deshpande et al. |
| 2003/0166589 A1 | 9/2003 | Karin |
| 2005/0191293 A1 | 9/2005 | Deshpande et al. |
| 2014/0065164 A1 | 3/2014 | Luo et al. |

FOREIGN PATENT DOCUMENTS

| | | |
|---|---|---|
| WO | WO 01/09187 | 2/2001 |
| WO | WO 02/15932 | 2/2002 |
| WO | WO 2004/101511 | 11/2004 |
| WO | WO 2005/058815 | 6/2005 |
| WO | WO 2012/149320 | 11/2012 |

OTHER PUBLICATIONS

Pan et al, FASEB J. Jan. 1995;9(1):43-9.*
Vajdos et al. (J Mol Biol. Jul. 5, 2002;320(2):415-28 at 416).*
Brown et al. (J Immunol. May 1996;156(9):3285-91.*
Kuhne, Michelle et al., "MDX-1100, a fully human anti-CSCL10 (IP-10) antibody, is a high affinity, neutralizing antibody that entered Phase 1 clinical trials for the treatment of Ulcerative Colitis (UC)," The Journal of Immunology, vol. 178:131.20 (2007).
Mayer, Lloyd et al., "Anti-IP-10 antibody (BMS-936557) for ulcerative colitis: a phase II randomised study," Gut, pp. 1-9, doi:10.1136/gutjnl-2012-303424 (2013).
Medarex Inc., "Medarex Announces Primary Endpoint Achieved in MDX-1100 Anti-IP-10 Antibody Phase 2 Trial for Rheumatoid Arthritis," retrieved online at: http://www.medicalnewstoday.com/releases/150119.php, 3 pages (2009).
Brown, McKay et al., "Tolerance to Single, but Not Multiple, Amino Acid Replacements in Antibody VH CDR2," The Journal of Immunology. vol. 156:3285-3291 (1996).
Carr, Daniel J.J. et al., "Effect of Anti-CXCL10 Monoclonal Antibody on Herpes Simplex Virus Type 1 Keratitis and Retinal Infection," Journal of Virology, vol. 77(18):10037-10046 (2003).
Carr, D.J. et al., "Neutralizing Antibody to the Chemokine CXCL10 Reduces Ocular Inflammation and Delays Viral Spread Following Cornea HSV-1 Infection," Invest. Ophthalmol., Abstract No. 4183 (2003).

(Continued)

*Primary Examiner* — Brian J Gangle
*Assistant Examiner* — Andrea McCollum
(74) *Attorney, Agent, or Firm* — Z. Angela Guo

(57) ABSTRACT

In certain embodiments, the present invention provides a method of treating an Interferon gamma inducible protein 10 (IP-10)-related disease in a subject, comprising: (a) administering to the subject a predetermined dosage of an anti-IP-10 antibody; (b) detecting the level of the anti-IP-10 antibody in a sample of the subject; and (c) if the level of the anti-IP-10 antibody from step (b) is below a threshold exposure level, increasing the dosage of the anti-IP-10 antibody in the subject such that the IP-10 related disease in the subject is treated. In certain embodiments, the present invention provides an isolated monoclonal anti-idiotypic antibody, or an antigen binding portion thereof, which binds to the anti-IP-10 antibody MDX-1100.

13 Claims, 18 Drawing Sheets

(56) References Cited

OTHER PUBLICATIONS

Fishwild, Dianne M. et al., "High-avidity human IgGk monoclonal antibodies from a novel strain of minilocus transgenic mice," Nature Biotechnology, vol. 14:845-851 (1996).
Foung, S.K., et al. "Generation of human monoclonal antibodies by fusion of EBV-activated B cells to a human-mouse hybridoma," Methods Enzymol. vol. 121:168-174 (1986).
GenCore, Sequence alignment, "US-12-472-877-121," pp. 1-4 (2011).
Klein, Robyn S. et al., "IFN-inducible Protein 10/CXC Chemokine Ligand 10-Independent Induction of Experimental Autoimmune Encephalomyelitis," The Journal of Immunology, vol. 172:550-559 (2004).
Kolb, et al., "Identification of a T cell chemotactic factor in the cerebrospinal fluid of HIV-1-infected individuals as interferon-g inducible protein 10," Journal of Neuroimmunology, vol. 93:172-188 (1999).
Kraan, M.C., et al. "The development of clinical signs of rheumatoid synovial inflammation is associated with increased synthesis of the chemokine CXCL8 (interleukin-8)." Arthritis Res., vol. 3(1):65-71 (2001).
Liu, Michael T. et al., "Neutralization of the Chemokine CXCL10 Reduces Inflammatory Cell Invasion and Demyelination and Improves Neurological Function in a Viral Model of Multiple Sclerosis," The Journal of Immunology, vol. 167:4091-4097 (2001).
Marks. James D. et al., "By-passing Immunization: Building High Affinity Human Antibodies by Chain Shuffling," Nature Biotechnology, vol. 10:779-783 (1992).
Pandya; Deepal, "Generation of a high affinity humanized anti-IP-10 monoclonal antibody by protein engineering," The Midwinter Conference of Immunologists, Poster Abstract (2005).
Patel, D.D., et al., "CXCR3 and CCR5 ligands in rheumatoid arthritis synovium," Clin. Immunol, vol. 98(1):39-45 (2001).
Rader Christoph et al., "A phage display approach for rapid antibody humanization: Designed combinatorial V gene libraries," Proc. Natl. Acad. Sci. USA, vol. 95:8910-8915 (1998).
Reff, et al., "A review of modifications to recombinant antibodies: attempt to increase efficacy in oncology applications," Critical Reviews in Oncology/Hematology, vol. 40:25-35 (2001).
Rudikoff, Stuart et al., "Single amino acid substitution altering antigen-binding specificity," Proc. Natl. Acad. Sci. USA, vol. 79:1979-1983 (1982).
Ruschpler, P., et al., "High CXCR3 expression in synovial mast cells associated with CXCL9 and CXCL10 expression in inflammatory synovial tissues of patients with rheumatoid arthritis," Arthritis Res. Ther., vol. 5(5):R241-R252 (2003).
Salomon, I., et al., "Targeting the Function of IFN-g-Inducible Protein 10 Suppresses Ongoing Adjuvant Arthritis;" The Journal of Immunology, vol. 169:2685-2693 (2002).
Söderlind, Eskil et al., "Complementarity-determining region (CDR) implantation: a theme of recombination," Immunotechnology, vol. 4:279-285 (1999).
Swaminathan, G. Jawahar et al., "Crystal Structures of Oligomeric Forms of the IP-10/CXCL10 Chemokine," Structure, vol. 11:521-532 (2003).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Supplementary European Search Report for Application No. 04813771.5, 4 pages, dated Jan. 13, 2009.
European Office Action for Application No. 11166104.7, 11 pages, dated Sep. 30, 2011.
International Search Report for Application No. PCT/US04/29373, 2 pages, dated Apr. 7, 2005.
International Search Report for Application No. PCT/US04/41506, 4 pages, dated Dec. 15, 2005.
Written Opinion for Application No. PCT/US04/29373, 3 pages, dated Apr. 7, 2005.
Mayer, Lloyd et al., "A Randomized, Placebo-Controlled Trial of MDX-1100, an Anti-IP-10 Antibody, for Moderately to Severely Active Ulcerative Colitis," Gastroenterology, vol. 139, No. 1, (2010), pp. e17-e18; presented at Digestive Disease Week® in New Orleans, Louisiana, May 1-6, 2010.
Pan, Ying et al., "Anti-idiotypic antibodies: biological function and structural studies," FASEB Journal, Federation of American Societies for Experimental Biology, US, vol. 9, No. 1 (Jan. 1, 1995), pp. 43-49.
Tabrizi, Mohammad et al., "Application of Quantitative Pharmacology in Development of Therapeutic Monoclonal Antibodies," AAPS Journal, vol. 12, No. 4 (Dec. 2010), pp. 592-601.
Yellin, Michael et al., "A Phase II, Randomized, Double-Blind, Placebo-Controlled Study Evaluating the Efficacy and Safety of MDX-1100, a Fully Human Anti-CXCL10 Monoclonal Antibody, in Combination with Methotrexate in Patients with Rheumatoid Arthritis," Arthritis & Rheumatism, vol. 64, No. 6 (Jun. 2012), pp. 1730-1739.
Singh, Udai P. et al. Inhibition of IFN-γ-Inducible Protein-10 Abrogates Colitis in IL-10—Mice, J Immunol. 2003; 171:1401-1406.
Sasaki, Shunya, et al., "Blockade of CXCL10 protects mice from acute colitis and enhances crypt cell survival," Eur. J. Immunol. 2002; 32: 3197-3205.
Hardi, Robert et al. "A Phase 1 Open-Label, Single-Dose, Dose-Escalation Study of Mdx-1100, a High-Affinity, Neutralizing, Fully Human Igg1k Anti-CXCL10 (Ip10) Monoclonal Antibody, in Ulcerative Colitis," Gastroenterology vol. 134 issue 4 Apr. 2008. p. A-99-A-100 DOI: 10.1016/S0016-5085(08)60466-7. ISSN: 0016-5085.
Yellin, Michael et al. "A Double-Blind, Placebo-Controlled, Dose-Escalation, Safety and Pharmacokinetic Study of MDX-1100, a Fully Human Anti-CXCL10 Monoclonal Antibody, in Healthy Subjects," M. *Gastroenterology* vol. 134 issue 4 Apr. 2008. p. A-493-A-494 DOI: 10.1016/S0016-5085(08)62304-5. ISSN: 0016-5085.
Witte, Alison et al. "CXCL10 Expression and Biological Activities in Inflammatory Bowel Disease." *Gastroenterology* vol. 134 issue 4 Apr. 2008. p. A-648 DOI: 10.1016/S0016-5085(08)63023-1. ISSN: 0016-5085.
Lichtenstein, Gary R., "Selected Summaries," Gastroenterology, vol. 139, pp. 344-355 (2010).
European Office Action received Dec. 23, 2015.

* cited by examiner

E-R Relationship of Clinical Response, Clinical Remission and Mucosal Healing Rates
Stratified by Cminss of BMS-936557 at Study Day 57

Logistic Regression Analysis of Clinical Response Rate vs Cminss of BMS-936557 at Study Day 57

Logistic Regression Analysis of Clinical Remission Rate vs Cminss of
BMS-936557 at Study Day 57

Note: This result is from a post-hoc analysis with re-derived Mayo score after unblinding the data.
Mayo Score was re-deriverd by following conventional rules in the literature.

Logistic Regression Analysis of Mucosal Healing Rate vs Cminss of BMS-936557 at Study Day 57

Note: This result is from a post-hoc analysis with re-derived Mayo score after unblinding the data.
Mayo Score was re-deriverd by following conventional rules in the literature.

The Negative Log10 Transformed P-Values vs. Different Cminss as Possible Target Exposure Binding Analysis of Clone 10C8 and 6C9

Binding Analysis of Clone 2F5 and 23H10

Binding Analysis of Subclone of 10C8

Binding Analysis of Subclones of 6C9, 2F5 and 23H10

Binding Analysis of Clone 10C8 Competition with IP10

Binding Analysis of Clone 2F5 and 23H10 Competition with IP10

FIG. 12A

Anti-IP10 6A5 VH

V segment:    3-33
D segment:    3-10
J segment:    JH6b

```
          Q   M   Q   L   V   E   S   G   G   G   V   V   Q   P   G   R   S   L
  1      CAA ATG CAG CTG GTG GAG TCT GGG GGA GGC GTG GTC CAG CCT GGG AGG TCC CTG

CDR1
                                                    ----------------------------
          R   L   S   C   T   A   S   G   F   T   F   S   N   N   G   M   H   W
 55      AGA CTC TCC TGT ACA GCG TCT GGA TTC ACC TTC AGT AAC AAT GGC ATG CAC TGG

CDR2
                                                                  --------------
          V   R   Q   A   P   G   K   G   L   E   W   V   A   V   I   W   F   D
109      GTC CGC CAG GCT CCA GGC AAG GGG CTG GAG TGG GTG GCA GTT ATA TGG TTT GAT

CDR2
         ----------------------------------------------------
          G   M   N   K   F   Y   V   D   S   V   K   G   R   F   T   I   S   R
163      GGA ATG AAT AAA TTC TAT GTA GAC TCC GTG AAG GGC CGA TTC ACC ATC TCC AGA

D   N   S   K   N   T   L   Y   L   E   M   N   S   L   R   A   E   D
217      GAC AAT TCC AAG AAC ACG CTG TAT CTG GAA ATG AAC AGC CTG AGA GCC GAG GAC

CDR3
                                                          ----------------------
          T   A   I   Y   Y   C   A   R   E   G   D   G   S   G   I   Y   Y   Y
271      ACG GCT ATA TAT TAC TGT GCG AGA GAA GGG GAT GGT TCG GGG ATT TAT TAC TAC

CDR3
         ----------------------
          Y   G   M   D   V   W   G   Q   G   T   T   V   T   V   S   S
325      TAC GGT ATG GAC GTC TGG GGC CAA GGG ACC ACG GTC ACC GTC TCC TCA
```

FIG. 12B

Anti-IP10 6A5 VK

V segment: A27
J segment: JK3

```
        E   I   V   L   T   Q   S   P   G   T   L   S   L   S   P   G   E   R
1       GAA ATT GTG TTG ACG CAG TCT CCA GGC ACC CTG TCT TTG TCT CCA GGG GAA AGA
                                            CDR1
                                            ~~~~~~~~~~~~~~~~~~~~~~~~~~~~~~~~~~~~
        A   T   L   S   C   R   A   S   Q   S   V   S   S   Y   L   A   W
55      GCC ACC CTC TCC TGC AGG GCC AGT CAG AGT GTT AGC AGC AGC TAT TTA GCC TGG
                                                                        CDR2
                                                                        ~~~~~~~~~~~~~~~~
        Y   Q   Q   K   P   G   Q   A   P   R   L   L   I   Y   G   A   S   S
109     TAC CAG CAG AAA CCT GGC CAG GCT CCC AGG CTC CTC ATC TAT GGT GCA TCC AGC
            CDR2
            ~~~~~~~~~~~~~~~~
        R   A   T   G   I   P   D   R   F   S   G   S   G   S   G   T   D   F
163     AGG GCC ACT GGC ATC CCA GAC AGG TTC AGT GGC AGT GGG TCT GGG ACA GAC TTC
                                                                            CDR 3
                                                                            ~~~~
        T   L   T   I   S   R   L   E   P   E   D   F   A   V   Y   Y   C   Q
217     ACT CTC ACC ATC AGC AGA CTG GAG CCT GAA GAT TTT GCA GTG TAT TAC TGT CAG
            CDR3
            ~~~~~~~~~~~~~~~~~~~~~~
        Q   Y   G   S   S   P   I   F   T   F   G   P   G   T   K   V   D   I
271     CAG TAT GGT AGC TCA CCT ATA TTC ACT TTC GGC CCT GGG ACC AAA GTG GAT ATC

K
325     AAA
```

```
          E    V    K    L    L    E    S    G    G    G    L    V    Q    P    G    G    S
1         GAG  GTG  AAG  CTT  CTC  GAG  TCT  GGA  GGT  GGC  CTG  GTG  CAG  CCT  GGA  GGA  TCC

_____CDR1_____
          L    K    L    S    C    A    A    S    G    F    D    F    S    R    Y    W    M
52        CTG  AAA  CTC  TCC  TGT  GCA  GCC  TCA  GGA  TTC  GAT  TTT  AGT  AGA  TAC  TGG  ATG

____                                                              ____CDR2_____
          I    W    V    R    Q    A    P    G    K    G    L    E    W    I    G    E    I
103       ATT  TGG  GTC  CGG  CAG  GCT  CCA  GGG  AAA  GGG  CTA  GAA  TGG  ATT  GGA  GAA  ATT

_____
          N    P    D    S    S    T    I    N    Y    T    P    S    L    K    D    K    F
154       AAT  CCA  GAT  AGC  AGT  ACG  ATA  AAC  TAT  ACG  CCA  TCT  CTA  AAG  GAT  AAA  TTC

I    I    S    R    D    N    A    K    N    T    L    Y    L    Q    M    S    K
205       ATC  ATC  TCC  AGA  GAC  AAC  GCC  AAA  AAT  ACG  CTG  TAC  CTG  CAA  ATG  AGC  AAA

_____CDR3_____
          V    R    S    E    D    T    A    L    Y    Y    C    A    R    P    L    Y    G
256       GTG  AGA  TCT  GAG  GAC  ACA  GCC  CTT  TAT  TAC  TGT  GCA  AGA  CCC  CTC  TAC  GGC

_____
          Y    G    F    A    Y    W    G    Q    G    T    L    V    T    V    S    A
307       TAC  GGG  TTT  GCT  TAC  TGG  GGC  CAA  GGG  ACT  CTG  GTC  ACT  GTC  TCT  GCA
```

```
          D    I    V    M    T    Q    S    H    K    F    M    S    T    S    V    G    D
1         GAC  ATT  GTG  ATG  ACC  CAG  TCT  CAC  AAA  TTC  ATG  TCC  ACA  TCA  GTA  GGA  GAC

_____CDR1_____
          R    V    S    I    T    C    K    A    S    Q    D    V    S    T    A    V    A
52        AGG  GTC  AGC  ATC  ACC  TGC  AAG  GCC  AGT  CAG  GAT  GTG  AGT  ACT  GCT  GTA  GCC

____CDR2____
          W    Y    Q    Q    K    P    G    Q    S    P    K    L    L    I    F    S    A
103       TGG  TAT  CAA  CAG  AAA  CCA  GGA  CAA  TCT  CCT  AAA  CTA  CTG  ATT  TTC  TCG  GCA

_____
          S    Y    R    Y    T    G    V    P    D    R    F    T    G    S    G    S    G
154       TCC  TAC  CGG  TAC  ACT  GGA  GTC  CCT  GAT  CGC  TTC  ACT  GGC  AGT  GGA  TCT  GGG

T    D    F    T    F    T    I    S    S    V    Q    A    E    D    L    A    V
205       ACG  GAT  TTC  ACT  TTC  ACC  ATC  AGC  AGT  GTG  CAG  GCT  GAA  GAC  CTG  GCA  GTT

_____CDR3_____
          Y    Y    C    Q    Q    H    Y    S    T    P    R    T    F    G    G    G    T
256       TAT  TAC  TGT  CAG  CAA  CAT  TAT  AGT  ACT  CCT  CGG  ACG  TTC  GGT  GGA  GGC  ACC

K    V    E    I    K
307       AAG  GTG  GAA  ATC  AAA
```

```
        Q   I   Q   L   V   Q   S   G   P   E   L   K   K   P   G   E   T
1       CAG ATC CAG TTG GTG CAG TCT GGA CCT GAG CTG AAG AAG CCT GGA GAG ACA

CDR1
        V   K   I   S   C   K   A   S   G   Y   T   F   T   N   Y   G   M
52      GTC AAG ATC TCC TGC AAG GCT TCT GGG TAT ACC TTC ACA AAC TAT GGA ATG

CDR2
        N   W   V   K   Q   A   P   G   K   G   L   K   W   M   G   W   I
103     AAC TGG GTG AAG CAG GCT CCA GGA AAG GGT TTA AAG TGG ATG GGC TGG ATA

N   T   Y   T   G   E   P   T   Y   A   D   D   F   K   G   R   F
154     AAC ACC TAC ACT GGA GAG CCA ACA TAT GCT GAT GAC TTC AAG GGA CGG TTT

A   F   S   L   E   T   S   A   S   T   A   Y   L   Q   I   N   N
205     GCC TTC TCT TTG GAA ACC TCT GCC AGC ACT GCC TAT TTG CAG ATC AAC AAC

CDR3
        L   K   N   E   D   T   A   T   Y   F   C   A   K   D   G   T   G
256     CTC AAA AAT GAG GAC ACG GCT ACA TAT TTC TGT GCA AAG GAC GGG ACG GGT

A   M   D   Y   W   G   Q   G   T   S   V   T   V   S   S
307     GCT ATG GAC TAC TGG GGT CAA GGA ACC TCA GTC ACC GTC TCC TCA
```

```
        D   I   V   M   T   Q   S   P   A   T   L   S   V   T   P   G   D
1       GAC ATT GTG ATG ACT CAG TCT CCA GCC ACC CTG TCT GTG ACT CCA GGA GAT

CDR1
        R   V   S   L   S   C   R   A   S   Q   S   I   S   D   Y   L   H
52      AGA GTC TCT CTT TCC TGC AGG GCC AGC CAG AGT ATT AGC GAC TAC TTA CAC

CDR2
        W   Y   Q   Q   K   S   H   E   S   P   R   L   L   I   K   Y   A
103     TGG TAT CAA CAA AAA TCA CAT GAG TCT CCA AGG CTT CTC ATC AAA TAT GCT

S   Q   S   I   S   G   I   P   S   R   F   S   G   S   G   S   G
154     TCC CAA TCC ATC TCT GGG ATC CCC TCC AGG TTC AGT GGC AGT GGA TCA GGG

S   D   F   T   L   S   I   N   S   V   E   P   E   D   V   G   V
205     TCA GAT TTC ACT CTC AGT ATC AAC AGT GTG GAA CCT GAA GAT GTT GGA GTG

CDR3
        Y   Y   C   Q   N   G   H   S   F   P   Y   T   F   G   G   G   T
256     TAT TAC TGT CAA AAT GGT CAC AGC TTT CCG TAC ACG TTC GGA GGG GGG ACC

K   L   E   I   K
307     AAG CTG GAA ATA AAA
```

```
        Q   I   Q   L   V   Q   S   G   P   E   L   K   K   P   G   E   T
1       CAG ATC CAG TTG GTG CAG TCT GGA CCT GAG CTG AAG AAG CCT GGA GAG ACA

_CDR1_____
        V   K   I   S   C   K   A   S   G   Y   T   F   T   N   Y   G   M
52      GTC AAG ATC TCC TGC AAG GCT TCT GGG TAT ACC TTC ACA AAT TAT GGA ATG

___                                                 _CDR2____
        N   W   V   K   Q   A   P   G   K   G   L   K   W   M   G   W   I
103     AAC TGG GTG AAG CAG GCT CCA GGA AAG GGT TTA AAG TGG ATG GGC TGG ATA

_____
        N   T   Y   T   G   E   S   A   Y   A   D   D   F   K   G   R   F
154     AAC ACC TAC ACT GGA GAG TCA GCA TAT GCT GAT GAC TTC AAG GGA CGG TTT

A   F   S   L   E   T   S   A   S   T   A   Y   L   Q   I   N   N
205     GCC TTC TCC TTG GAA ACC TCT GCC AGC ACT GCC TAT TTG CAG ATC AAC AAC

_CDR3_____
        L   K   N   E   D   T   A   T   Y   F   C   A   T   G   G   Y   Y
256     CTC AAA AAT GAG GAC ACG GCT ACA TAT TTC TGT GCA ACC GGG GGT TAC TAT

_____
        G   M   D   Y   W   G   Q   G   T   S   V   T   V   S   S
307     GGT ATG GAC TAC TGG GGT CAA GGA ACC TCA GTC ACC GTC TCC TCA
```

```
        D   I   V   M   T   Q   S   P   A   T   L   S   V   T   P   G   D
1       GAC ATT GTG ATG ACT CAG TCT CCA GCC ACC CTG TCT GTG ACT CCA GGA GAT

_CDR1_____
        R   V   S   L   S   C   R   A   S   Q   S   I   S   D   Y   L   H
52      AGA GTC TCT CTT TCC TGC AGG GCC AGC CAG AGT ATT AGC GAC TAC TTA CAC

_CDR2____
        W   Y   Q   Q   K   S   H   E   S   P   R   L   L   I   K   Y   A
103     TGG TAT CAA CAA AAA TCA CAT GAG TCT CCA AGG CTT CTC ATC AAA TAT GCT

_____
        S   Q   S   I   S   G   I   P   S   R   F   S   G   S   G   S   G
154     TCC CAA TCC ATC TCT GGG ATC CCC TCC AGG TTC AGT GGC AGT GGA TCA GGG

S   D   F   T   L   S   I   N   S   V   E   P   E   D   V   G   V
205     TCA GAT TTC ACT CTC AGT ATC AAC AGT GTG GAA CCT GAA GAT GTT GGA GTG

_CDR3_____
        Y   Y   C   Q   N   G   H   S   F   P   L   T   F   G   A   G   T
256     TAT TAC TGT CAA AAT GGT CAC AGC TTT CCG CTC ACG TTC GGT GCT GGG ACC

K   L   E   L   K
307     AAG CTG GAG CTG AAA
```

```
        Q   I   Q   L   V   Q   S   G   P   E   L   K   K   P   G   E   T
1       CAG ATC CAG TTG GTG CAG TCT GGA CCT GAG CTG AAG AAG CCT GGA GAG ACA

_CDR1_____
        V   K   I   S   C   K   A   S   G   F   T   F   T   N   Y   G   M
52      GTC AAG ATC TCC TGC AAG GCT TCT GGG TTT ACC TTC ACA AAC TAT GGA ATG

_                                                   _CDR2____
        N   W   V   K   Q   A   P   G   K   G   L   K   W   M   G   W   I
103     AAC TGG GTG AAG CAG GCT CCA GGA AAG GGT TTA AAG TGG ATG GGC TGG ATA

_____
        N   T   Y   T   G   E   P   T   Y   A   D   D   F   K   G   R   F
154     AAC ACC TAC ACT GGA GAG CCA ACA TAT GCT GAT GAC TTC AAG GGA CGG TTT

A   F   S   L   E   T   S   A   S   T   A   Y   L   Q   I   N   N
205     GCC TTC TCT TTG GAA ACC TCT GCC AGC ACT GCC TAT TTG CAG ATC AAC AAC

_CDR3_____
        L   K   N   E   D   T   A   T   Y   F   C   A   T   G   G   Y   Y
256     CTC AAA AAT GAG GAC ACG GCT ACA TAT TTC TGT GCA ACG GGG GGT TAC TAT

_____
        G   M   D   Y   W   G   Q   G   T   S   V   T   V   S   S
307     GGT ATG GAC TAC TGG GGT CAA GGA ACC TCA GTC ACC GTC TCC TCA
```

```
        D   I   V   M   T   Q   S   P   A   T   L   S   V   T   P   G   D
1       GAC ATT GTG ATG ACT CAG TCT CCA GCC ACC CTG TCT GTG ACT CCA GGA GAT

_CDR1_____
        R   V   S   L   S   C   R   A   S   Q   S   I   S   D   Y   L   H
52      AGA GTC TCT CTT TCC TGC AGG GCC AGC CAG AGT ATT AGC GAC TAC TTA CAC

_CDR2____
        W   Y   Q   Q   K   S   H   E   S   P   R   L   L   I   K   Y   A
103     TGG TAT CAA CAA AAA TCA CAT GAG TCT CCA AGG CTT CTC ATC AAA TAT GCT

_____
        S   Q   S   I   S   G   I   P   S   R   F   S   G   S   G   S   G
154     TCC CAA TCC ATC TCT GGG ATC CCC TCC AGG TTC AGT GGC AGT GGA TCA GGG

S   D   F   T   L   S   I   N   S   V   E   P   E   D   V   G   V
205     TCA GAT TTC ACT CTC AGT ATC AAC AGT GTG GAA CCT GAA GAC GTT GGA GTG

_CDR3_____
        Y   Y   C   Q   N   G   H   S   F   P   L   T   F   G   A   G   T
256     TAT TAC TGT CAA AAT GGT CAC AGC TTT CCG CTC ACG TTC GGT GCT GGG ACC

K   L   E   V   K
307     AAG CTG GAG GTG AAA
```

IP-10 ANTIBODY DOSAGE ESCALATION REGIMENS

CROSS-REFERENCE TO RELATED APPLICATIONS

This application is a continuation-in-part of International Application No. PCT/US2012/035457, filed Apr. 27, 2012, which claims priority to U.S. Provisional Application Ser. No. 61/480,938, filed Apr. 29, 2011, and also claims priority to U.S. Provisional Application Ser. No. 61/714,402, filed Oct. 16, 2012, the entire contents of all of which are herein incorporated by reference.

BACKGROUND OF THE INVENTION

Interferon gamma inducible protein 10 (IP-10) (also known as CXCL10) is a 10 kDa chemokine that is secreted by a variety of cells, including endothelial cells, monocytes, fibroblasts, and keratinocytes, in response to IFN-gamma. IP-10 is also present in dermal macrophages and endothelial cells in delayed type hypersensitivity (DTH) responses in human. Although originally identified based on its being induced by IFN-gamma, IP-10 can also be induced by IFN-alpha, for example in dendritic cells. IP-10 expression can also be induced in cells of the central nervous system, such as astrocytes and microglia, by stimuli such as IFN-gamma, viruses and lipopolysaccharide.

The receptor for IP-10 has been identified as CXCR3, a seven transmembrane receptor. CXCR3 is expressed on activated T lymphocytes but not on resting T lymphocytes, nor on B lymphocytes, monocytes or granulocytes. CXCR3 expression is upregulated on NK cells by stimulation with TGF-beta 1. Two other ligands for CXCR3 are identified: MIG and ITAC. Binding of IP-10 to CXCR3 mediates calcium mobilization and chemotaxis in activated T cells. Chemotaxis and intracellular calcium mobilization are also induced by IP-10 binding to CXCR3 on activated NK cells. Within the thymus, IP-10 is a chemoattractant for TCR$\alpha\beta^+$ CD8$^+$ T cells, TCR$\gamma\delta^+$ T cells and NK-type cells.

IP-10 or its receptor CXCR3 have been identified in a variety of different inflammatory and autoimmune conditions, including multiple sclerosis, rheumatoid arthritis, ulcerative colitis, hepatitis, spinal cord injury, systemic lupus erythematosus, transplant rejection, Sjögren's syndrome. Accordingly, there is a need for therapeutic agents (e.g., anti-IP-10 antibodies) as well as methods for the treatment of IP-10 related diseases (e.g., inflammatory and autoimmune conditions).

SUMMARY OF THE INVENTION

In certain embodiments, the present invention provides a method of treating an IP-10-related disease in a subject in need of treatment. Such method comprises: (a) administering to the subject a predetermined dosage of an anti-IP-10 antibody; (b) detecting the level of the anti-IP-10 antibody in a sample of the subject; and (c) if the level of the anti-IP-10 antibody from step (b) is below a threshold exposure level, increasing the dosage of the anti-IP-10 antibody in the subject such that the IP-10 related disease in the subject is treated. Optionally, the anti-IP-10 antibody used in the methods specifically binds to human IP-10 and does not cross-react with human MIG or human ITAC. Preferably, the anti-IP-10 antibody is MDX-1100 (a fully human monoclonal antibody). An exemplary anti-IP-10 antibody comprises: (a) a heavy chain variable region comprising the amino acid sequence of SEQ ID NO: 2; and (b) a light chain variable region comprising the amino acid sequence of SEQ ID NO: 7. Another exemplary anti-IP-10 antibody comprises: (a) a heavy chain variable region CDR1 comprising SEQ ID NO: 3; (b) a heavy chain variable region CDR2 comprising SEQ ID NO: 4; (c) a heavy chain variable region CDR3 comprising SEQ ID NO: 5; (d) a light chain variable region CDR1 comprising SEQ ID NO: 8; (e) a light chain variable region CDR2 comprising SEQ ID NO: 9; and (f) a light chain variable region CDR3 comprising SEQ ID NO: 10.

In certain aspects, step (b) of the above described method is performed by detecting the level of the anti-IP-10 antibody via a method which comprises contacting said sample with an antibody which binds to the anti-IP-10 antibody under conditions suitable for antibody-antigen complex formation, followed by the detection of the antibody-antigen complex formation. Preferably, the antibody which binds to the anti-IP-10 antibody is an anti-idiotypic antibody. For example, the anti-idiotypic antibody binds to one or more CDRs of MDX-1100. Exemplary anti-idiotypic antibodies include, but are not limited to, 10C8, 6C9, 2F5, and 23H10 as described in the working examples. In a specific example, the detection method utilizes two anti-idiotypic antibodies, i.e., 10C8 and 23H10, as capture antibody and a detectable antibody (also referable to as "detection antibody"), respectively. Optionally, detection is accomplished by a means selected from the group consisting of EIA, ELISA, RIA, indirect competitive immunoassay, direct competitive immunoassay, non-competitive immunoassay, sandwich immunoassay, and agglutination assay.

In certain aspects, the IP-10-related disease of the above-described method is an inflammatory or autoimmune disease. Examples of the inflammatory or autoimmune diseases include, but are not limited to, multiple sclerosis, rheumatoid arthritis, inflammatory bowel disease (e.g., ulcerative colitis, Crohn's disease), systemic lupus erythematosus, Type I diabetes, inflammatory skin disorders (e.g., psoriasis, lichen planus), autoimmune thyroid disease (e.g., Graves' disease, Hashimoto's thyroiditis), Sjögren's syndrome, pulmonary inflammation (e.g., asthma, chronic obstructive pulmonary disease, pulmonary sarcoidosis, lymphocytic alveolitis), transplant rejection, spinal cord injury, brain injury (e.g., stroke), neurodegenerative diseases (e.g., Alzheimer's disease, Parkinson's disease), gingivitis, gene therapy-induced inflammation, diseases of angiogenesis, inflammatory kidney disease (e.g., IgA nephropathy, memranoproliferative glomerulonephritis, rapidly progressive glomerulonephritis) and atherosclerosis. A specific example of the IP-10 related disease is an inflammatory bowel disease (e.g., ulcerative colitis or Crohn's disease).

In certain embodiments, the present invention provides an isolated monoclonal antibody (e.g., an anti-idiotypic antibody) or an antigen binding portion thereof, which specifically binds to an anti-IP-10 antibody. Preferably, the anti-IP-10 antibody is MDX-1100. An exemplary anti-IP-10 antibody comprises: (a) a heavy chain variable region comprising the amino acid sequence of SEQ ID NO: 2; and (b) a light chain variable region comprising the amino acid sequence of SEQ ID NO: 7. Another exemplary anti-IP-10 antibody comprises: (a) a heavy chain variable region CDR1 comprising SEQ ID NO: 3; (b) a heavy chain variable region CDR2 comprising SEQ ID NO: 4; (c) a heavy chain variable region CDR3 comprising SEQ ID NO: 5; (d) a light chain variable region CDR1 comprising SEQ ID NO: 8; (e) a light chain variable region CDR2 comprising SEQ ID NO: 9; and (f) a light chain variable region CDR3 comprising SEQ ID NO: 10. Exemplary anti-idiotypic antibodies include, but are not limited to, 10C8, 6C9, 2F5, and 23H10 as described in the working examples.

In certain embodiments, the present invention provides a hybridoma cell line which produce a monoclonal antibody (e.g., an anti-idiotypic antibody) or an antigen binding portion thereof, which specifically binds to an anti-IP-10 antibody (e.g., MDX-1100).

In certain embodiments, the present invention provides a pharmaceutical composition comprising (1) a monoclonal antibody (e.g., an anti-idiotypic antibody) or an antigen binding portion thereof, which specifically binds to an anti-IP-10 antibody (e.g., MDX-1100), and (2) a pharmaceutically acceptable carrier.

In certain embodiments, the present invention provides a method of detecting a therapeutic anti-IP-10 antibody (e.g., MDX-1100) in a sample. Such method comprises contacting said sample with an antibody against the anti-IP-10 antibody (e.g., an anti-idiotypic antibody), or antigen-binding portion thereof, under conditions suitable for antibody-antigen complex formation, followed by the detection of said complex formation. For example, the anti-idiotypic antibody binds to one or more CDRs of MDX-1100. Exemplary anti-idiotypic antibodies include, but are not limited to, 10C8, 6C9, 2F5, and 23H10 as described in the working examples. In a specific example, the detection method utilizes two anti-idiotypic antibodies, i.e., 10C8 and 23H10, as capture antibody and a detectable antibody (also referable to as "detection antibody"), respectively. Optionally, detection is accomplished by a means selected from the group consisting of ETA, ELISA, RIA, indirect competitive immunoassay, direct competitive immunoassay, non-competitive immunoassay, sandwich immunoassay, and agglutination assay.

In certain embodiments, the present invention provides a kit which comprises (1) a monoclonal antibody (e.g., an anti-idiotypic antibody) or an antigen binding portion thereof, which specifically binds to an anti-IP-10 antibody (e.g., MDX-1100), and (2) reagents necessary for facilitating an antibody-antigen complex formation.

In certain embodiments, the present invention provides a method of treating an IP-10-related disease in a subject in need of treatment, comprising: (a) administering to the subject an anti-IP-10 antibody; (b) detecting the level of the anti-IP-10 antibody in a sample of the subject by an immunoassay; and (b) increasing the dosage of the anti-IP-10 antibody in the subject if the level of the anti-IP-10 antibody is below a threshold exposure level; and not increasing the dosage of the anti-IP-10 antibody in the subject if the level of the anti-IP-10 antibody is at or above a threshold exposure level.

In certain embodiments, the present invention provides isolated monoclonal anti-idiotypic antibodies that bind to an anti-IP-10 antibody (e.g., MDX-1100).

In certain specific embodiments, the invention provides an isolated monoclonal anti-idiotypic antibody, or antigen binding portion thereof, comprises: (a) a heavy chain variable region CDR1 comprising SEQ ID NO: 13; (b) a heavy chain variable region CDR2 comprising SEQ ID NO: 14; (c) a heavy chain variable region CDR3 comprising SEQ ID NO: 15; (d) a light chain variable region CDR1 comprising SEQ ID NO: 18; (e) a light chain variable region CDR2 comprising SEQ ID NO: 19; and (f) a light chain variable region CDR3 comprising SEQ ID NO: 20.

In certain specific embodiments of the invention, the isolated monoclonal anti-idiotypic antibody, or antigen binding portion thereof, comprises: (a) a heavy chain variable region CDR1 comprising SEQ ID NO: 23; (b) a heavy chain variable region CDR2 comprising SEQ ID NO: 24; (c) a heavy chain variable region CDR3 comprising SEQ ID NO: 25; (d) a light chain variable region CDR1 comprising SEQ ID NO: 28; (e) a light chain variable region CDR2 comprising SEQ ID NO: 29; and (f) a light chain variable region CDR3 comprising SEQ ID NO: 30.

In certain specific embodiments of the invention, the isolated monoclonal anti-idiotypic antibody, or antigen binding portion thereof, comprises: (a) a heavy chain variable region CDR1 comprising SEQ ID NO: 33; (b) a heavy chain variable region CDR2 comprising SEQ ID NO: 34; (c) a heavy chain variable region CDR3 comprising SEQ ID NO: 35; (d) a light chain variable region CDR1 comprising SEQ ID NO: 38; (e) a light chain variable region CDR2 comprising SEQ ID NO: 39; and (f) a light chain variable region CDR3 comprising SEQ ID NO: 40.

In certain specific embodiments of the invention, the isolated monoclonal anti-idiotypic antibody, or antigen binding portion thereof, comprises: (a) a heavy chain variable region CDR1 comprising SEQ ID NO: 43; (b) a heavy chain variable region CDR2 comprising SEQ ID NO: 44; (c) a heavy chain variable region CDR3 comprising SEQ ID NO: 45; (d) a light chain variable region CDR1 comprising SEQ ID NO: 48; (e) a light chain variable region CDR2 comprising SEQ ID NO: 49; and (f) a light chain variable region CDR3 comprising SEQ ID NO: 50.

In certain specific embodiments of the invention, the isolated monoclonal anti-idiotypic antibody, or antigen binding portion thereof, comprises: (a) a heavy chain variable region comprising the amino acid sequence of SEQ ID NO: 12; and (b) a light chain variable region comprising the amino acid sequence of SEQ ID NO: 17.

In certain specific embodiments of the invention, the isolated monoclonal anti-idiotypic antibody, or antigen binding portion thereof, comprises: (a) a heavy chain variable region comprising the amino acid sequence of SEQ ID NO: 22; and (b) a light chain variable region comprising the amino acid sequence of SEQ ID NO: 27.

In certain specific embodiments of the invention, the isolated monoclonal anti-idiotypic antibody, or antigen binding portion thereof, comprises: (a) a heavy chain variable region comprising the amino acid sequence of SEQ ID NO: 32; and (b) a light chain variable region comprising the amino acid sequence of SEQ ID NO: 37.

In certain specific embodiments of the invention, the isolated monoclonal anti-idiotypic antibody, or antigen binding portion thereof, comprises: (a) a heavy chain variable region comprising the amino acid sequence of SEQ ID NO: 42; and (b) a light chain variable region comprising the amino acid sequence of SEQ ID NO: 47.

In another aspect of the invention, monoclonal antibodies, or antigen-binding portions thereof, are provided that compete for binding to MDX-1100 with any of the aforementioned anti-idiotypic antibodies.

In certain embodiments, the anti-idiotypic antibody, or antigen binding portion thereof, is a murine antibody. In certain other embodiments, the anti-idiotypic antibody, or antigen binding portion thereof, is a chimeric, humanized or human antibody.

The anti-idiotypic antibodies of the invention can be, for example, full-length antibodies. Alternatively, the anti-idiotypic antibodies can be antibody fragments, such as Fab or Fab'2 fragments, or single chain antibodies.

In certain embodiments, the present invention provides a kit which comprises:
(1) the anti-idiotypic antibody, or antigen-binding portion thereof, of the invention; and
(2) reagents necessary for facilitating an antibody-antigen complex formation.

In certain embodiments, the present invention provides a composition comprising the anti-idiotypic antibody, or antigen-binding portion thereof, of the invention, and a pharmaceutically acceptable carrier.

In certain embodiments, the present invention provides a hybridoma cell line which produces the monoclonal anti-idiotypic antibody of the invention.

In certain embodiments, nucleic acid molecules encoding the anti-idiotypic antibodies, or antigen-binding portions thereof, of the invention are also encompassed by the invention, as well as expression vectors comprising such nucleic acids and host cells comprising such expression vectors.

BRIEF DESCRIPTION OF THE DRAWINGS

FIG. 12A shows the nucleotide sequence (SEQ ID NO: 1) and amino acid sequence (SEQ ID NO: 2) of the heavy chain variable region of the 6A5 human monoclonal antibody. The CDR1 (SEQ ID NO: 3), CDR2 (SEQ ID NO: 4) and CDR3 (SEQ ID NO: 5) regions are delineated and the V, D and J germline derivations are indicated.

FIG. 12B shows the nucleotide sequence (SEQ ID NO: 6) and amino acid sequence (SEQ ID NO: 7) of the light chain variable region of the 6A5 human monoclonal antibody. The CDR1 (SEQ ID NO: 8), CDR2 (SEQ ID NO: 9) and CDR3 (SEQ ID NO: 10) regions are delineated and the V and J germline derivations are indicated.

FIG. 13A shows the nucleotide sequence (SEQ ID NO: 11) and amino acid sequence (SEQ ID NO: 12) of the heavy chain variable region of the anti-idiotypic antibody 10C8. The CDR1 (SEQ ID NO: 13), CDR2 (SEQ ID NO: 14) and CDR3 (SEQ ID NO: 15) regions are delineated.

FIG. 13B shows the nucleotide sequence (SEQ ID NO: 16) and amino acid sequence (SEQ ID NO: 17) of the light chain variable region of the anti-idiotypic antibody 10C8. The CDR1 (SEQ ID NO: 18), CDR2 (SEQ ID NO: 19) and CDR3 (SEQ ID NO: 20) regions are delineated.

FIG. 14A shows the nucleotide sequence (SEQ ID NO: 21) and amino acid sequence (SEQ ID NO: 22) of the heavy chain variable region of the anti-idiotypic antibody 6C9. The CDR1 (SEQ ID NO: 23), CDR2 (SEQ ID NO: 24) and CDR3 (SEQ ID NO: 25) regions are delineated.

FIG. 14B shows the nucleotide sequence (SEQ ID NO: 26) and amino acid sequence (SEQ ID NO: 27) of the light chain variable region of the anti-idiotypic antibody 6C9. The CDR1 (SEQ ID NO: 28), CDR2 (SEQ ID NO: 29) and CDR3 (SEQ ID NO: 30) regions are delineated.

FIG. 15A shows the nucleotide sequence (SEQ ID NO: 31) and amino acid sequence (SEQ ID NO: 32) of the heavy chain variable region of the anti-idiotypic antibody 2F5. The CDR1 (SEQ ID NO: 33), CDR2 (SEQ ID NO: 34) and CDR3 (SEQ ID NO: 35) regions are delineated.

FIG. 15B shows the nucleotide sequence (SEQ ID NO: 36) and amino acid sequence (SEQ ID NO: 37) of the light chain variable region of the anti-idiotypic antibody 2F5. The CDR1 (SEQ ID NO: 38), CDR2 (SEQ ID NO: 39) and CDR3 (SEQ ID NO: 40) regions are delineated.

FIG. 16A shows the nucleotide sequence (SEQ ID NO: 41) and amino acid sequence (SEQ ID NO: 42) of the heavy chain variable region of the anti-idiotypic antibody 23H10. The CDR1 (SEQ ID NO: 43), CDR2 (SEQ ID NO: 44) and CDR3 (SEQ ID NO: 45) regions are delineated.

FIG. 16B shows the nucleotide sequence (SEQ ID NO: 46) and amino acid sequence (SEQ ID NO: 47) of the light chain variable region of the anti-idiotypic antibody 23H10. The CDR1 (SEQ ID NO: 48), CDR2 (SEQ ID NO: 49) and CDR3 (SEQ ID NO: 50) regions are delineated.

DETAILED DESCRIPTION OF THE INVENTION

Figure 1:
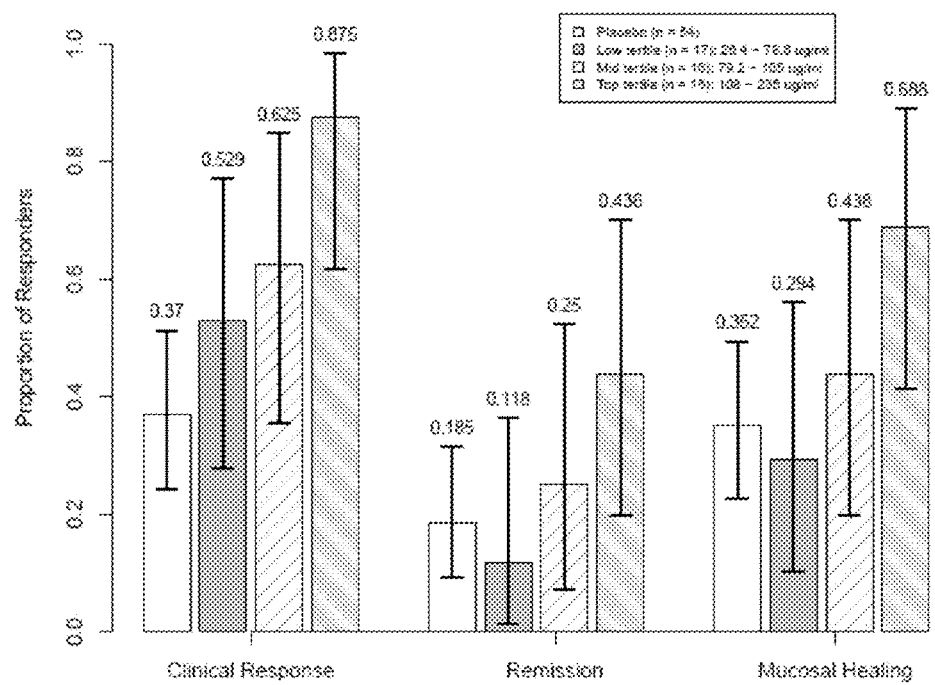
FIG. 1 shows Exposure-Response (E-R) relationship of clinical response, clinical remission and mucosal healing rates stratified by Cminss of MDX-1100 at Study Day 57.

In certain aspects, the present invention relates to therapeutic uses of a monoclonal antibody which binds to IP-10 (herein referred to as "IP-10 antibody" or "anti-IP-10 antibody"), for example, MDX-1100.

In certain embodiments, the present invention provides anti-idiotypic antibodies which bind to an IP-10 antibody (e.g., MDX-1100). In certain embodiments, the present invention provides methods of detecting an IP-10 antibody (e.g., MDX-1100) in a biologic sample using such anti-idiotypic antibodies.

In further embodiments, the invention provides novel and effective methods of treating IP-10-related diseases (e.g., inflammatory or autoimmune diseases), which comprise: (a) administering to the subject an anti-IP-10 antibody (e.g., MDX-1100); (b) detecting the level of the anti-IP-10 antibody in a sample of the subject; and (c) increasing dosages of the anti-IP-10 antibody to the subject if the level of the anti-IP-10 antibody from step (b) is below a level, such that the IP-10 related disease in the subject is treated. In further embodiments, the present invention provides a method of treating an IP-10-related disease in a subject in need of treatment, comprising: (a) administering to the subject an anti-IP-10 antibody; (b) detecting the level of the anti-IP-10 antibody in a sample of the subject by an immunoassay; and (c) increasing the dosage of the anti-IP-10 antibody in the subject if the level of the anti-IP-10 antibody is below a threshold exposure level; and not increasing the dosage of the anti-IP-10 antibody in the subject if the level of the anti-IP-10 antibody is at or above a threshold exposure level.

In order that the present invention may be more readily understood, certain terms are first defined. Additional definitions are set forth throughout the detailed description.

The terms "interferon gamma inducible protein 10" "IP-10", and "CXCL10" are used interchangeably, and include variants, isoforms and species homologs of human IP-10. Accordingly, human IP-10 antibodies of the invention may, in certain cases, cross-react with IP-10 from species other than human. In other cases, the antibodies may be completely specific for human IP-10 and may not exhibit species or other types of cross-reactivity. The complete amino acid sequence of human IP-10 has GENBANK® accession number NP_001556. The complete amino acid sequence of rhesus monkey IP-10 has GENBANK® accession number AAK95955. The complete amino acid sequence of mouse IP-10 has GENBANK® accession number NP_067249.

The term "CXCR3" refers to the receptor for IP-10 (CXCL10). The complete amino acid sequence of human CXCR3 has GENBANK® accession number NP_001495.

The term "MIG" refers to a ligand for CXCR3, also known as monokine induced by gamma interferon, which is distinct from IP-10. The complete amino acid sequence of human MIG has GENBANK® accession number NP_002407.

The term "ITAC" refers to a ligand for CXCR3, also known as interferon-inducible T cell alpha chemoattractant, which is distinct from IP-10. The complete amino acid sequence of human ITAC has GENBANK® accession number NP_005400.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., IP-10 or an IP-10 antibody). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., *Nature*, 341:544-546 (1989)), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science*, 242:423-426 (1988); and Huston et al., *Proc. Natl. Acad. Sci. USA*, 85:5879-5883 (1988)). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds IP-10 is substantially free of antibodies that specifically bind antigens other than IP-10). An isolated antibody that specifically binds IP-10 may, however, have cross-reactivity to other antigens, such as IP-10 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Anti-Idiotypic Antibodies which Bind to an Anti-IP-10 Antibody

In certain aspects, the present invention provides monoclonal or polyclonal antibodies specific for an anti-IP-10 antibody (e.g., MDX-1100). Preferably, such antibody is an anti-idiotypic (anti-Id) antibody. An anti-idiotypic (anti-Id) antibody is an antibody which recognizes unique determinants generally associated with the antigen-binding site of an antibody.

In certain specific embodiments, the present invention provides monoclonal anti-idiotypic antibodies which bind to the MDX-1100 antibody. Exemplary monoclonal anti-idiotypic antibodies include, but are not limited to 10C8, 6C9, 2F5, and 23H10.

For example, the isolated monoclonal anti-idiotypic antibody, or antigen binding portion thereof, comprises: (a) a heavy chain variable region CDR1 comprising SEQ ID NO: 13; (b) a heavy chain variable region CDR2 comprising SEQ ID NO: 14; (c) a heavy chain variable region CDR3 comprising SEQ ID NO: 15; (d) a light chain variable region CDR1 comprising SEQ ID NO: 18; (e) a light chain variable region CDR2 comprising SEQ ID NO: 19; and (f) a light chain variable region CDR3 comprising SEQ ID NO: 20.

For example, the isolated monoclonal anti-idiotypic antibody, or antigen binding portion thereof, comprises: (a) a heavy chain variable region CDR1 comprising SEQ ID NO: 23; (b) a heavy chain variable region CDR2 comprising SEQ ID NO: 24; (c) a heavy chain variable region CDR3 comprising SEQ ID NO: 25; (d) a light chain variable region CDR1 comprising SEQ ID NO: 28; (e) a light chain variable region CDR2 comprising SEQ ID NO: 29; and (f) a light chain variable region CDR3 comprising SEQ ID NO: 30.

For example, the isolated monoclonal anti-idiotypic antibody, or antigen binding portion thereof, comprises: (a) a heavy chain variable region CDR1 comprising SEQ ID NO: 33; (b) a heavy chain variable region CDR2 comprising SEQ ID NO: 34; (c) a heavy chain variable region CDR3 comprising SEQ ID NO: 35; (d) a light chain variable region CDR1 comprising SEQ ID NO: 38; (e) a light chain variable region CDR2 comprising SEQ ID NO: 39; and (f) a light chain variable region CDR3 comprising SEQ ID NO: 40.

For example, the isolated monoclonal anti-idiotypic antibody, or antigen binding portion thereof, comprises: (a) a heavy chain variable region CDR1 comprising SEQ ID NO: 43; (b) a heavy chain variable region CDR2 comprising SEQ ID NO: 44; (c) a heavy chain variable region CDR3 comprising SEQ ID NO: 45; (d) a light chain variable region CDR1 comprising SEQ ID NO: 48; (e) a light chain variable region CDR2 comprising SEQ ID NO: 49; and (f) a light chain variable region CDR3 comprising SEQ ID NO: 50.

For example, the isolated monoclonal anti-idiotypic antibody, or antigen binding portion thereof, comprises: (a) a heavy chain variable region comprising the amino acid sequence of SEQ ID NO: 12; and (b) a light chain variable region comprising the amino acid sequence of SEQ ID NO: 17.

For example, the isolated monoclonal anti-idiotypic antibody, or antigen binding portion thereof, comprises: (a) a heavy chain variable region comprising the amino acid sequence of SEQ ID NO: 22; and (b) a light chain variable region comprising the amino acid sequence of SEQ ID NO: 27.

For example, the isolated monoclonal anti-idiotypic antibody, or antigen binding portion thereof, comprises: (a) a heavy chain variable region comprising the amino acid sequence of SEQ ID NO: 32; and (b) a light chain variable region comprising the amino acid sequence of SEQ ID NO: 37.

For example, the isolated monoclonal anti-idiotypic antibody, or antigen binding portion thereof, comprises: (a) a heavy chain variable region comprising the amino acid sequence of SEQ ID NO: 42; and (b) a light chain variable region comprising the amino acid sequence of SEQ ID NO: 47.

In certain embodiments, the anti-idiotypic antibodies of the invention are selected from a murine antibody, a chimeric antibody, a humanized antibody, and a human antibody. In certain embodiments, the anti-idiotypic antibodies of the invention can be, for example, full-length antibodies. Alternatively, the anti-idiotypic antibodies can be antibody fragments, such as Fab or Fab'2 fragments, or single chain antibodies.

In certain embodiments, an anti-idiotypic antibody of the invention comprises one or more conservative sequence modifications in the heavy chain variable region (e.g., CDR1, CDR2 or CDR3 sequences) and/or in the light chain variable region (e.g., CDR1, CDR2 or CDR3 sequences) of the anti-idiotypic antibodies described herein (e.g., 10C8, 6C9, 2F5 or 23H10), wherein the modified antibodies retain the desired functional properties of the anti-idiotypic antibodies of the invention. As used herein, the term "conservative sequence modifications" is intended to refer to amino acid modifications that do not significantly affect or alter the binding characteristics of the anti-idiotypic antibody containing the amino acid sequence. Such conservative modifications include amino acid substitutions, additions and deletions. Modifications can be introduced into an anti-idiotypic antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an anti-idiotypic antibody of the invention can be replaced with other amino acid residues from the same side chain family and the altered antibody can be tested for retained function using the assays described in the working examples.

As defined herein, anti-idiotypic antibodies of the invention include antibodies whose heavy and light chain variable regions comprising amino acid sequences that are homologous to the amino acid sequences of the preferred antibodies described herein (e.g., 10C8, 6C9, 2F5 or 23H10), and wherein the antibodies retain the desired functional properties of the anti-idiotypic antibodies. For example, an anti-idiotypic antibody includes an antibody comprising: (a) the heavy chain variable region which comprises an amino acid sequence that is at least 80%, 90%, 95%, 98%, or 99% identical to an amino acid sequence selected from SEQ ID NOs: 12, 22, 32, and 42; (b) the light chain variable region which comprises an amino acid sequence that is at least 80%, 90%, 95%, 98%, or 99% identical to an amino acid sequence selected from SEQ ID NOs: 17, 27, 37, and 47. In another example, an anti-idiotypic antibody includes an antibody comprising: (a) a heavy chain variable region CDR1 which comprises an amino acid sequence that is at least 80%, 90%, 95%, 98%, or 99% identical to an amino acid sequence selected from SEQ ID NOs: 13, 23, 33, and 43; (b) a heavy chain variable region CDR2 which comprises an amino acid sequence that is at least 80%, 90%, 95%, 98%, or 99% identical to an amino acid sequence selected from SEQ ID NOs: 14, 24, 34, and 44; (c) a heavy chain variable region CDR3 which comprises an amino acid sequence that is at least 80%, 90%, 95%, 98%, or 99% identical to an amino acid sequence selected from SEQ ID NOs: 15, 25, 35, and 45; (d) a light chain variable region CDR1 which comprises an amino acid sequence that is at least 80%, 90%, 95%, 98%, or 99% identical to an amino acid sequence selected from SEQ ID NOs: 18, 28, 38, and 48; (e) a light chain variable region CDR2 which comprises an amino acid sequence that is at least 80%, 90%, 95%, 98%, or 99% identical to an amino acid sequence selected from SEQ ID NOs: 19, 29, 39, and 49; and (f) a light chain variable region CDR3 which comprises an amino acid sequence that is at least 80%, 90%, 95%, 98%, or 99% identical to an amino acid sequence selected from SEQ ID NOs: 20, 30, 40, and 50.

Nucleic Acid Molecules Encoding Anti-Idiotypic Antibodies of the Invention

Another aspect of the invention pertains to nucleic acid molecules encoding the anti-idiotypic antibodies, or antigen-binding portions thereof, of the invention, as well as expression vectors comprising such nucleic acids and host cells comprising such expression vectors.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, Ausubel, F. et al., ed., *Current Protocols in Molecular Biology*, Greene Publishing and Wiley Interscience, New York (1987). A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 10C8, 6C9, 2F5, and 23H10 monoclonal antibodies. DNA sequences encoding the VH sequences of 10C8, 6C9, 2F5, and 23H10 are shown in SEQ ID NOs: 11, 21, 31, and 41, respectively. DNA sequences encoding the VL sequences of 10C8, 6C9, 2F5, and 23H10 are shown in SEQ ID NOs: 16, 26, 36, and 46, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). For example, the sequences of human heavy chain constant region genes are known in the art (see e.g., Kabat, E. A. et al., *Sequences of Proteins of Immunological Interest*, Fifth Edition, U.S. Department of Health and Human Services, NIH Publication No. 91-3242 (1991)) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. For example, the sequences of human light chain constant region genes are known in the art (see e.g., Kabat, E. A. et al., *Sequences of Proteins of Immunological Interest*, Fifth Edition, U.S. Department of Health and Human Services, NIH Publication No. 91-3242 (1991)) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al., *Science*, 242:423-426 (1988); Huston et al., *Proc. Natl. Acad. Sci. USA*, 85:5879-5883 (1988); McCafferty et al., *Nature*, 348:552-554 (1990)).

Antibodies that Bind to the Same Epitope as Anti-Idiotypic Antibodies of the Invention In another aspect of the invention, isolated monoclonal antibodies, or antigen-binding portions thereof, are provided that compete for binding to MDX-1100 with any of the aforementioned anti-idiotypic antibodies. In certain embodiments, the invention provides isolated monoclonal antibodies that bind to the same epitope as do the various anti-idiotypic antibodies of the invention, such as monoclonal antibodies that bind to the same epitope as the 10C8, 6C9, 2F5 or 23H10 antibodies described herein. Such additional antibodies can be identified based on their ability to cross-compete (e.g., to competitively inhibit the binding of, in a statistically significant manner) with other antibodies of the invention (e.g., 10C8, 6C9, 2F5 or 23H10) in MDX-1100 binding assays. The ability of a test antibody to inhibit the binding of, e.g., 10C8, 6C9, 2F5 or 23H10 to MDX-1100 demonstrates that the test antibody can compete with that antibody for binding to MDX-1100; such an antibody may, according to non-limiting theory, bind to the same or a related (e.g., a structurally similar or spatially proximal) epitope on MDX-1100 as the antibody with which it competes. Optionally, the antibody that binds to the same epitope on MDX-1100 as 10C8, 6C9, 2F5 or 23H10 is selected from a murine antibody, a chimeric antibody, a humanized antibody, or a human antibody.

Methods of Generating Anti-Idiotypic Antibodies

An anti-Id antibody can be prepared by immunizing an animal with an antibody to which an anti-Id is being prepared. The immunized animal will recognize and respond to the idiotypic determinants of the immunizing antibody by producing an antibody to these idiotypic determinants (the anti-Id antibody). See, e.g., U.S. Pat. No. 4,699,880. Exemplary techniques for the production of monoclonal antibodies which bind to an anti-IP-10 antibody are provided below.

Monoclonal antibodies may be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, Academic Press (1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high-level production of antibody by the selected antibody-producing cells, and are sensitive to a medium such as HAT medium. Among these, exemplary myeloma cell lines are murine myeloma lines, such as those derived from MOPC-21 and MPC-11 mouse tumors available from the Salk Institute Cell Distribution Center, San Diego, Calif. USA, and SP-2, P3X63Ag.U.1, or X63-Ag8-653 cells available from the American Type Culture Collection, Manassas, Va. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63, Marcel Dekker, Inc., New York (1987)).

Culture medium in which hybridoma cells are growing is assayed for production of monoclonal antibodies directed against the antibody of interest. Preferably, the binding specificity of monoclonal antibodies produced by hybridoma cells is determined by immunoprecipitation or by an in vitro binding assay, such as radioimmunoassay (RIA) or ELISA. Such clones are also screened for those that produce the least background noise in the assay when used as capture reagents and/or detectable antibodies. The binding affinity of the monoclonal antibody can, for example, be determined by the Scatchard analysis of Munson et al., Anal. Biochem., 107:220 (1980). After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103, Academic Press (1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-SEPHAROSE® agarose chromatography, hydroxylapatite chromatography, gel electrophoresis, dialysis, or affinity chromatography.

One specific preparation technique using hybridoma technology comprises immunizing mice such as CAF1 mice or Balb/c, for example, by injection in the footpads or spleen, with the antibody of interest in an adjuvant such as monophosphoryl lipid A/trehalose dicorynomycolate or as a conjugate of the antibody of interest with keyhole limpet haemocyanin (KLH) or with Limulus hemocyanin. Injections are done as many times as needed. The mice are sacrificed and popliteal lymph nodes or splenocytes obtained from the immunized mice, especially those with high titers, are fused with a murine myeloma cell line such as SP2/0 or P3X63Ag.U.1 (American Type Culture Collection (ATCC, Manassas, Va.)). The resulting hybridomas are screened for antibodies with binding affinity for the antibody of interest but not other antibodies binding to a different antigen. This screening may take place by conventional ELISA for secretion of antibody that binds to immobilized antibody of interest or for production of IgG with an inhibition capacity of more than about 95% (inhibition of binding of the antibody of interest to the protein antigen). This screen defines a population of antibodies with nominal or higher reactivity as well as selectivity for the antibody of interest. Further selection may be performed to identify those antibodies with properties especially preferred for ELISAs. The criteria used for selecting a preferred anti-idiotypic antibody include that it binds to the antibody of interest with relatively high affinity (Kd<about $10^{-8}$ M), and that its binding to the antibody of interest should be mutually exclusive with binding to the analyte transmembrane protein. It should also provide the cleanest assay with the least background noise.

The positive clones may be re-screened using surface plasmon resonance using a BIACORE® instrument to measure the affinity of the anti-idiotypic antibody for the antibody of interest (as reflected in its off-rate) and the mutual exclusivity of binding. Rabbit anti-mouse IgG(Fc) may be immobilized onto the biosensor surface and used to capture anti-idiotypic antibodies from hybridoma culture supernates. The antibody of interest at 0.2 nM alone and in the presence of 0.9 nM C-reactive protein (CRP) may be injected over the surface of the immobilized anti-idiotypic antibody and the relative mass accumulation compared. The hybridoma cells that are selected are cloned as by limiting dilution to obtain the desired clones. The anti-idiotypic antibody can then be purified and isolated from these clones. See, e.g., U.S. Publication Nos. 2002/0142356 and 2008/0176257 for examples of preparing an anti-idiotypic antibody, as well as Durrant et al., *Int. J. Cancer*, 92(3):414-420 (2001) and Bhattacharya-Chatterjee, *Curr. Opin. Mol. Ther.*, 3(1):63-69 (2001).

In certain embodiments, the monoclonal antibodies may also be produced recombinantly. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opin. Immunol.*, 5:256-262 (1993) and Pluckthun, *Immunol. Revs.*, 130:151-188 (1992).

In a further embodiment, antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high-affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (see, e.g., U.S. Pat. No. 4,816,567; Morrison et al., *Proc. Natl. Acad. Sci. USA*, 81:6851 (1984)), or by covalently joining to the immunoglobulin-coding sequence all or part of the coding sequence for a non-immunoglobulin polypeptide. Many of the procedures useful for practicing the present invention, whether or not described herein in detail, are well known to those skilled in the arts of molecular biology, biochemistry, immunology, and medicine. Once the antibody of interest is identified, generating the antibodies which bind to MDX-1100 would be within the skill of the ordinarily skilled practitioner in this field.

Methods of Detection Assays

In certain embodiments, the antibodies against an anti-IP-10 antibody (e.g., MDX-1100) or antigen binding portion thereof, of the invention can be used in a method for the detection of a therapeutic anti-IP-10 antibody (e.g., MDX-1100) and fragments and derivatives thereof in a subject. Preferably, such antibody is an anti-idiotypic (anti-Id) antibody. For example, a body fluid (e.g., blood, serum or plasma) or tissue sample from the test subject is contacted with an anti-MDX-1100 monoclonal antibody, or antigen binding portion thereof, of the invention under conditions suitable for the formation of antibody-antigen complexes. The presence or amount of such complexes can then be determined by methods described herein and otherwise known in the art (see, e.g., O'Connor et al., *Cancer Res.*, 48:1361-1366 (1988)), in which the presence or amount of complexes found in the test sample is compared to the presence or amount of complexes found in a series of standards or control samples containing a known amount of antigen. Accordingly, the present invention relates to methods for detecting an anti-IP-10 antibody such as MDX-1100 (or a fragment and/or derivative thereof) in a biological sample (e.g., blood, serum, plasma, urine, cerebrospinal fluid, mucus, or saliva).

In any of the described detection assays, the method can employ an immunoassay, e.g., an enzyme immunoassay (EIA), enzyme-linked immunosorbant assay (ELISA), radioimmunoassay (RIA), indirect competitive immunoassay, direct competitive immunoassay, non-competitive immunoassay, sandwich immunoassay, agglutination assay or other immunoassay describe herein and known in the art (see, e.g., Zola, *Monoclonal Antibodies: A Manual of Techniques*, pp. 147-158, CRC Press, Inc. (1987)). Immunoassays may be constructed in heterogeneous or homogeneous formats. Heterogeneous immunoassays are distinguished by incorporating a solid phase separation of bound analyte from free analyte or bound label from free label. Solid phases can take a variety of forms well known in the art, including but not limited to tubes, plates, beads, and strips. One particular form is the microtiter plate. The solid phase material may be comprised of a variety of glasses, polymers, plastics, papers, or membranes. Particularly desirable are plastics such as polystyrene. Heterogeneous immunoassays may be competitive or non-competitive (i.e., sandwich formats) (see, e.g., U.S. Pat. No. 7,195,882).

In a specific embodiment, the present invention provides a method of detecting MDX-1100 in a biologic sample from a subject, which comprises the following steps (see below).

In the first step of the assay, the biological sample is contacted and incubated with an immobilized capture antibody such as an anti-idiotypic antibody directed against MDX-1100. These anti-idiotypic antibodies are preferably monoclonal antibodies, and may be from any species, but preferably they are rodent, more preferably murine (e.g., 10C8, 6C9, 2F5, and 23H10 as described in the working examples) Immobilization conventionally is accomplished by insolubilizing the capture antibody either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al., *J. Immunol. Methods*, 57:87-98 (1983)), or afterward, e.g., by immunoprecipitation.

The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogens-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In a specific embodiment, the immobilized capture antibody is coated on a microtiter plate, and in particular the solid phase used is a multi-well microtiter plate that can be used to analyze several samples at one time. The most preferred is a MICROTEST® or MaxiSorp 96-well ELISA plate such as that sold as NUNC® MaxiSorb or IMMULON®. The solid phase is coated with the capture antibody as defined above, which may be linked by a non-covalent or covalent interaction or physical linkage as desired. Techniques for attachment include those described in U.S. Pat. No. 4,376, 110 and the references cited therein. If covalent, the plate or other solid phase is incubated with a cross-linking agent together with the capture antibody under conditions well known in the art such as for one hour at room temperature. Commonly used cross-linking agents for attaching the capture reagents to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1.5 to 3 hours.

The conditions for incubation of sample and immobilized capture antibody are selected to maximize sensitivity of the assay and to minimize dissociation, and to ensure that any antibody of interest present in the sample binds to the immobilized capture antibody. Preferably, the incubation is accomplished at fairly constant temperatures, ranging from about 0° C. to about 40° C., preferably at or about room temperature. The time for incubation is generally no greater than about 10 hours. Preferably, the incubation time is from about 0.5 to 3 hours, and more preferably about 1.5-3 hours at or about room temperature to maximize binding of the antibody of interest to the capture antibody. The duration of incubation may be longer if a protease inhibitor is added to prevent proteases in the biological fluid from degrading the antibody of interest.

In a second step of the assay method herein, which is optional, the biological sample is separated (preferably by washing) from the immobilized capture antibody to remove uncaptured antibody of interest (e.g., MDX-1100). The washing may be done three or more times. The temperature of washing is generally from refrigerator to moderate temperatures, with a constant temperature maintained during the assay period, typically from about 0-40° C., more preferably about 4-30° C. A cross-linking agent or other suitable agent may also be added at this stage to allow the now-bound antibody of interest to be covalently attached to the capture reagents if there is any concern that the captured antibody of interest may dissociate to some extent in the subsequent steps.

In the third step, the immobilized capture antibody with any bound antibody of interest (e.g., MDX-1100) are contacted with a detectable antibody, preferably at a temperature of about 20-40° C., more preferably about 36-38° C. While the detectable antibody may be a polyclonal or monoclonal antibody, preferably it is a monoclonal antibody, more preferably rodent, still more preferably murine. In a specific embodiment, a detectable antibody of the assay herein is an anti-idiotypic antibody against MDX-1100, such as 10C8, 6C9, 2F5, and 23H10 as described in the working examples. Optionally, the detectable antibody is directly detectable, and such as biotinylated. The detection means for the biotinylated label is preferably avidin or streptavidin-HRP, and the readout of the detection means is preferably fluorimetric or colorimetric.

The same anti-idiotypic antibody can be used for coat (capture) and detection in the assay, or different antibodies can be used for coat (capture) and detection. They are preferably selected so that the background noise is minimized.

In the fourth step of the assay method, the level of any free antibody of interest (e.g., MDX-1100) from the sample that is now bound to the capture antibody is measured using a detection means for the detectable antibody. If the biological sample is from a clinical patient, the measuring step preferably comprises comparing the reaction that occurs as a result of the above three steps with a standard curve to determine the level of antibody of interest compared to the known amount.

The detectable antibody (herein referred to as the "first antibody") will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ. The label used for either the first or second antibody is any detectable functionality that does not interfere with the binding of free antibody of interest to the anti-idiotypic antibodies. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, dansyl, umbelliferone, luciferases, e.g., firefly luciferase and bacterial luciferase (see, e.g., U.S. Pat. No. 4,737,456), luciferin, 2,3-dihydrophthalazinediones, HRP, alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like. In a specific embodiment, the label is biotin and the detection means is avidin or streptavidin-HRP.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, e.g., U.S. Pat. No. 3,940,475 (fluorimetry) and U.S. Pat. No. 3,645,090 (enzymes); Hunter et al., *Nature*, 144:945 (1962); David et al., *Biochemistry*, 13:1014-1021 (1974); Pain et al., *J. Immunol. Methods*, 40:219-230 (1981); and Nygren, *J. Histochem. Cytochem.*, 30:407-412 (1982). An exemplary label is biotin using streptavidin-HRP for detection means. The conjugation of such label, including the enzymes, to an antibody is a standard manipulative procedure for one of ordinary skill in immunoassay techniques. See, e.g., O'Sullivan et al. "Methods for the Preparation of Enzyme-antibody Conjugates for Use in Enzyme Immunoassay", in *Methods in Enzymology*, Langone, J. J. et al., eds., Vol. 73, pp. 147-166, Academic Press, New York, N.Y. (1981).

Following the addition of last labeled antibody, the amount of bound antibody is determined by removing excess unbound labeled antibody through washing and then measuring the amount of the attached label using a detection method appropriate to the label, and correlating the measured amount with the amount of the antibody of interest in the biological sample. For example, in the case of enzymes, the amount of color developed and measured will be a direct measurement of the amount of the antibody of interest present. Specifically, if HRP is the label, the color is detected using the substrate OPD at 490-nm absorbance. In another example, after an enzyme-labeled second antibody directed against the first unlabeled antibody is washed from the immobilized phase, color or chemiluminescence is developed and measured by incubating the immobilized capture reagent with a substrate of the enzyme. Then the concentration of the antibody of interest is calculated by comparing with the color or chemiluminescence generated by the standard antibody of interest run in parallel.

Kits

In certain embodiments, the present invention provides kits that can be used in the assays described above, which comprise one or more antibodies (monoclonal or polyclonal) against an anti-IP-10 antibody of interest (e.g., MDX-1100), or an antigen binding portion thereof as well as reagents necessary for facilitating an antibody-antigen complex formation and/or detection. Preferably, such antibodies of the kits are anti-idiotypic antibodies. For example, a kit of the present invention is a packaged combination including the basic elements of: (a) capture reagents comprising at least one anti-idiotypic antibody against MDX-1100 (herein referred to as a "capture antibody"); (b) at least one detectable (labeled or unlabeled) anti-idiotypic antibody that binds to a different epitope on MDX-1100; and (c) instructions on how to perform the assay method using these reagents.

Optionally, the kit further comprises a solid support for the capture antibodies, which may be provided as a separate element or on which the capture antibodies are already immobilized. Hence, the capture antibodies in the kit may be immobilized on a solid support, or they may be immobilized on such support that is included with the kit or provided separately from the kit. For example, the capture antibodies are coated on a microtiter plate. The detectable antibodies may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or β-galactosidase with MUG.

In a specific embodiment, the capture antibodies are anti-idiotypic antibodies selected from 10C8, 6C9, 2F5, and 23H10 as described in the working examples. Also, in a specific embodiment, the detectable antibodies are anti-idiotypic antibodies selected from 10C8, 6C9, 2F5, and 23H10, wherein the capture antibody and the detectable antibody bind to different epitopes on MDX-1100.

The kit may further comprise, as a positive control, the antibody of interest (e.g., purified MDX-1100) or a fragment thereof which binds to the anti-idiotypic antibody. The kits may further comprise, as a negative control, an antibody which does not react with the anti-idiotypic antibody. The kit may further comprise other additives such as stabilizers, washing and incubation buffers, and the like. The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

Therapeutic Methods

In certain embodiments, the invention provides novel and effective methods of treating IP-10-related diseases (e.g., inflammatory or autoimmune diseases), which comprise: (a) administering to the subject a predetermined dosage of an anti-IP-10 antibody; (b) detecting the level of the anti-IP-10 antibody in a sample of the subject; and (c) if the level of the anti-IP-10 antibody from step (b) is below a threshold exposure level, increasing the dosage of the anti-IP-10 antibody (e.g., to a therapeutically effective dosage) in the subject, such that the IP-10 related disease in the subject is treated; and if the level of the anti-IP-10 antibody from step (b) is at or above a threshold exposure level, not increasing the dosage of the anti-IP-10 antibody in the subject. In particular, the level of the anti-IP-10 antibody in a sample can be detected by any of assays as described above.

The term "treating" includes the administration of anti-IP-10 antibodies to prevent or delay the onset of the symptoms, complications, or biochemical indicia of an IP-10-related disease, alleviating the symptoms or arresting or inhibiting further development of the disease (e.g., an inflammatory or autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

The term "dosage" or "dose" as used herein, refers to an amount of an anti-IP-10 antibody which is administered to a subject.

The term "therapeutically effective dosage", as used herein, refers to a dosage of an anti-IP-10 antibody which preferably results in a decrease in severity of disease symptoms, an increase in frequency and duration of disease symptom-free periods, or a prevention of impairment or disability due to the disease affliction. One of ordinary skill in the art would be able to determine such amounts based on such factors as the subject's size, the severity of the subject's symptoms, and the particular composition or route of administration selected.

The term "threshold exposure level", as used herein, refers to a minimum exposure level which allows for clinically meaningful induction and/or maintenance of disease remission after administering an anti-IP-10 antibody in a subject during the induction phase and/or maintenance phase. The threshold exposure level can be readily determined, such as by the exposure-response analyses as described in the working examples. For example, the threshold exposure level can be a trough concentration ranging from 40-150 µg/mL (e.g., 40, 50, 60, 70, 80, 90, 100, 110, 120, 130, 140, 150 µg/mL).

The present invention is based, at least in part, on observations made during clinical testing of a human anti-IP-10 antibody (i.e., MDX-1100) in treating an inflammatory bowel disease (IBD), as described below. The tests demonstrate variability in MDX-1100's pharmacokinetic (PK) parameters in patients treated with MDX-1100. Meanwhile, the tests demonstrate very low immunogenicity of MDX-1100 in this study. Furthermore, the tests demonstrate a strong drug exposure/response relationship whereby trough drug levels were directly related to efficacy.

For many inflammatory or autoimmune diseases (e.g., IBD), treatments have traditionally included (1) an induction phase with a relatively higher drug dosage with the goal of bringing acute disease under control; and (2) a maintenance phase (or treatment phase) with a relatively lower dosage with the goal of preventing disease relapse (see, e.g., U.S. Publication No. 2006/0009385). Although the above-mentioned clinical test results were obtained during the induction phase, these observations (e.g., variability in PK parameters, very low immunogenicity, and a strong exposure/response relationship) appear to be intrinsic to the property of the molecule and/or its mechanism of action. Accordingly, Applicants expect similar observations in the maintenance phase.

One aspect of the present invention is to minimize drug overdose to patients and at the same time to optimize efficacy (e.g., in the maintenance phase). In a specific example, the present invention provides a method of treating an IP-10-related disorder, which comprises: (1) administering to a subject with a maintenance dosage (e.g., a predetermined dosage) of an anti-IP-10 antibody; (2) if the subject fails to maintain response (also referred to as "lose response" or "relapse"), a diagnostic assay will be used to measure the exposure level (e.g., blood concentration) of the anti-IP-10 antibody in the subject; (3)) if the exposure level of the anti-IP-10 antibody is below a threshold exposure level, escalating the dosage in the subject, such that drug response is maintained in the subject. This ensures that during chronic therapy, patients receive personalized dosage (e.g., only as much drug as needed), as determined by clinical assessment and objective drug concentration measurement.

Anti-IP-10 Antibodies

In certain aspect, the present invention relates to therapeutic uses of anti-IP-10 antibodies which are characterized by particular functional features or properties. For example, the antibodies bind specifically to human IP-10. Additionally, the antibodies may cross react with IP-10 from one or more non-human primates, such as rhesus monkey. Preferably, the antibodies do not cross react with mouse IP-10. Moreover, although MIG and ITAC are also ligands for the CXCR3 receptor, the anti-IP-10 antibodies preferably do not cross react with human MIG or human ITAC. Furthermore, the anti-IP-10 antibodies are capable of inhibiting one or more functional activities of IP-10. For example, in one embodiment, the anti-IP-10 antibodies inhibit the binding of IP-10 to CXCR3. In another embodiment, the anti-IP-10 antibodies inhibit IP-10 induced calcium flux. In yet another embodiment, the anti-IP-10 antibodies inhibit IP-10 induced cell migration (chemotaxis). Other functional features or properties of anti-IP-10 antibodies are also described in U.S. Publication No. 2005/0191293, the content of which is expressly incorporated by reference.

Exemplary anti-IP-10 antibodies are monoclonal antibodies 1D4, 1E1, 2G1, 3C4, 6A5, 6A8, 6B10, 7C10, 8F6, 10A12 and 13C4 as described in U.S. Publication No. 2005/0191293, the content of which is expressly incorporated by reference.

In a preferred embodiment, an anti-IP-10 antibody comprises: (a) a heavy chain variable region comprising the amino acid sequence of SEQ ID NO: 2; and (b) a light chain variable region comprising the amino acid sequence of SEQ ID NO: 7.

In another preferred embodiment, an anti-IP-10 antibody comprises: (a) a heavy chain variable region CDR1 comprising SEQ ID NO: 3; (b) a heavy chain variable region CDR2 comprising SEQ ID NO: 4; (c) a heavy chain variable region CDR3 comprising SEQ ID NO: 5; (d) a light chain variable region CDR1 comprising SEQ ID NO: 8; (e) a light chain variable region CDR2 comprising SEQ ID NO: 9; and (f) a light chain variable region CDR3 comprising SEQ ID NO: 10.

As defined herein, anti-IP-10 antibodies include antibodies whose heavy and light chain variable regions comprising amino acid sequences that are homologous to the amino acid sequences of the preferred antibodies described herein, and wherein the antibodies retain the desired functional properties of the anti-IP-10 antibodies. For example, an anti-IP-10 antibody includes an antibody comprising: (a) the heavy chain variable region comprises an amino acid sequence that is at least 80%, 90%, 95%, 98%, or 99% identical to an amino acid sequence selected from the group consisting of SEQ ID NO: 2; (b) the light chain variable region comprises an amino acid sequence that is at least 80%, 90%, 95%, 98%, or 99% identical to an amino acid sequence selected from the group consisting of SEQ ID NOs: 7. In another example, an anti-IP-10 antibody includes an antibody comprising: (a) a heavy chain variable region CDR1 comprising an amino acid sequence that is at least 80%, 90%, 95%, 98%, or 99% identical to SEQ ID NO: 3; (b) a heavy chain variable region CDR2 comprising an amino acid sequence that is at least 80%, 90%, 95%, 98%, or 99% identical to SEQ ID NO: 4; (c) a heavy chain variable region CDR3 comprising an amino acid sequence that is at least 80%, 90%, 95%, 98%, or 99% identical to SEQ ID NO: 5; (d) a light chain variable region CDR1 comprising an amino acid sequence that is at least 80%, 90%, 95%, 98%, or 99% identical to SEQ ID NO: 8; (e) a light chain variable region CDR2 comprising an amino acid sequence that is at least 80%, 90%, 95%, 98%, or 99% identical to SEQ ID NO: 9; and (f) a light chain variable region CDR3 comprising an amino acid sequence that is at least 80%, 90%, 95%, 98%, or 99% identical to SEQ ID NO: 10. Any of the homologous antibody specifically binds to IP-10, and exhibits at least one of the following functional properties: (i) the antibody inhibits binding of IP-10 to CXCR3; (ii) the antibody inhibits IP-10 induced calcium flux; (iii) the antibody inhibits IP-10 induced cell migration; (iv) the antibody cross-reacts with rhesus monkey IP-10; (v) the antibody does not cross-react with mouse IP-10; (vi) the antibody does not cross-react with human MIG; (vii) the antibody does not cross-react with human ITAC. Homologous anti-IP-10 antibodies are also described in U.S. Publication No. 2005/0191293, the content of which is expressly incorporated by reference.

As defined herein, anti-IP-10 antibodies also include an anti-IP-10 antibody or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins". A cytotoxin or cytotoxic agent includes any agent that is detrimental to (e.g., kills) cells. Examples include TAXOL®, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (MYLOTARG®; Wyeth-Ayerst) Immunoconjugates of anti-IP-10 antibodies are also described in U.S. Publication No. 2005/0191293, the content of which is expressly incorporated by reference.

As defined herein, anti-IP-10 antibodies further include bispecific molecules comprising an anti-IP-10 antibody or a fragment thereof. An anti-IP-10 antibody or antigen-binding portions thereof, can be derivatized or linked to another functional molecule, e.g., another peptide or protein (e.g., another antibody or ligand for a receptor) to generate a bispecific molecule that binds to at least two different binding sites or target molecules. An anti-IP-10 antibody or a fragment thereof may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, an anti-IP-10 antibody can be functionally linked (e.g., by chemical coupling, genetic fusion, noncovalent association or otherwise) to one or more other binding molecules, such as another antibody, antibody fragment, peptide or binding mimetic, such that a bispecific molecule results. Bispecific anti-IP-10 antibodies are also described in U.S. Publication No. 2005/0191293, the content of which is expressly incorporated by reference.

Methods of Treating IP-10-Related Disorders

In certain aspect, the present invention relates to use of anti-IP-10 antibodies (including immunoconjugates and bispecific molecules) for treating IP-10-related disorders in subjects. The term "subject" as used herein in intended to include human and non-human animals. Non-human animals include all vertebrates, e.g., mammals and non-mammals, such as non-human primates, sheep, dogs, cats, cows, horses, chickens, amphibians, and reptiles. The methods are particularly suitable for treating human patients having a disorder associated with aberrant IP-10 expression. When antibodies to IP-10 are administered together with another agent, the two can be administered in either order or simultaneously.

The term "IP-10-related disease or disorder" or "IP-10-mediated disease or disorder" refers to a local and/or systemic physiological disorder where IP-10 is a primary mediator leading to the manifestation of the disorder. An exemplary IP-10-related disorder is an inflammatory or autoimmune disease, including but not limited to, multiple sclerosis, rheumatoid arthritis, inflammatory bowel disease (e.g., ulcerative colitis, Crohn's disease), systemic lupus erythematosus, Type I diabetes, inflammatory skin disorders (e.g., psoriasis, lichen planus), autoimmune thyroid disease (e.g., Graves' disease, Hashimoto's thyroiditis), Sjögren's syndrome, pulmonary inflammation (e.g., asthma, chronic obstructive pulmonary disease, pulmonary sarcoidosis, lymphocytic alveolitis), transplant rejection, spinal cord injury, brain injury (e.g., stroke), neurodegenerative diseases (e.g., Alzheimer's disease, Parkinson's disease), gingivitis, gene therapy-induced inflammation, diseases of angiogenesis, inflammatory kidney disease (e.g., IgA nephropathy, membranoproliferative glomerulonephritis, rapidly progressive glomerulonephritis) and atherosclerosis. IP-10-related disorders are also described in U.S. Publication No. 2005/0191293, the content of which is expressly incorporated by reference.

Pharmaceutical Compositions and Routes of Administration

In certain aspect, the present invention relates to a composition (e.g., a pharmaceutical composition) containing one or a combination of anti-IP-10 monoclonal antibodies or antigen-binding portion(s) thereof, formulated together with a pharmaceutically acceptable carrier. Such compositions may include one or a combination of (e.g., two or more different) antibodies, or immunoconjugates or bispecific molecules of the invention. For example, a pharmaceutical composition can comprise a combination of antibodies (or immunoconjugates or bispecifics) that bind to different epitopes on the target antigen or that have complementary activities. Optionally, the present invention provides combination therapy by using a pharmaceutical composition which comprises an anti-IP-10 antibody combined with other agents. For example, the combination therapy can include an anti-IP-10 antibody combined with at least one other anti-inflammatory or immunosuppressant agent. Examples of therapeutic agents that can be used in combination therapy are described in greater detail in U.S. Publication No. 2005/0191293, the content of which is expressly incorporated by reference.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound. The pharmaceutical compounds may include one or more pharmaceutically acceptable salts. Other ingredients of the pharmaceutical compositions are described in greater detail in U.S. Publication No. 2005/0191293, the content of which is expressly incorporated by reference.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of an anti-IP-10 antibody calculated to produce the desired therapeutic effect in association with the required pharmaceutical carrier. The specification for the dosage unit forms are dictated by and directly dependent on (a) the unique characteristics of the anti-IP-10 antibody and the particular therapeutic effect to be achieved, and (b) the limitations inherent in the art of compounding such an anti-IP-10 antibody for the treatment of sensitivity in individuals.

For administration of an anti-IP-10 antibody, the dosage ranges from about 1 to 50 mg/kg of the host body weight. For example, dosages can be 1 mg/kg, 3 mg/kg, 5 mg/kg, 10 mg/kg, 15 mg/kg, 20 mg/kg, 25 mg/kg, 30 mg/kg, 35 mg/kg, 40 mg/kg, 45 mg/kg or 50 mg/kg, of body weight. An exemplary treatment regime entails administration once per day, three times per week, twice per week, once per week, once every two weeks, once every three weeks, once every four weeks, once per month, once every 3 months or once every three to 6 months. In an example, dosage regimens for an anti-IP-10 antibody include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In a specific embodiment, administration of an anti-IP-10 antibody is by intravenous infusion during the induction phase, and by subcutaneous injection during the maintenance phase. The frequency of administration may vary from once per day to once per month. If a subject fails to maintain response (also referred to as "lose response" or "relapse") during the maintenance phase, a diagnostic assay will be used to measure the subject's exposure level (e.g., blood level) of the anti-IP-10 antibody; (3) if the exposure level of the anti-IP-10 antibody is below a threshold exposure level, escalating the dosage in the subject. Optionally, the dosage can be escalated in the subject by increasing the frequency of administration (e.g., increasing the frequency from once a week to twice a week).

In some embodiments, two or more monoclonal antibodies with different binding specificities are administered simultaneously, in which case the dosage of each antibody administered falls within the ranges indicated. An anti-IP antibody is usually administered on multiple occasions. Intervals between single dosages can be, for example, weekly, monthly, every three months or yearly. Intervals can also be irregular as indicated by measuring blood levels of an IP-10 antibody in the patient. In certain aspects, dosage is adjusted to achieve a plasma concentration of about 1-600 µg/ml and in some methods about 25-300 µg/ml.

Alternatively, an anti-IP-10 antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of an anti-IP-10 antibody in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the anti-IP-10 antibody employed, or the ester, salt or amide thereof, the route of administration, the time of administration, the rate of excretion of the anti-IP-10 antibody being employed, the duration of the treatment, other drugs, compounds and/or materials used in combination with the particular compositions employed, the age, sex, weight, condition, general health and prior medical history of the patient being treated, and like factors well known in the medical arts.

In another embodiment, the present invention provides a composition comprising the anti-idiotypic antibody, or antigen-binding portion thereof, of the invention, and a pharmaceutically acceptable carrier.

The present invention is further illustrated by the following examples which should not be construed as further limiting. The contents of all figures and all references, patents and published patent applications cited throughout this application are expressly incorporated herein by reference.

Example 1

Exposure-Response Analysis of MDX-1100 in Patients with Ulcerative Colitis and Identification of Target Exposure to MDX-1100 for the Treatment of Patients with Ulcerative Colitis In a Phase II, double-blind, placebo-controlled, randomized, multicenter, multidose clinical Study, MDX-1100 was studied for the induction of clinical response in patients with moderate to severely active ulcerative colitis (UC) in comparison to placebo. Exposure-response (E-R) analyses of clinical data were conducted to identify a target exposure to MDX-1100 which would be safe and efficacious in treating UC patients.

Methods

1. Patient Population in E-R Analyses

A total of 109 patients with UC from 40 sites in 7 countries were randomized to receive either placebo (N=54) or MDX-1100 (N=55) at 10 mg/kg by intravenous infusion every other week for a total of 4 doses (Dose administered on Study Days 1, 15, 29, and 43).

The study was conducted in accordance with Good Clinical Practice, as defined by the International Conference on Harmonization and in accordance with the ethical principles underlying European Union Directive 2001/20/EC and the United States Code of Federal Regulations, Title 21, Part 50 (21 C.F.R. 50) and in accordance with the ethical principles that have their origin in the Declaration of Helsinki. The study protocol, amendments, and subject informed consent received appropriate approval by the Institutional Review Board (IRB)/Independent Ethics Committee (IEC) prior to initiation of study at the site. Prior to the beginning of the study, the investigator provided each subject with the IRB/IEC's written approval/favorable opinion of the written informed consent form and any other relevant information. Freely given written informed consent was obtained from each subject, or, in those situations where consent could not be given by the subject, their legally acceptable representatives, prior to study participation, including informed consent for any screening procedures conducted to establish subject eligibility in the study.

All patients had active UC defined as a Mayo score of 6 to 10 with moderate to severe active disease on endoscopy (Mayo endoscopic subscore of ≥2). All patients were on stable doses of 5-aminosalicylates (5-ASA), corticosteroids, azathioprine (AZA), and/or 6-mercaptopurine (6-MP).

These 109 patients were defined as the intent-to-treat (ITT) population and were the primary population for evaluating efficacy measurements. Of the 109 patients, 2 patients (both assigned to the placebo group) were randomized but did not receive treatment. Thus, the remaining 107 patients were defined as the Safety population and included all patients who received at least 1 full or partial dose of placebo (N=52) or MDX-1100 (N=55). Patient disposition and demographics are summarized in Tables 1 and 2.

TABLE 1

Patient Disposition (ITT Population)

| | No. of Patients, N (%) | | |
|---|---|---|---|
| | Placebo N = 54 | MDX-1100 N = 55 | Total N = 109 |
| ITT population | 54 (100.0) | 55 (100.0) | 109 (100.0) |
| Completed Day 57 | 49 (90.7) | 49 (89.1) | 98 (89.9) |
| Primary Reason for Discontinuation Before Day 57 | | | |
| Adverse event | 0 | 2 (3.6) | 2 (1.8) |
| Protocol violation | 1 (1.9) | 2 (3.6) | 3 (2.8) |
| Unsatisfactory therapeutic effect | 1 (1.9) | 0 | 1 (0.9) |
| Subject withdrew consent | 2 (3.7) | 0 | 2 (1.8) |
| Death | 0 | 0 | 0 |
| Lost to follow-up | 0 | 0 | 0 |
| Other | 1 (1.9) | 2 (3.6) | 3 (2.8) |

TABLE 2

Patient Demographics (ITT Population)

| | No. of Patients, N (%) | | |
|---|---|---|---|
| | Placebo N = 54 | MDX-1100 N = 55 | Total N = 109 |
| Age (years) | | | |
| Mean (SD) | 41.8 (14.2) | 44.7 (12.8) | 43.2 (13.5) |
| Median | 37.0 | 45.0 | 43.0 |
| Range | 18-75 | 25-73 | 18-75 |
| Sex, n (%) | | | |
| Male | 31 (57.4) | 37 (67.3) | 68 (62.4) |
| Female | 23 (42.6) | 18 (32.7) | 41 (37.6) |
| Race, n (%) | | | |
| White | 54 (100.0) | 53 (96.4) | 107 (98.2) |
| Black | 0 | 2 (3.6) | 2 (1.8) |
| Asian | 0 | 0 | 0 |
| Other | 0 | 0 | 0 |
| Weight (kg) | | | |
| Mean (SD) | 74.5 (18.1) | 81.9 (16.1) | 78.2 (17.4) |
| Median | 71.3 | 79.0 | 75.0 |
| Range | 50.0-139.1 | 52.0-124.1 | 50-139.1 |

2. Pharmacokinetic Analyses of MDX-1100 in Patients with UC

Serum samples for pharmacokinetic evaluation of MDX-1100 were taken from each patient up to 60 minutes prior to each dose on Study Days 1, 15, 29, and 43 and on Study Day 57. Serum concentrations of MDX-1100 were assayed using a validated ELISA assay method. Serum trough concentrations of MDX-1100 on Study Day 57 were derived as steady-state trough concentration (Cminss) for each patient received MDX-1100 treatment.

3. E-R Analyses of Efficacy and Safety Measurements and Identification of Target Exposure to MDX-1100

The exposure measurement assessed in E-R analyses was Cminss of MDX-1100 at Study Day 57. Efficacy measurements assessed in E-R analyses were: (1) Clinical response, which was defined as a decrease from baseline (screening) in the total Mayo score of at least 3 points and at least 30% in a patient at Study Day 57, with an accompanying decrease in the subscore for rectal bleeding of at least 1 point or an absolute subscore for rectal bleeding of 0 or 1 (the clinical response rate was defined as the proportion of patients in each treatment group who had a clinical response); (2) Clinical remission, which was defined as a total Mayo score of 2 points with no individual subscore exceeding 1 point and no blood in stool in a patient at Study Day 57 (the clinical remission rate was defined as the proportion of patients in each treatment group who were in clinical remission); and (3) Mucosal healing, which was defined as endoscopy subscore of 0 or 1 in a patient at Study Day 57 (the mucosal healing rate was defined as the proportion of patients in each treatment group who had mucosal healing). Safety measurements assessed in E-R analyses were death, serious adverse events (SAEs), treatment-related SAEs, discontinuation due to SAEs, adverse events (AEs), treatment-related AEs, and discontinuation due to AEs.

For E-R analyses, all ITT patients who had Cminss values of MDX-1100 on Study Day 57 were stratified into tertiles based on their Cminss values: (1) low (26.4-78.6 µg/mL); (2) mid (79.2-105 µg/mL); and top (108-235 µg/mL). Clinical response, clinical remission, and mucosal healing rates were calculated for each of Cminss tertiles, and 95% CIs were provided using Fisher's exact method. Logistic regression was used to study the exposure-response relations between the Cminss and each of the efficacy measures separately. Odds ratios associated with a doubling of the exposure along with their 95% CIs were calculated. P-values were also reported. Safety measurements were tabulated for all patients who received placebo, all patients who received MDX-1100, and all patients who received MDX-1100 and whose Cminss were in the highest tertile (≥108 µg/mL).

4. Identification of Target Exposure to MDX-1100 for the Treatment of Patients with UC The optimal target exposure to MDX-1100 was chosen to give the maximum separation between the patients whose exposure is less than the target exposure and the patients whose exposure is greater than the target exposure in terms of overall efficacy. The target exposure to MDX-1100 was determined based on the following algorithm—for any given exposure c, a Fisher's exact test was performed to determine if there is a difference between patients whose exposure is less than c and patients whose exposure is greater than c for clinical response, clinical remission and mucosal healing rate. The exposure with the minimum corresponding p-value was selected as the target exposure.

Results

1. Pharmacokinetics of MDX-1100 in Patients with UC

All reported concentrations of MDX-1100 in human serum by ELISA were generated in analytical runs using appropriate calibration curves and quality control samples that met pre-established acceptance criteria and were conducted in compliance with applicable SOPs in place at the time of analysis. A summary of the assay performance is shown in Table 3.

TABLE 3

Summary of Assay and Performance for MDX-1100 in Human Serum

| Analyte | LLOQ (μg/mL) | ULOQ (μg/mL) | Between-run % CV[a] | Mean % Deviation from Nominal Concentration[a] |
|---|---|---|---|---|
| MDX-1100 | 1 | 40 | ≤12.6 | ±3.35 |

[a]Maximum value from analytical QCs.

After 4 doses, the trough concentrations (Cmin) of MDX-1100 increased from 42.2 μg/mL on Day 15 to 91.3 μg/mL on Day 57 (Table 4). The Cmin at Study Day 57 was considered as Cminss based on the half-life of MDX-1100 in human was approximately 8 days and the Q2 week dosing regimen. The coefficient of variation (CV %) of Cminss of MDX-1100 was 44.2% on Study Day 57 and was similar to other biologic therapy (see, e.g., Fasanmade, A. A. et al., *Int. J. Clin. Pharmacol. Ther.*, 48(5):297-308 (2010); Nestorov, I., *Semin. Arthritis Rheum.*, 34(5 Suppl. 1):12-8 Review (April 2005)).

TABLE 4

Summary Statistics of Cmin of MDX-1100 (μg/mL)

| Study Day | | 1 | 15 | 29 | 43 | 57 |
|---|---|---|---|---|---|---|
| Cmin[a] | Geo Mean | | 42.2 | 72.0 | 84.0 | 91.3 |
| | CV % | | 50.1 | 73.6 | 58.4 | 44.2 |
| | N | | 50 | 50 | 49 | 49 |

[a]Trough concentration collected at predose prior to the administration of the infusion dose.

2. Exposure-Response Relationship of Clinical Response, Clinical Remission, Mucosal Healing Rates Vs Cminss of MDX-1100

E-R analyses demonstrated that higher Cminss of MDX-1100 was associated with a marked increase in the clinical response, clinical remission, and mucosal healing rates (FIG. 1). Patients whose Cminss of MDX-1100 were in the highest tertile subgroup (Cminss: 108-235 μg/mL) achieved the highest clinical response, clinical remission, and mucosal healing rates compared with patients who received placebo treatment or patients whose Cminss of MDX-1100 were in the two lower tertiles. The clinical response, clinical remission, and mucosal healing rates were 87.5% vs. 37%, 43.8% vs. 18.5%, and 68.8% vs. 35.2% for patients who achieved Cminss of MDX-1100 in the highest tertile subgroup vs. patients who received placebo treatment, respectively. There was also a marked improvement in Mayo score in patients whose Cminss were in the highest tertile subgroup compared with patients treated with placebo or patients whose Cminss of MDX-1100 were in the two lower tertiles: mean decrease in Mayo score from baseline of 4.7 compared with 2.8.

Figure 2:
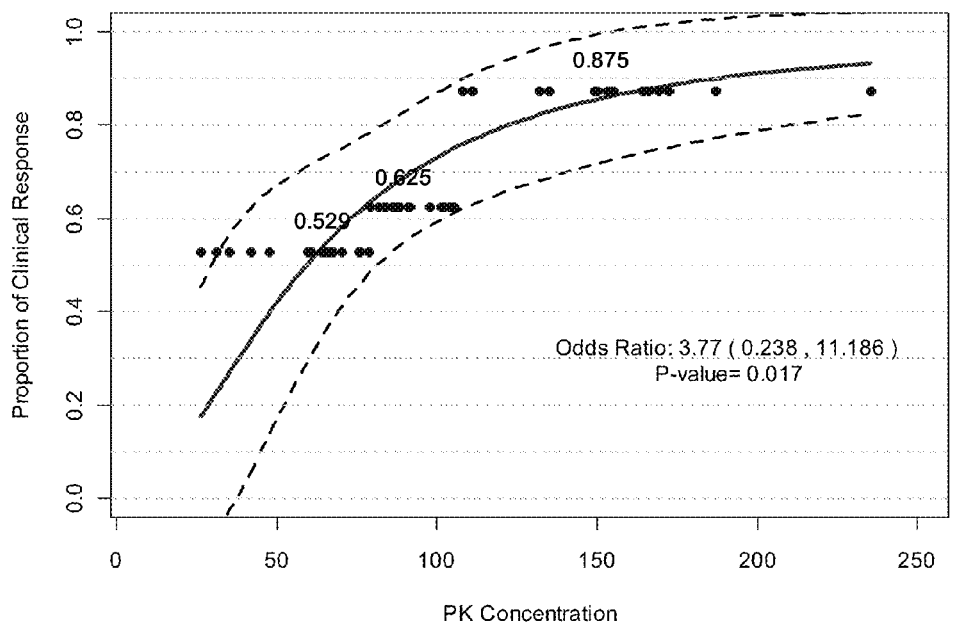
FIG. 2 shows logistic regression analysis of clinical response rate vs. Cminss of MDX-1100 at Study Day 57.
Figure 3:
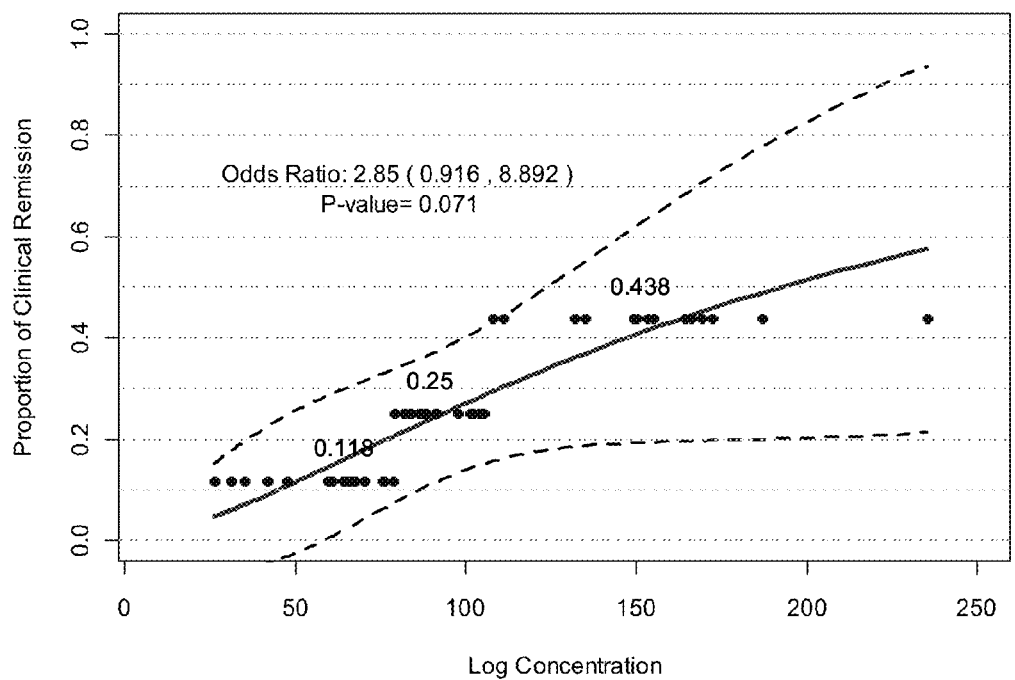
FIG. 3 shows logistic regression analysis of clinical remission rate vs. Cminss of MDX-1100 at Study Day 57.
Figure 4:
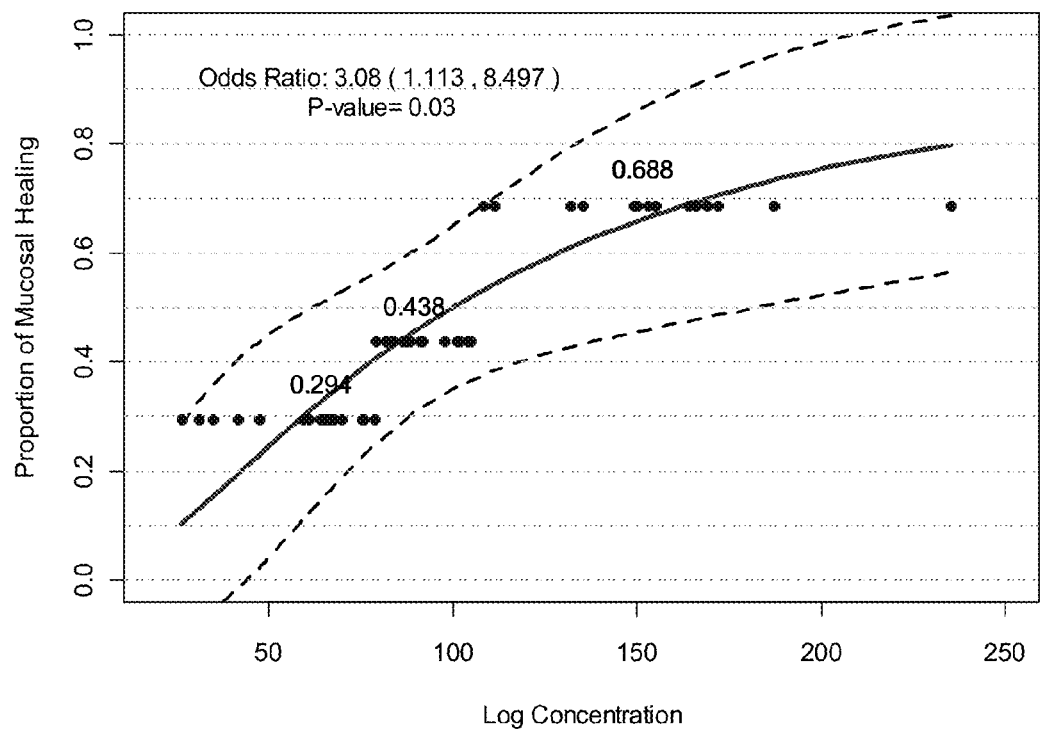
FIG. 4 shows logistic regression analysis of mucosal healing rate vs. Cminss of MDX-1100 at Study Day 57.

Logistic regression analyses of clinical response, clinical remission, and mucosal healing rates also demonstrated that, when patients with UC were treated with MDX-1100, patients would achieve increased clinical response, clinical remission, and mucosal healing rates if they achieved increased Cminss of MDX-1100. The odds ratios of clinical response, clinical remission, and mucosal healing rates were 3.77 (P=0.017), 2.85 (P=0.071), and 3.08 (P=0.03) respectively. In another word, if the Cminss of MDX-1100 achieved by patients increases by a factor of two, the odds for patients to achieve clinical response, clinical remission, and mucosal healing increases by 3.77, 2.85, and 3.08 times, respectively (FIGS. 2-4).

3. Exposure-Safety Relationship

The safety profile of patients treated with MDX-1100 and achieved Cminss in the highest tertile subgroup was comparable to the overall MDX-1100 safety population (Table 5). Six out of 16 patients (37.5%) whose Cminss of MDX-1100 were in the highest tertile subgroup experienced at least one AE compared with 22 out of 55 patients (40%) in the overall MDX-1100 Safety population. Only 2 out of these 16 patients (12.5%) experienced AEs were considered related to study therapy, compared with 11 out of 55 (20.0%) in the overall MDX-1100 Safety population. The number of patients whose Cminss of MDX-1100 were in the highest tertile subgroup and experiencing at least one AE was also comparable to that in the placebo group (6/16 [37.5%] vs. 17/52 [32.7%], respectively).

There were no SAEs reported for the 16 patients whose Cminss of MDX-1100 were in the highest tertile subgroup, compared to 4 patients (7.3%) in the overall MDX-1100 Safety population. The 2 patients in the overall MDX-1100 Safety population who were discontinued due to AEs were not in the highest tertile subgroup of Cminss. In addition, none of the patients with reported infections in the overall MDX-1100 Safety population (7 out of 55 patients, 12.7%) were in the highest tertile subgroup of Cminss.

In summary, based on a limited number of patients in this study, there was no increase in AEs associated with an increase in Cminss of MDX-1100.

TABLE 5

Summary of Adverse Events[a] (Cminss Subgroup)

| | No. of Patients, N (%) | | |
|---|---|---|---|
| | Placebo N = 52 | MDX-1100 Safety Population N = 55 | MDX-1100 Cminss ≥ 108 μg/mL Subgroup N = 16 |
| Death | 0 | 0 | 0 |
| SAEs[b] | 1 (1.9) | 4 (7.3) | 0 |
| Related SAEs[c] | 0 | 0 | 0 |
| Discontinued due to SAEs | 0 | 1 (1.8) | 0 |

TABLE 5-continued

Summary of Adverse Events[a] (Cminss Subgroup)

| | No. of Patients, N (%) | | |
|---|---|---|---|
| | Placebo N = 52 | MDX-1100 Safety Population N = 55 | MDX-1100 Cminss ≥ 108 μg/mL Subgroup N = 16 |
| AEs | 17 (32.7) | 22 (40.0) | 6 (37.5) |
| Related AEs | 7 (13.5) | 11 (20.0) | 2 (12.5) |
| Discontinued due to AEs | 0 | 2 (3.6) | 0 |

[a]AE is defined as a sign of symptom that emerges during treatment or within 70 days of the last dose of the treatment including having been absent pre-treatment or that has worsened relative to the pre-treatment state and any treatment-related AE regardless of timing.
[b]SAEs include all Grade 3 (severe) and above events (or events with missing severity) considered serious by the investigator up to 70 days post study drug. The Grade level is based on USA NCI AE clarification guideline.
[c]Possibly, probably, or definitely related to the study drug (missing relationships presumed as related).

4. Target Exposure to MDX-1100 for the Treatment of Patients with UC

Figure 5:
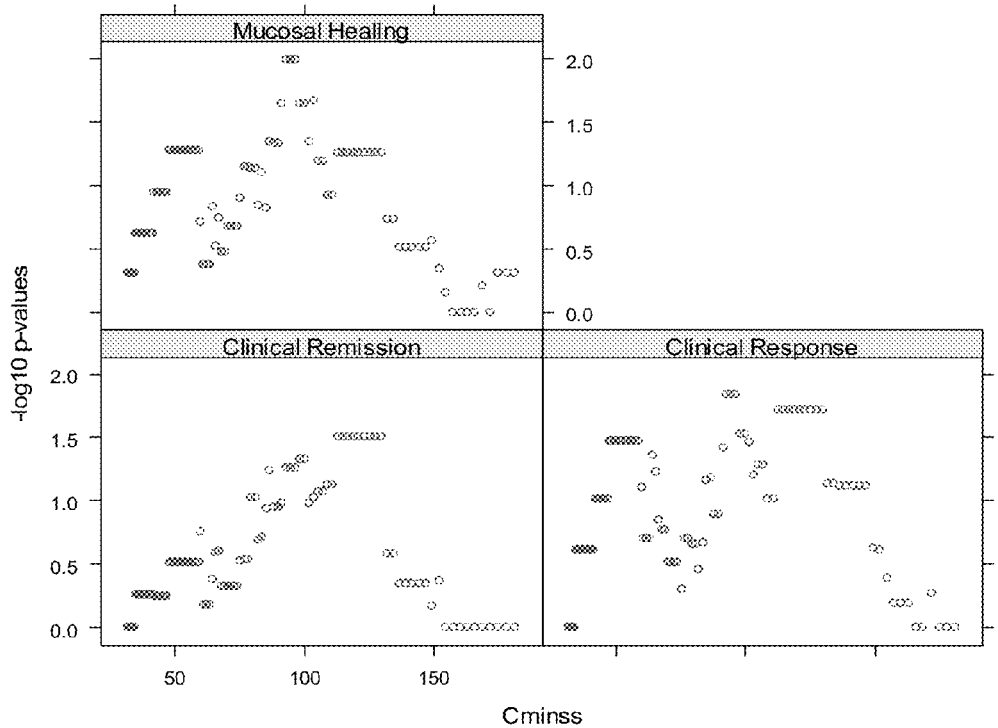
FIG. 5 shows the negative log 10 transformed p-values vs. different Cminss as possible target exposure.

All three efficacy measures (clinical response, clinical remission and mucosal healing rate) were used to identify the target exposure to MDX-1100. Based on the results in FIG. 5, at about Cminss of 100 μg/mL, the −log 10 transformed p-value achieved the maximum, which indicated minimum corresponding p-value thus a maximum efficacy separation between the patients whose exposure were greater than this target exposure and the patients whose exposure were less than this target exposure. Exposure-safety analyses suggested that MDX-1100 was safe and well tolerated in UC patients with Cminss in the highest tertile (108-235 μg/mL) in this study. Thus Cminss value of 100 μg/mL was identified as the target exposure to MDX-1100, which is safe and efficacious for the treatment of UC patients with MDX-1100.

5. Immunogenicity Analysis

In this study, immunogenicity assessment of MDX-1100 was conducted using samples from the safety population with a validated electrochemiluminescent (ECL) assay at Days 1, 29, 57, and 85 (42 days after last dose of study drug). Human anti-human antibodies against MDX-1100 was not detected in any patient with this ECL assay.

Example 2

Generation of Mouse Anti-MDX-1100 Idiotypic Antibodies

Materials and Methods

1. Immunogen

MDX-1100, also referred to herein as 6A5, is a human anti-IP-10 antibody (see, e.g., U.S. Publication No. 2005/0191293). MDX-1100 (10 mg/ml) was used for Fab preparation. Fab fragment of MDX-1100 (2.92 mg/ml) was used as an immunogen in antibody generation.

2. Mice and Immunization Procedure

The following mice were used to generate a few hybridomas, for example, 10C8, 6C9, 2F5, and 23H10. Table 6 below summarizes the hybridomas and the corresponding mice used in their production.

TABLE 6

A List of Hybridomas and the Corresponding Mice Used in Their Production

| Hybridoma | Mouse ID | Mouse Sex | Mouse Genotype |
|---|---|---|---|
| 10C8 | 135878 | Male | BALB/C |
| 6C9 | 135879 | Female | BALB/C |
| 2F5 | 222587 | Female | BALB/C |
| 23H10 | 222587 | Female | BALB/C |

About 25-30 ng Fab of MDX-1100 was used to immunize the mice through ip, sc, and foot pad injection. Such immunization was conducted on five separate days. Subsequently, spleen and lymph nodes were harvested.

3. Hybridoma Generation

The Sp2/0 myeloma cell line was used for the fusions. Cells were maintained in culture for 1 month, passed twice a week. Supernatant from P388D1 (ATCC, TIB-63 FL) cells was used as conditioned media for the hybridomas. Briefly, cells were grown and expanded to 200 mL. Stationary cultures were grown for about 7 days. The exhausted supernatant was spun down and filtered through a 0.2 μm sterile filter. This cell line was passed for 1 month and then a new vial was thawed.

DMEM (Gibco #12382-024) containing 10% FBS (HY-CLONE®, cat #SH30071.03; Lot #ASL31024) were used to culture the myeloma fusion partner and P388D1 cells. Additional media supplements were added to the Hybridoma growth media, which included 5% Origen—Hybridoma Cloning Factor (IGEN®, cat #210001), 15% P388D1 conditioned media, β-mercaptoethanol (Gibco cat #1019091), Hepes (CELLGRO® #25060037) and HAT (Sigma, H 0262; $1.0 \times 10^{-4}$ M Hypoxanthine, $4.0 \times 10^{-7}$ M Aminopterin, $1.6 \times 10^{-5}$ M Thymidine), or HT (Sigma, H0137; $1.0 \times 10^{-4}$ M Hypoxanthine, $1.6 \times 10^{-5}$ M Thymidine).

The viable cells yielded from the spleens and lymph nodes of the three mice for fusions were listed in Table 7 below. Electrode fusion was performed on the splenocytes. The resulting hybridomas were plated out into 96-well COSTAR® tissue-culture treated plates seeded at 200 μl/well.

TABLE 7

A List of Fusions Yielded from the Spleens and Lymph Nodes of Mice

| Fusion ID | Mouse ID | Total Splenocytes and Lymphocytes |
|---|---|---|
| 925 | 135878 | 1.8e8 |
| 926 | 135879 | 2.1e8 |
| 2431 | 222587 | 2.1e8 |

Results

1. Fusion Screening, Subcloning and Expansion

The fusions were screened for antibodies directly binding to MDX1100 6A5 (whole 6A5, 6A5-biotin, or 6A5 Fab) initially; then following up the specific binding vs. other anti-IP-10 human antibodies (e.g., 1D4 and 10A12), and pooled human IgG.

Figure 6A:
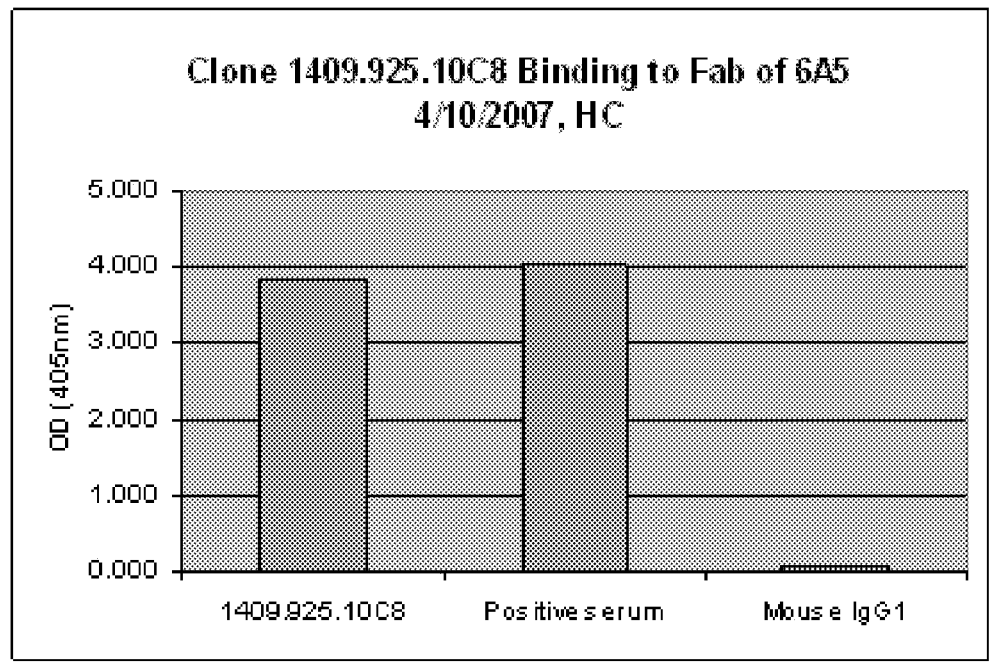
FIGS. 6A and 6B show analysis of binding activities of two anti-idiotypic Clones 10C8 and 6C9.
Figure 6A:
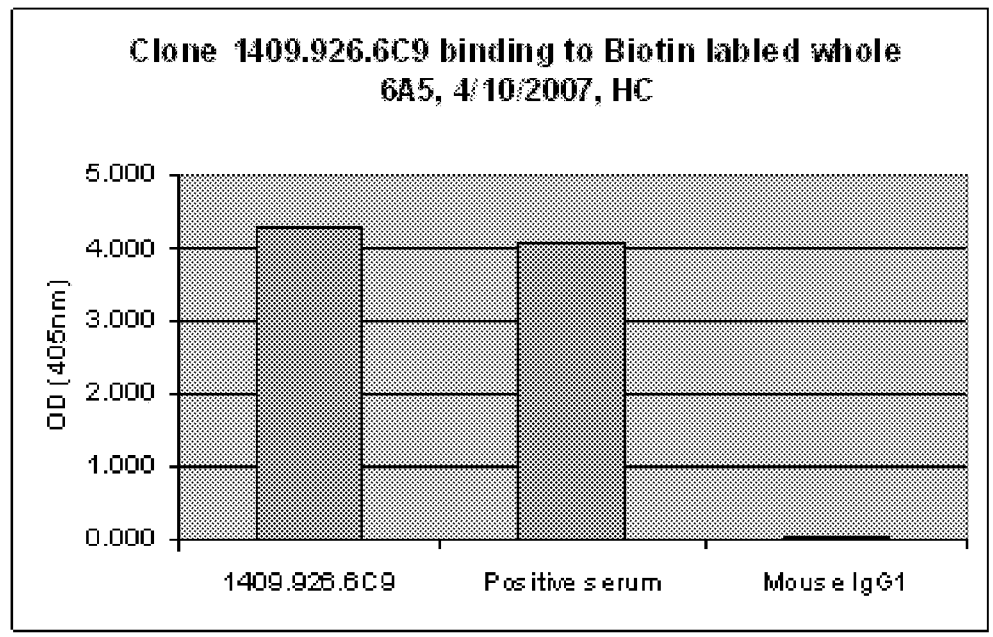
Figure 6B:
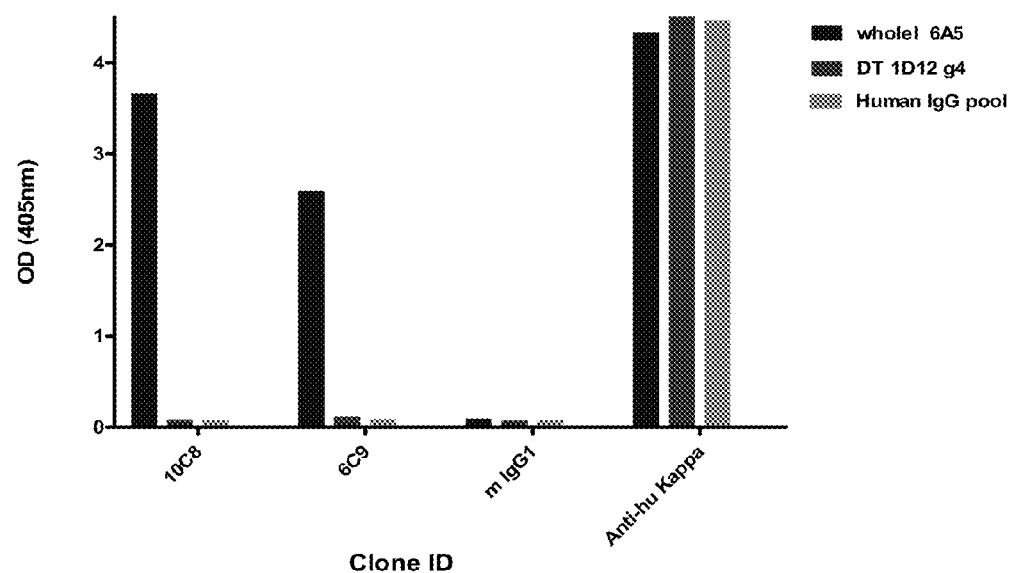
Figure 7:
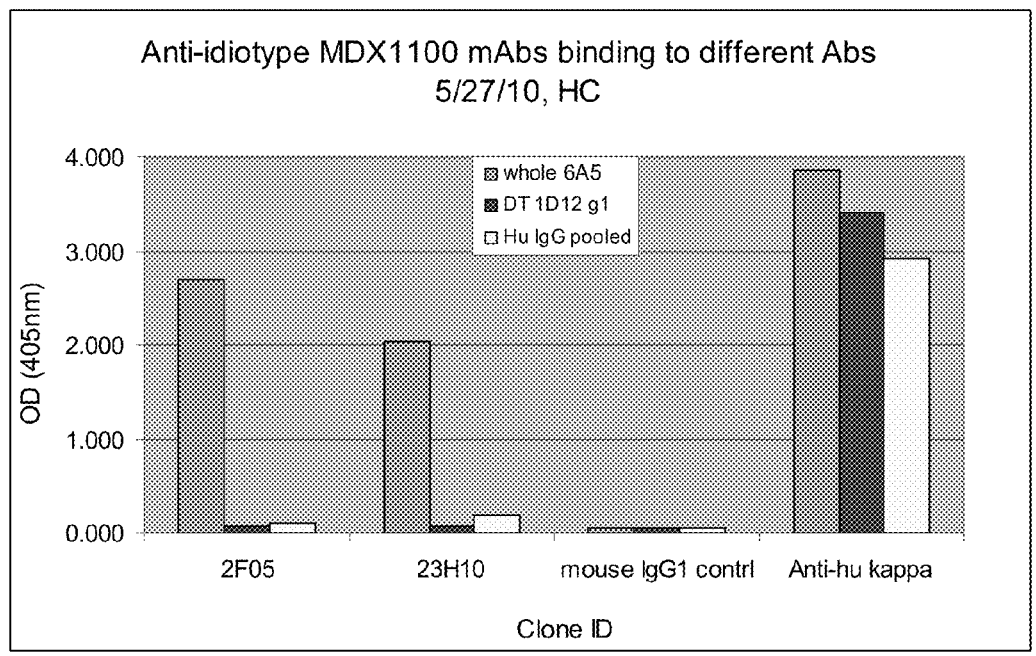
FIG. 7 shows analysis of binding activities of two anti-idiotypic Clones 2F5 and 23H10.

FIG. 6A shows that clones 10C8 and 6C9 were positive when hybridoma supernatant was screened for MDX1100 6A5 specific antibodies by ELISA. FIG. 6B shows that clones 10C8 and 6C9 bind to 6A5 specifically. FIG. 7 shows that clones 2F5 and 23H10 bind to 6A5 specifically.

Figure 8:
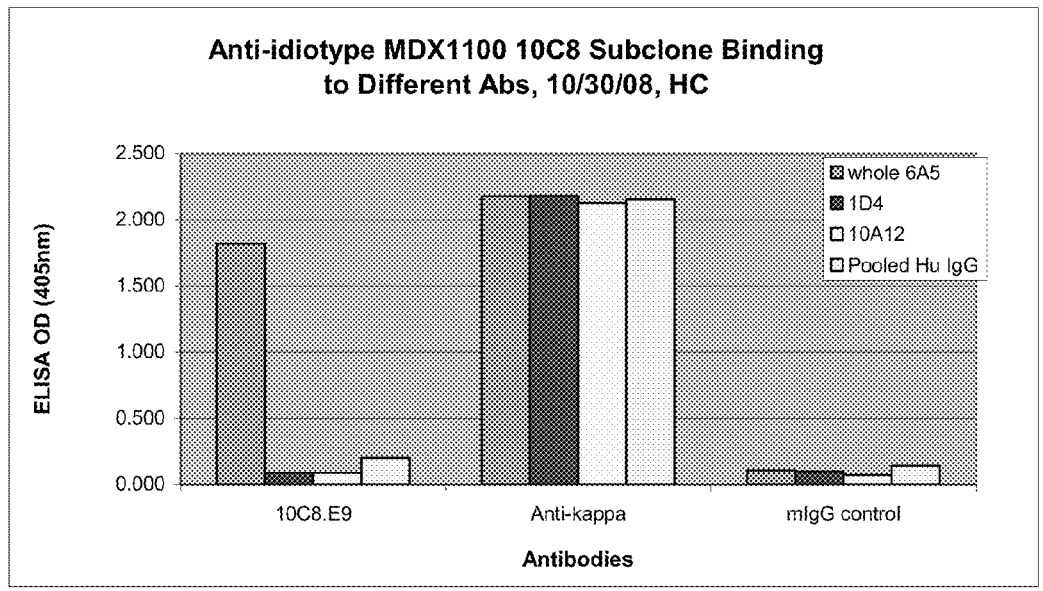
FIG. 8 shows analysis of binding activities of Subclone of 10C8.
Figure 9:
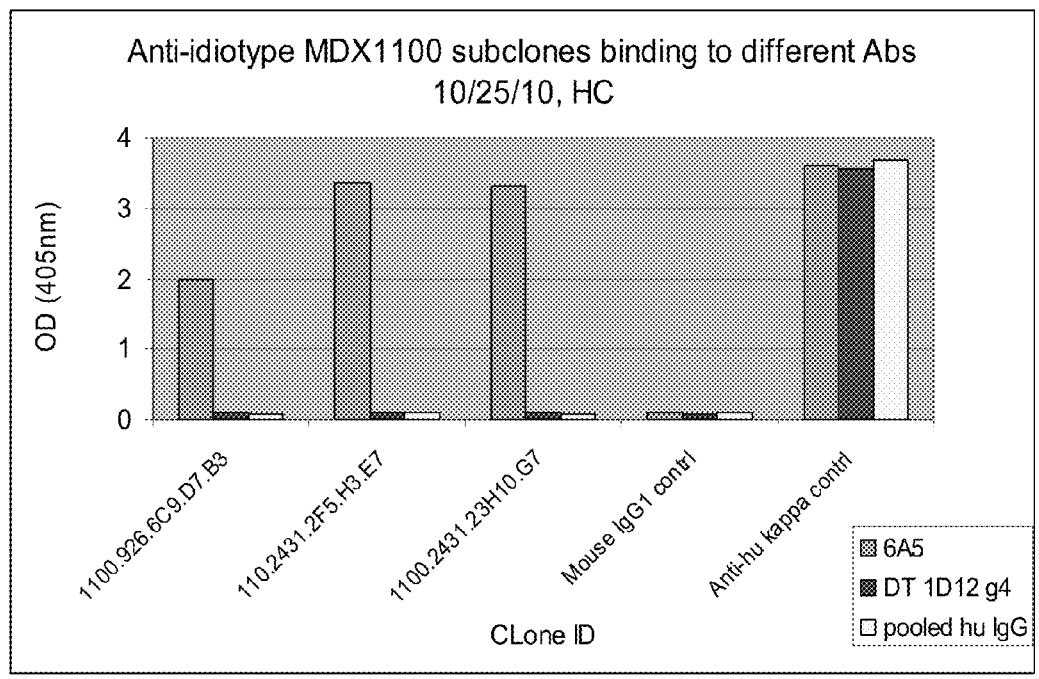
FIG. 9 shows analysis of binding activities of Subclones of 6C9, 2F5 and 23H10.

Furthermore, Subclones of 10C8, 6C9, 2F5, and 23H10 were similarly analyzed and found to bind to 6A5 specifically (FIGS. 8-9).

2. Antibody Selection

The antibody selection was based on direct binding to MDX1100 6A5, specific for 6A5 vs. irrelevant antibodies 1D4 and 10A12, and a pooled human IgG, and competition of anti-idiotypic antibodies with 6A5-IP-10 interaction. In the competitive binding assays on ELISA, 1 µg/ml, 50 µl of goat anti-mouse IgG gamma was coated on the plates. Pre-mixed 6A5 with IP-10 (antigen:antibody ratio=5:1) or whole 6A5 alone was added. 1 µg/ml, 50 µl of a diluted anti-idiotypic antibody was added as well. Then, goat anti-human IgG Fc gamma-HRP was added for detection.

Figure 10:
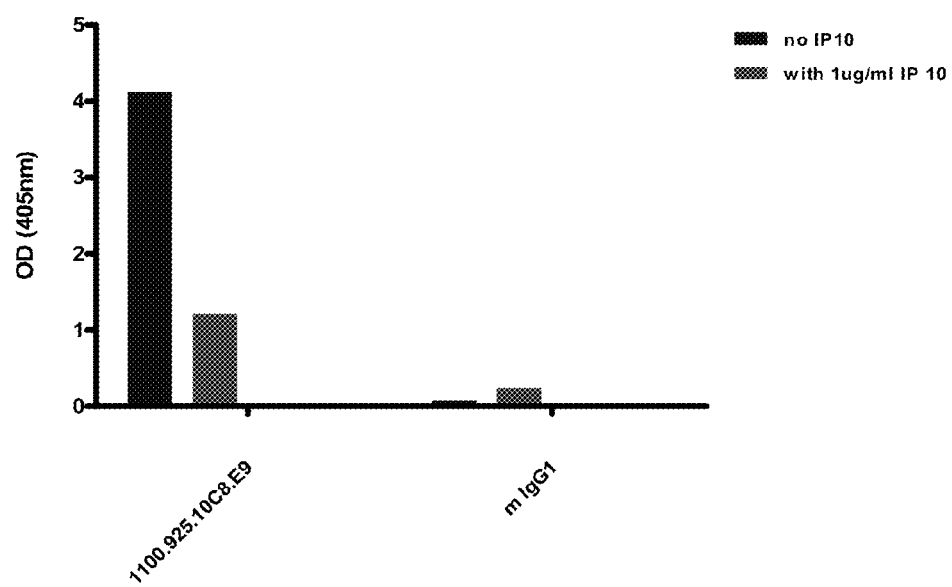
FIG. 10 shows analysis of binding activities of Clone 10C8 competition with IP-10.
Figure 11:
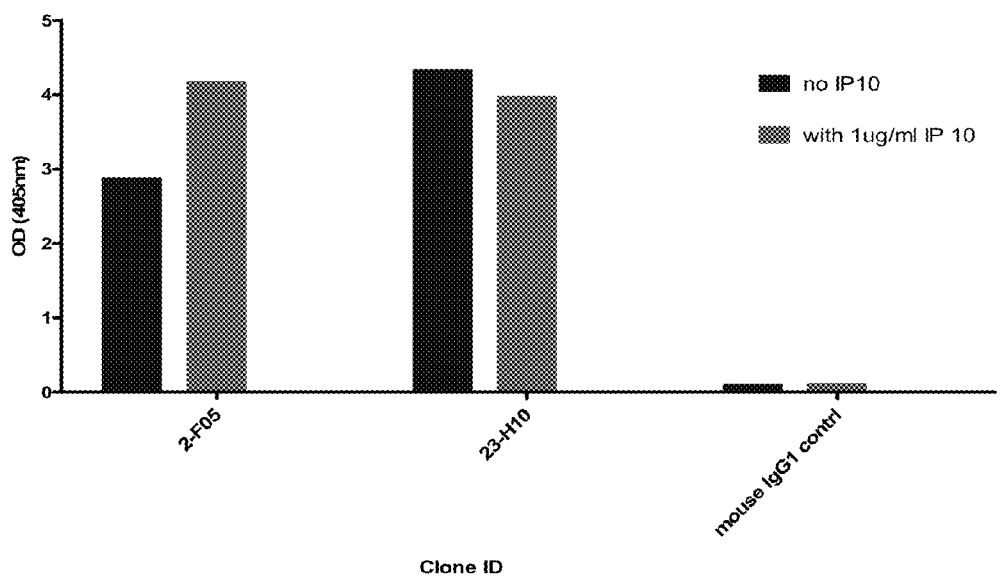
FIG. 11 shows analysis of binding activities of Clone 2F5 and 23H10 competition with IP-10.

FIG. 10 shows that Clone 10C8 competes with IP-10 in the competitive binding assays. FIG. 11 shows that Clones 2F5 and 23H10 do not compete with IP-10 in the competition binding assays.

Example 3

Quantitative Determination of MDX-1100 in Human Serum by Meso Scale Discovery (MSD) Electrochemiluminescence Immunoassay A Meso Scale Discovery (MSD) electrochemiluminescence immunoassay was developed for the quantitation of MDX-1100 in human serum. The MSD method employed a technique in which biotinylated anti-MDX-1100 mouse monoclonal antibody (clone 10C8) was coated onto a streptavidin coated 96-well plate to capture MDX-1100 in 2% human serum. The captured MDX-1100 was then detected using sulfo-tag labeled anti-MDX-1100 mouse monoclonal antibody (clone 23H10). The standard curve, prepared in 2% human serum, ranged from 5 ng/mL to 300 ng/mL (250 to 15,000 ng/mL in 100% human serum), and was fitted to a 4-parameter logistic regression model with 250 ng/mL as an anchor point. The intra-assay precision for QCs was within 7.2% and inter-assay precision was within 10.9%. The intra-assay precision for reference standards was within 6.7% and inter-assay precision was within 6.4%. The QCs accuracy was within ±15.6% of the nominal values. The reference standards accuracy was within ±5.4% of the nominal values. At the lower limit of quantitation (LLOQ) of 500 ng/mL, the deviation of the predicted concentrations from the nominal value for ten out of ten ulcerative colitis patient serum samples was within ±6.7%. The assay performance was not affected by preincubated IP-10 and heparan sulfate up to 100 ng/mL and 5000 ng/mL, respectively, but 35-40% interference was observed with 1000 ng/mL of IP-10 and 50000 ng/mL of heparan sulfate in HQC, MQC and LQC. Recovery of MDX-1100 and isoAsp-MDX-1100 showed no differences.

Materials and Methods

A. Preparation of Solutions and Reagents

1. Assay Buffer (1% BSA and 0.05% TWEEN-20 in DPBS)

Displace 50 mL of 10% BSA solution and 2.5 mL of 10% TWEEN-20 solution into 500 mL of DPBS. Store at 2-8° C. Use within three month of preparation.

2. Blocking Buffer (5% BSA and 0.05% TWEEN-20 in DPBS):

Add 250 mL of 10% BSA solution and 2.5 mL of 10% TWEEN-20 solution into 250 mL of DPBS. Store at 2-8° C. Use within three month of preparation.

3. PBS Wash Buffer (PBS Dry Powder Packets, pH 7.4±0.2 Containing 0.05% v/v TWEEN-20)

Contents of one packet of PBS were dissolved in 1 liter dH$_2$O and the solution was stored at room temperature. Use within one month of preparation.

4. Assay Buffer/2% Human Serum

60 µL of human serum is added to 2940 µL of Assay Buffer. This solution is prepared on the day of use.

5. Biotinylated Mouse Anti-Idiotypic IP-10 6A5 MAb 10C8

Stored in aliquots at −70° C. Prior to use, each aliquot was thawed at room temperature. A final 1 µg/mL in assay buffer was prepared and used for the coating of plates for the assay. Each new lot of this reagent must be titrated against the previous lot and used in the assay at a dilution that gives results equivalent to those observed with the previous lot.

6. Sulfo-Tag Labeled Mouse Anti-Idiotypic IP-10 6A5 MAb 23H10

The reagent was aliquoted, and stored at −70° C. A final concentration of 25 ng/mL solution of the Sulfo-Tag labeled mouse anti-idiotypic IP-10 6A5 MAb 23H10 in assay buffer was prepared for the assay. Each new lot of this reagent must be titrated against the previous lot and used in the assay at a dilution that gives results equivalent to those observed with the previous lot.

7. MSD Read Buffer T (2×)

The reagent was stored in room temperature. A final 2× solution was prepared by diluting 5 mL of MSD Read Buffer T (4×) in 5 mL dIH$_2$O before use.

B. Preparation of Standards

1. Preparation of MDX-1100 Working Solutions

20 µL of the 0.99 mg/mL stock solution was added 178 µL of human serum to yield a solution containing 100 µg/mL. A further dilution of 50-fold in assay buffer was performed to yield a 2000 ng/mL solution in 2% human serum (working solution1), 2000 ng/mL solution was further diluted 20-fold in 2% human serum to 100 ng/mL (working solution 2). This working solution was used on the day of preparation. Excess solution was discarded.

2. Preparation of the Calibration Standard Curve in 2% Human Serum

The standard curve was prepared in assay buffer/2% human serum as described below.

Note: Volume is enough for one plate. Proportional volumes were prepared as needed.

TABLE 8

Calibration Standard Curve Preparation

| Nominal Conc. of MDX-1100 (ng/mL)* | Volume of Working Solution (µL) | Volume of Assay Buffer/ 2% Human Serum (µL) |
|---|---|---|
| 15000 | 30 (working solution 1) | 170 |
| 10000 | 20 (working solution 1) | 180 |
| 8000 | 16 (working solution 1) | 184 |
| 6000 | 12 (working solution 1) | 188 |
| 5000 | 200 (working solution 2) | 0 |
| 4000 | 160 (working solution 2) | 40 |
| 3000 | 120 (working solution 2) | 80 |
| 2000 | 80 (working solution 2) | 120 |
| 1000 | 40 (working solution 2) | 160 |
| 500 | 20 (working solution 2) | 180 |
| 250 | 10 (working solution 2) | 190 |

*The concentrations of MDX-1100 listed are in 100% human serum.

3. Preparation of Quality Control Samples (1) Preparation of MDX-1100 QC Samples in 100% Human Serum 20 µL of the 0.99 mg/mL MDX-1100 stock solution was diluted with 970 µL of human serum to yield a solution containing 20000 ng/mL. Appropriate dilutions of the 20000 ng/mL solution with human serum to yield QC samples of 15000, 10000, 6000, 1000 and 500 ng/mL (ULOQ, High, Medium, Low and LLOQ), were prepared. QC samples were stored in aliquots of 25 µL at −70° C.

TABLE 9

Quality Control Sample Preparation

| Sample | Conc. of MDX-1100 (ng/mL)* | Volume of 20000 ng/mL of MDX-1100 (µL) | Volume of 100% Human Serum (µL) |
|---|---|---|---|
| ULOQ | 15000 | 210 | 70 |
| HQC | 10000 | 150 | 150 |
| MQC | 6000 | 90 | 210 |
| LQC | 1000 | 20 | 380 |
| LLOQ | 5000 | 15 | 585 |

*The concentrations of MDX-1100 listed are in 100% human serum.

(2) Preparation of QC Samples (High, Medium, Low, LLOQ, and Dilution) in 2% Human Serum To prepare QC samples within the range of the assay and to the minimum required dilution of the assay, a 1:50 dilution of each of the QC samples was prepared by adding 10 µL of the 100% human serum QC samples, prepared supra, to 490 µL of assay buffer to provide QC samples containing 15000, 10000, 6000, 1000 and 500 ng/mL in 2% human serum. These dilutions were prepared on the day of the analysis.

4. Assay Procedure

Unless specified, all steps were performed at 22° C. on the shaker with a speed of 200 rpm. The plates were incubated covered unless otherwise noted.

1) 96-well streptavidin coated MSD plates were blocked with blocking buffer (5% BSA and 0.05% TWEEN-20 in DPBS) for at least 30 min at 22° C. on a shaker.

2) 50 µL of biotinylated 10C8 (1 µg/mL in assay buffer) was added to the plates. The plates were covered with plate sealer and incubated at 22° C. for 60±30 min on a shaker.

3) The plates were washed 3 times with 300 µL of PBST.

4) 50 µL of standards, QCs and samples in assay buffer/2% human serum buffer were added to the plates. The plates were incubated at 22° C. for 120±30 min on a shaker.

5) The plates were washed 3 times with 300 µL of PBST.

6) 50 µL of sulfo-tag 23H10 (25 ng/mL in assay buffer) was added to the plates. The plates were incubated for 60±30 min on a shaker.

7) The plates were washed 3 times with 300 µL PBST.

8) 150 µL of MSD Read Buffer T (2× in dIH$_2$O) was added. The plates were read on MSD Sector Imager 2400 within 10 minutes.

Results

1. Standard Curve Range

An eleven-point calibration standard curve ranging from 250 to 15000 ng/mL of MDX-1100 in 2% human serum was assayed in duplicate in each analytical run. The standard at 250 ng/mL is an anchor point and not subjected to acceptance criteria (data not shown).

2. Accuracy and Precision

The accuracy of the method was assessed by calculating the deviation of the predicted concentrations from their nominal values. The accuracy and precision information, based on the three analytical reference standards and QCs, obtained using a one-way ANOVA in SAS are listed in Tables 10 and 11. The intra-assay precision for QCs was within 7.2% and inter-assay precision was within 10.9%. The intra-assay precision for reference standards was within 6.7% and inter-assay precision was within 6.4%. The QCs accuracy was within ±15.6% of the nominal values. The reference standards accuracy was within ±5.4% of the nominal values.

TABLE 10

QC Accuracy and Precision for MDX-1100

| | Nominal Conc. | | | | |
|---|---|---|---|---|---|
| | LLOQ (500 ng/mL) | LQC (1000 ng/mL) | MQC (6000 ng/mL) | HQC (10000 ng/mL) | ULOQ (15000 ng/mL) |
| Mean Conc. Observed | 507.67 | 957.25 | 6935.21 | 10357.59 | 18008.13 |
| % Dev | 1.5 | −4.3 | 15.6 | 3.6 | 20.1 |
| Between Run Precision (% CV) | 7.7 | 10.9 | 1.9 | 0.0 | 4.8 |
| Within Run Precision (% CV) | 4.1 | 3.9 | 7.2 | 5.9 | 4.6 |
| Total Variation (% CV) | 8.7 | 11.6 | 7.5 | 5.9 | 6.7 |
| n | 17 | 18 | 18 | 18 | 20 |
| Number of Runs | 5 | 5 | 5 | 5 | 5 |

Concentration ng/mL in 100% human serum.

TABLE 11

Reference Standard Accuracy and Precision for MDX-1100

| Nominal Conc. ng/mL | 250 | 500 | 1000 | 2000 | 3000 | 4000 | 5000 | 6000 | 8000 | 10000 | 15000 |
|---|---|---|---|---|---|---|---|---|---|---|---|
| Mean Conc. Observed | 322.79 | 500.26 | 946.44 | 1910.46 | 3027.34 | 4179.29 | 4989.81 | 5876.65 | 7966.40 | 10053.42 | 15009.72 |
| % Dev | 29.1 | 0.1 | −5.4 | −4.5 | 0.9 | 4.5 | −0.2 | −2.1 | −0.4 | 0.5 | 0.1 |
| Between Run Precision (% CV) | 19.9 | 0.0 | 6.4 | 4.3 | 0.0 | 2.6 | 2.7 | 3.4 | 0.0 | 0.0 | 0.0 |
| Within Run Precision (% CV) | 2.7 | 6.7 | 2.0 | 1.5 | 3.1 | 2.6 | 2.6 | 3.4 | 3.0 | 2.5 | 2.5 |
| Total Variation (% CV) | 20.1 | 6.7 | 6.7 | 4.6 | 3.1 | 3.9 | 3.7 | 4.8 | 3.0 | 2.5 | 2.5 |
| n | 13 | 14 | 14 | 14 | 14 | 14 | 14 | 14 | 14 | 14 | 14 |
| Number of Runs | 7 | 7 | 7 | 7 | 7 | 7 | 7 | 7 | 7 | 7 | 7 |

Concentration ng/mL in 100% human serum.

2. Selectivity and Matrix Interference

Selectivity and matrix interferences in the method were evaluated with ten individual ulcerative colitis patient serum. Each matrix lot was run in the assay, both unspiked and spiked, at the 500 ng/mL (LLOQ). The unspiked matrix lots all quantitated below the level of quantitation, while the backcalculated concentrations of the 10 spiked matrix lots were all within 6.7% of LLQC. Table 12 shows that there are no matrix interferences observed in this assay.

TABLE 12

Selectivity/Matrix Interference of 10 Ulcerative Colitis Patient Serum Lot

| | Spiked with 500 ng/mL Drug | | | | | No Spiking | | |
|---|---|---|---|---|---|---|---|---|
| Patient serum lot | RLU | Backcalculated Conc. (ng/mL) | Mean value | % Dev | | RLU | Mean RLU | % Dev with Matrix blank |
| UC 1 | 452 | 504.16 | 489.35 | −2.1 | | 92 | 91.00 | −16.7 |
|  | 402 | 474.53 |  |  | | 90 |  |  |
| UC 2 | 520 | 544.04 | 533.51 | 6.7 | | 115 | 116.00 | 6.2 |
|  | 484 | 522.99 |  |  | | 117 |  |  |
| UC 3 | 430 | 491.16 | 499.14 | −0.2 | | 103 | 100.50 | −8.0 |
|  | 457 | 507.11 |  |  | | 98 |  |  |
| UC 4 | 453 | 504.75 | 525.56 | 5.1 | | 95 | 95.00 | −13.0 |
|  | 524 | 546.37 |  |  | | 95 |  |  |
| UC 5 | 455 | 505.93 | 510.05 | 2.0 | | 82 | 87.00 | −20.4 |
|  | 469 | 514.18 |  |  | | 92 |  |  |
| UC 6 | 402 | 474.53 | 475.12 | −5.0 | | 80 | 86.00 | −21.3 |
|  | 404 | 475.72 |  |  | | 92 |  |  |
| UC 7 | 439 | 496.49 | 495.01 | −1.0 | | 89 | 89.00 | −18.5 |
|  | 434 | 493.53 |  |  | | 89 |  |  |
| UC 8 | 427 | 489.38 | 498.54 | −0.3 | | 93 | 93.50 | −14.4 |
|  | 458 | 507.70 |  |  | | 94 |  |  |
| UC 9 | 472 | 515.94 | 526.19 | 5.2 | | 107 | 106.00 | −3.0 |
|  | 507 | 536.45 |  |  | | 105 |  |  |
| UC 10 | 493 | 528.26 | 528.26 | 5.7 | | 116 | 118.00 | 8.0 |
|  |  |  |  |  | | 120 |  |  |
| LLOQ | 478 | 519.46 | 513.87 | 2.8 | Matrix blank | 106 | 109.25 | NA |
|  | 488 | 525.33 |  |  | | 110 |  |  |
|  | 457 | 507.11 |  |  | | 115 |  |  |
|  | 451 | 503.57 |  |  | | 106 |  |  |

TABLE 13

Linearity of Dilution of MDX-1100

Run 17

| Nominal Conc. mg/mL | Dilution Factor | Mean Conc. Observed | % Dev |
|---|---|---|---|
| 2.5 | 500 | >ULOQ | |
| 2.5 | 5,000 | >ULOQ | |
| 2.5 | 50,000 | 2.25 | 10% |
| 2.5 | 500,000 | <LLOQ | |
| 2.5 | 5,000,000 | <LLOQ | |

3. Linearity of Dilutions in Human Serum

Dilutional linearity of MDX-1100 was assessed by diluting a 2.5 mg/mL QC sample at 50-fold with assay buffer first, then serially diluting 10-fold in assay buffer/2% human serum. These individual dilutions were analyzed with a standard curve and QC samples. The results, summarized in Table 13, indicated that the predicted concentrations of the individually diluted test samples were within ±10% of the nominal value. The data demonstrated that study samples could be diluted at least 50,000-fold in assay buffer/2% human serum without adversely affecting the accuracy and precision of the assay.

4. Specificity

IP-10 and Heparan Sulfate were combined at the following concentrations and used to test the potential inference with the quantitation of the low, mid and high QCs: (a) IP-10 at 0, 10, 100, 1000 ng/ml; and (b) Heparan Sulfate at 0, 500, 5000, 50000 ng/ml.

Each potential interfering reagent combination was tested in matrix blank, HQC, MQC and LQC. Samples were incubated for 1 hour at room temperature. The results, summarized in Table 14, showed that while spiking with 50000 ng/mL heparan sulfate+1000 ng/mL IP-10, all of the QCs showed more than 25% differences compared with non-spiked; while spiking with 5000 ng/mL heparan sulfate+100 ng/mL IP-10 as well as 500 ng/mL heparan sulfate+10 ng/mL IP-10, all of the QCs showed less than 14.5% differences compared with non-spiked QCs the percent of the difference between spiked and non-spiked.

TABLE 14

Specificity of MDX-1100

|  | HQC 10,000 ng/mL | | MQC 6,000 ng/mL | | LQC 1,000 ng/mL | | Matrix Blank | |
| --- | --- | --- | --- | --- | --- | --- | --- | --- |
|  | Mean Conc. Observed | % Dev | Mean Conc. Observed | % Dev | Mean Conc. Observed | % Dev | Mean Conc. Observed | % Dev |
| No interference | 18910 | NA | 11464 | NA | 1078 | NA | 92 | NA |
| 50000 ng/mL heparan sulfate + 1000 ng/mL IP-10 | 12211 | −35.4 | 6840 | −40.3 | 690 | −36.0 | 89 | −3.0 |
| 5000 ng/mL heparan sulfate + 100 ng/mL IP-10 | 16652 | −11.9 | 9798 | −14.5 | 956 | −11.3 | 89 | −3.3 |
| 500 ng/mL heparan sulfate + 10 ng/mL IP-10 | 19155 | 1.3 | 11454 | −0.1 | 1026 | −4.8 | 94 | 2.2 |

Concentration ng/mL in 100% human serum

5. IsoAsp-MDX-1100 Recovery

Since isomerization occurs in MDX-1100 at 6% rate yearly, recovery of the assay was evaluated by comparing the freshly thawed MDX-1100 with purified isoAsp-MDX-1100 at 10000, 5000, 2500 ng/mL levels. The results, summarized in Table 15, showed that no differences of recovery were observed of two forms of drug at 3 levels.

To conclude, a specific, precise and accurate MSD immunoassay for the quantitation of MDX-1100 in human serum has been developed over the standard curve concentration ranging from 250 ng/mL to 15,000 ng/mL in neat human serum.

TABLE 15

Spike Recovery Comparison of MDX-1100 and IsoAsp-MDX-1100

|  | MDX-1100 | | IsoAsp-MDX-1100 | | |
| --- | --- | --- | --- | --- | --- |
| Drug conc. (ng/mL) | Mean conc. Observed (ng/mL) | % Recovery | Mean conc. Observed (ng/mL) | % Recovery | % Difference |
| 10,000 | 8705.66 | 87.1 | 8294.31 | 82.9 | −4.7 |
| 5,000 | 4220.66 | 84.4 | 4521.15 | 90.4 | 7.1 |
| 2,500 | 2250.96 | 90.0 | 2335.67 | 93.4 | 3.8 |

Example 4

An Enzyme-Linked Immunosorbent Assay (ELISA) for the Quantitative Determination of MDX-1100 in Normal Human Serum Method Description This enzyme-linked immunosorbent assay (ELISA) is designed to detect MDX-1100 in human serum. NeutrAvidin coated plates are coated with biotinylated anti-MDX-1100 mouse monoclonal antibody (clone 10C8) at a concentration of 1.5 µg/mL in Assay Buffer. Calibrators, controls and samples are diluted to the assay MRD (1:1000) in Assay Buffer and incubated on the plate to capture MDX-1100. The captured MDX-1100 is then detected using HRP-labeled anti-MDX-1100 mouse monoclonal antibody (clone 23H10) at a concentration of 0.25 µg/mL in Assay Buffer. TMB is added as the HRP substrate. Plates are read on the SPECTRAMAX® Plus plate reader after the addition of Stop Solution and the measured optical density (OD) is directly proportional to the concentration of the MDX-1100 on the plate.

Analyte concentrations are determined by interpolation from the standard curve, which has been fit using a five-parameter logistic regression model with a weighting factor of 1/response2. The minimum required sample volume is 10.0 µL. The MRD is 1:1000. The calibration range is 1.25 to 320 µg/mL with a quantification range of 2.5 µg/mL to 320 µg/mL. Samples are stored at approximately −80° C.

Linearity and Calibration Standards

Ten calibration standards were utilized for this validation study over a range of 1.25-320 µg/mL. The standard curve was fit with a five-parameter logistic equation, with a weighting factor of 1/response2. The goodness of fit was calculated to be 0.9972 from an average of 13 standard curves from acceptable runs.

Precision and Accuracy

Precision and accuracy was assessed by analyzing Quality Controls (QCs) with concentrations ranging from the Lower Limit of Quantitation (LLOQ) to the Upper Limit of Quantitation ULOQ). The following QC levels were analyzed: LLOQ (QC 4=2.50 µg/mL), back-up LLOQ (QC 5; 5.00 µg/mL), Low QC (QC 1; 7.50 µg/mL), Mid QC (QC 2; 120 µg/mL), High QC (QC 3; 200 µg/mL), back-up ULOQ (QC 6; 240 µg/mL) and ULOQ (QC 7; 320 µg/mL). Precision was expressed as the percent coefficient of variation (PCV) of each pool. Accuracy was expressed as the percent difference from theoretical (PDT). These formulas are shown below (see Formulas). All precision and accuracy values were rounded to the nearest whole number prior to assessing the acceptability of the data.

Percent Coefficient of Variation (PCV):

PCV=(Standard Deviation/Mean)×100

Percent Difference from Theoretical (PDT):

PDT=[100×((Mean Calculated Concentration−Theoretical Concentration)/Theoretical Concentration)]

Percent Difference:

Percent Difference=100×[|Value1−Value2|/((Value1+Value2)/2)]

Intra-Assay Precision and Accuracy in Normal Human Serum

Six sets of replicates (12 wells) of each QC level (QCs 1-7) were analyzed in individual runs to determine intra-assay precision and accuracy of each QC. To meet the acceptance criteria for precision, intra-assay samples for QCs 1-3 and 5-7 were expected to have overall PCV values≤20%, and QC 4 was expected to have an overall PCV value≤25%. To meet the acceptance criteria for accuracy, intra-assay samples for QCs1-3 and QCs 5-7 were expected have overall PDT values within ±20%, and QC 4 was expected to have an overall PDT value within ±25%.

Intra-assay precision and accuracy analyses were performed in runs 1JHX2 (QCs 1-3), 2JHX2 (QCs 4-6) and 6JHX2 (QC 7). The PCV values for the intra-assay samples at all QC levels were acceptable, ranging from 3% for QC 4 (LLOQ) to 14% for QC 5 (Back-up LLOQ). The PDT values for the intra-assay precision and accuracy samples for all QC levels also fell within the acceptance criteria, ranging from −8% (QC 7; ULOQ) to 13% (QC 1 and QC 2). These data are presented in Table 16.

Inter-Assay Precision and Accuracy in Normal Human Serum

Data from seven acceptable runs (1-6JHX2 and 8JHX2), each containing two replicates of each QC level (QC 1-7), were used to determine inter-assay precision and accuracy. To meet precision criteria, inter-assay samples for QCs 1-3 and QCs 5-7 were expected to have overall PCV values≤20%, and QC 4 was expected to have an overall PCV value≤25%. The PCV values at all QC levels were acceptable, ranging from 9% (QC 2 and QC 3) to 14% (QC 5). To meet acceptance criteria for accuracy, inter-assay samples for QCs 1-3 and QCs 5-7 were expected to have PDT values within ±20%, and QC 4 was expected to have PDT values within ±25%. The PDT values for all QC levels were acceptable, ranging from −3% (QC 1 and QC 7) to 2% (QC 2 and QC 3). These data for Inter-Assay Precision and Accuracy are presented in Table 17. A complete list of data for QCs 1-7 from all validation runs using the validation calibrators and QCs is provided in Table 18.

TABLE 16

Intra-Assay Precicison and Accuracy Data

| Run ID | QC 1 (µg/mL) | QC 2 (µg/mL) | QC 3 (µg/mL) | QC 4 (µg/mL) | QC 5 (µg/mL) | QC 6 (µg/mL) | QC 7 (µg/mL) |
|---|---|---|---|---|---|---|---|
| 1JHX2 | 7.34 | 112 | 201 | NRR | NRR | NRR | NRR |
|  | 8.49 | 140 | 242 | NRR | NRR | NRR | NRR |
|  | 8.77 | 137 | 193 | NRR | NRR | NRR | NRR |
|  | 9.13 | 153 | 198 | NRR | NRR | NRR | NRR |
|  | 8.56 | 137 | 233 | NRR | NRR | NRR | NRR |
|  | 8.70 | 135 | 243 | NRR | NRR | NRR | NRR |
| 2JHX2 | NRR | NRR | NRR | 2.85 | 3.72 | 255 | NRR |
|  | NRR | NRR | NRR | 2.75 | 5.16 | 258 | NRR |
|  | NRR | NRR | NRR | 2.75 | 4.67 | 235 | NRR |
|  | NRR | NRR | NRR | 2.59 | 4.27 | 254 | NRR |
|  | NRR | NRR | NRR | 2.69 | 5.21 | 267 | NRR |
|  | NRR | NRR | NRR | 2.80 | 5.35 | 274 | NRR |
| 6JHX2 | NRR | NRR | NRR | NRR | NRR | NRR | 267 |
|  | NRR | NRR | NRR | NRR | NRR | NRR | 302 |
|  | NRR | NRR | NRR | NRR | NRR | NRR | 275 |
|  | NRR | NRR | NRR | NRR | NRR | NRR | 307 |
|  | NRR | NRR | NRR | NRR | NRR | NRR | 294 |
|  | NRR | NRR | NRR | NRR | NRR | NRR | 318 |

TABLE 16-continued

Intra-Assay Precicison and Accuracy Data

| Run ID | QC 1 (µg/mL) | QC 2 (µg/mL) | QC 3 (µg/mL) | QC 4 (µg/mL) | QC 5 (µg/mL) | QC 6 (µg/mL) | QC 7 (µg/mL) |
|---|---|---|---|---|---|---|---|
| N | 6 | 6 | 6 | 6 | 6 | 6 | 6 |
| Theoretical Concentration | 7.50 | 120 | 200 | 2.50 | 5.00 | 240 | 320 |
| Mean | 8.50 | 135 | 218 | 2.74 | 4.73 | 257 | 294 |
| S.D. | 0.611 | 13.4 | 23.4 | 0.0903 | 0.638 | 13.3 | 19.6 |
| PCV (%) | 7 | 10 | 11 | 3 | 14 | 5 | 7 |
| PDT (%) | 13 | 13 | 9 | 9 | −5 | 7 | −8 |

LEGEND:
NRR No Recorded Result
PCV Percent Coefficient of Variation
PDT Percent Difference from Theoretical

TABLE 17

QC Inter-Assay Data for Acceptable Validation Runs

| Run ID | QC 1 (µg/mL) | QC 2 (µg/mL) | QC 3 (µg/mL) | QC 4 (µg/mL) | QC 5 (µg/mL) | QC 6 (µg/mL) | QC 7 (µg/mL) |
|---|---|---|---|---|---|---|---|
| 1JHX2 | 7.12 | 115 | 210 | 2.29 | 5.69 | 228 | 303 |
|  | 8.56 | 136 | 243 | 2.84 | 6.15 | 314 | 394 |
| 2JHX2 | 6.94 | 129 | 219 | 2.69 | 5.31 | 205 | 304 |
|  | 7.64 | 129 | 207 | 2.85 | 5.65 | 244 | 329 |
| 3JHX2 | 7.95 | 119 | 190 | 2.65 | 5.32 | 232 | 314 |
|  | 7.81 | 121 | 214 | 2.97 | 5.80 | 262 | 366 |
| 4JHX2 | 8.44 | 136 | 210 | 2.87 | 5.32 | 213 | 275 |
|  | 7.43 | 114 | 214 | 2.46 | 5.62 | 250 | 330 |
| 5JHX2 | 7.02 | 145 | 170 | 2.28 | 4.15 | 221 | 266 |
|  | 6.36 | 110 | 203 | 2.28 | 3.98 | 259 | 297 |
| 6JHX2 | 6.80 | 121 | 182 | 1.92 | 4.29 | 242 | 290 |
|  | 7.39 | 120 | 195 | 2.22 | 4.45 | 248 | 282 |
| 8JHX2 | 6.91 | 118 | 197 | 2.25 | 4.46 | 204 | 293 |
|  | 5.38 | 106 | 197 | 2.45 | 4.46 | 247 | 299 |
| N | 14 | 14 | 14 | 14 | 14 | 14 | 14 |
| Theoretical Concentration | 7.50 | 120 | 200 | 2.50 | 5.00 | 240 | 320 |
| Mean | 7.27 | 123 | 204 | 2.5 | 5.05 | 241 | 310 |
| S.D. | 0.828 | 11 | 17.6 | 0.314 | 0.716 | 28.3 | 34.9 |
| PCV (%) | 11 | 9 | 9 | 13 | 14 | 12 | 11 |
| PDT (%) | −3 | 2 | 2 | 0 | 1 | 0 | −3 |

LEGEND:
PCV Percent Coefficient of Variation
PDT Percent Difference from Theoretical

TABLE 18

Inter-Assay Data for All Runs Using Validation QCs

| Run ID | QC 1 (µg/mL) | QC 2 (µg/mL) | QC 3 (µg/mL) | QC 4 (µg/mL) | QC 5 (µg/mL) | QC 6 (µg/mL) | QC 7 (µg/mL) |
|---|---|---|---|---|---|---|---|
| 1JHX2 | 7.12 | 115 | 210 | 2.29 | 5.69 | 228 | 303 |
|  | 8.56 | 136 | 243 | 2.84 | 6.15 | 314 | 394 |
| 2JHX2 | 6.94 | 129 | 219 | 2.69 | 5.31 | 205 | 304 |
|  | 7.64 | 129 | 207 | 2.85 | 5.65 | 244 | 329 |
| 3JHX2 | 7.95 | 119 | 190 | 2.65 | 5.32 | 232 | 314 |
|  | 7.81 | 121 | 214 | 2.97 | 5.8 | 262 | 366 |
| 4JHX2 | 8.44 | 136 | 210 | 2.87 | 5.32 | 213 | 275 |
|  | 7.43 | 114 | 214 | 2.46 | 5.62 | 250 | 330 |
| 5JHX2 | 7.02 | 145 | 170 | 2.28 | 4.15 | 221 | 266 |
|  | 6.36 | 110 | 203 | 2.28 | 3.98 | 259 | 297 |
| 6JHX2 | 6.80 | 121 | 182 | 1.92 | 4.29 | 242 | 290 |
|  | 7.39 | 120 | 195 | 2.22 | 4.45 | 248 | 282 |

TABLE 18-continued

Inter-Assay Data for All Runs Using Validation QCs

| Run ID | QC 1 (µg/mL) | QC 2 (µg/mL) | QC 3 (µg/mL) | QC 4 (µg/mL) | QC 5 (µg/mL) | QC 6 (µg/mL) | QC 7 (µg/mL) |
|---|---|---|---|---|---|---|---|
| 7JHX2 | 6.64 | 89.6 | 192 | 2.63 | 5.17 | 253 | 310 |
|  | 7.20 | 89.4 | 199 | 2.11 | 4.07 | 172 | 441 |
| 8JHX2 | 6.91 | 118 | 197 | 2.25 | 4.46 | 204 | 293 |
|  | 5.38 | 106 | 197 | 2.45 | 4.46 | 247 | 299 |
| 9JHX2 | 6.85 | 112 | 203 | NRR | NRR | NRR | NRR |
|  | 6.57 | 116 | 202 | NRR | NRR | NRR | NRR |
| 10JHX2 | 7.04 | 127 | 227 | NRR | NRR | NRR | NRR |
|  | 6.79 | 134 | 214 | NRR | NRR | NRR | NRR |
| 11JHX2 | 7.49 | 122 | 197 | NRR | NRR | NRR | NRR |
|  | 7.35 | 121 | 194 | NRR | NRR | NRR | NRR |
| 12JHX2 | 6.32 | 111 | 217 | NRR | NRR | NRR | NRR |
|  | 6.80 | 130 | 219 | NRR | NRR | NRR | NRR |
| 13JHX2 | 8.39 | 118 | 220 | NRR | NRR | NRR | NRR |
|  | 7.26 | 118 | 200 | NRR | NRR | NRR | NRR |
| N | 26 | 26 | 26 | 16 | 16 | 16 | 16 |
| Theoretical Concentration | 7.50 | 120 | 200 | 2.50 | 5.00 | 240 | 320 |
| Mean | 7.17 | 119 | 205 | 2.49 | 4.99 | 237 | 318 |
| S.D. | 0.705 | 12.7 | 15.0 | 0.310 | 0.711 | 31.7 | 46.2 |
| PCV (%) | 10 | 11 | 7 | 13 | 14 | 13 | 15 |
| PDT (%) | −4 | 0 | 3 | −1 | 0 | −1 | −1 |

LEGEND:
PDT Percent Difference from Theoretical
PCV Percent Coefficient of Variation
NRR No Recorded Result.

Assay Sensitivity

Assay sensitivity was evaluated by assessing the accuracy and precision of QC 4 (LLOQ). It was expected that QC 4 would have PCV values less than 25% and PDT values within ±25%. Two replicates of QC 4 were plated in runs 1JHX2-8JHX2, and one of these runs (7JHX2) was rejected due to unacceptable QC quantitation of the mid QC (QC 2; 120 µg/mL). In the seven acceptable runs, QC 4 had an average PCV value of 13% and an average PDT value of 0% (Table 17), well within the acceptable limits. These data indicate that the assay sensitivity for ICD 426 is acceptable at the LLOQ.

Dilutional Linearity and Hook Effect

The ability to dilute samples originally above the upper limit of the standard curve was assessed by evaluating a series of dilutions that were prepared from an over-the-curve QC pool (QC 8). QC 8 was prepared by diluting the MDX-1100 stock (10,200 µg/mL) 1:20 in pooled normal human serum to achieve a concentration of 510 µg/mL. Note that this concentration was the highest that could be achieved to maintain at least 95% serum for QC 8, in accordance with the guidelines of PPD's Standard Operating Procedure (SOP No.: LP-PAL-1013). Dilutions of QC 8 with final concentrations extending above, through and below the range of quantitation were prepared, including: 510 µg/mL, 408 µg/mL (Dil 1.25), 136 µg/mL (Dil 3.75), 45.3 µg/mL (Dil 11.25), 15.1 µg/mL (Dil 33.75), 5.04 µg/mL (Dil 101.25) and 1.68 µg/mL (Dil 303.75). Two replicates of each dilution level were analyzed in run 8JHX2 (n=2, 4 wells).

Samples with dilution factors ranging from Dil 3.75 to Dil 101.25 (within the range of quantitation) had PDT values ranging from −16% to −2%, and met the acceptance criteria that the PDT be within ±20%. Samples with diluted analyte concentrations above (Dil 1 and Dil 1.25) or below (Dil 303.75) the range of quantitation had responses that were >ULOQ or <LLOQ, respectively. Therefore dilutional linearity is considered acceptable for this assay.

The prozone or hook effect was examined by the comparing responses of QC 8 (510 µg/mL) and the QC 8 Dil 1.25 sample (408 µg/mL) to the responses of CAL 10 (320 µg/mL; ULOQ). Both replicates of each dilution had O.D. values that were greater than the recorded values for CAL 10, but were not quantitated by extrapolating the calibration curve beyond the ULOQ. Therefore, there is no hook effect for MDX-1100 concentrations beyond the ULOQ of 320 µg/mL and including 510 µg/mL.

Selectivity (Matrix Effects)

Selectivity is the ability of an analytical method to differentiate and quantify the analyte of interest in the presence of other components in the biological matrix. Selectivity was tested in normal human serum and two disease states, Ulcerative Colitis and Crohn's Disease. For each of the normal and disease state populations, selectivity was assessed by analyzing serum from at least 10 independent donors (5 male and 5 female) at low QC (QC 0, 7.5 µg/mL) and blank levels. One replicate of each spiked and unspiked sample was analyzed (n=1, 2 wells). For each donor population (normal, Ulcerative Colitis, and Crohn's Disease), it was expected that 80% of the low spikes would meet criteria (quantitating within 20% of the theoretical value at the theoretical value) and the unspiked matrix lots would quantitate below the LLOQ.

Selectivity was tested in normal human serum in run 3JHX2. All of the blank normal serum selectivity samples (SP 1-10) screened below the LLOQ. When spiked at the low QC level (7.5 µg/mL), all 10 of the fortified normal human serum samples (SPF 1-10) quantitated with PDT values within ±20%, ranging from 0% to 20%. These data are summarized in Table 19A.

Selectivity was tested in serum from 10 ulcerative colitis individuals in run 4JHX2. All of the blank ulcerative colitis serum samples (SP 11-20) quantitated below the LLOQ. When spiked at the low QC level (7.5 µg/mL), all 10 of the fortified ulcerative colitis individuals (SPF 11-20) quantitated with PDT values within ±20%, ranging from −2% to 18%. These data are summarized in Table 19B.

Selectivity was tested in serum from 10 Crohn's disease individuals in run 12JHX2. All of the blank Crohn's disease serum samples (SP 21-30) quantitated below the LLOQ. When spiked at the low QC level (7.5 µg/mL), all 10 of the fortified Crohn's disease individuals (SPF 21-30) quantitated with PDT values within ±20%, ranging from −15% to 6%. These data are summarized in Table 19C.

Overall, 100% of the selectivity samples from normal and disease states met the acceptance criteria at blank and Low QC levels. All of these selectivity data are summarized in Table 19.

TABLE 19

Selectivity Data

A. Normal Human Serum (3JHX2)

Blank Individuals

| | SP 1 (μg/mL) | SP 2 (μg/mL) | SP 3 (μg/mL) | SP 4 (μg/mL) | SP 5 (μg/mL) | SP 6 (μg/mL) | SP 7 (μg/mL) | SP 8 (μg/mL) | SP 9 (μg/mL) | SP 10 (μg/mL) |
|---|---|---|---|---|---|---|---|---|---|---|
| | <LLOQ | <LLOQ | <LLOQ | <LLOQ | <LLOQ | <LLOQ | <LLOQ | <LLOQ | <LLOQ | <LLOQ |

Individuals Spiked at the Low QC (7.5 μg/mL)

| | SPF 1 (μg/mL) | SPF 2 (μg/mL) | SPF 3 (μg/mL) | SPF 4 (μg/mL) | SPF 5 (μg/mL) | SPF 6 (μg/mL) | SPF 7 (μg/mL) | SPF 8 (μg/mL) | SPF 9 (μg/mL) | SPF 10 (μg/mL) |
|---|---|---|---|---|---|---|---|---|---|---|
| | 7.49 | 8.90 | 9.03 | 8.18 | 8.45 | 8.85 | 8.67 | 8.58 | 8.54 | 8.31 |
| PDT (%) | 0 | 19 | 20 | 9 | 13 | 18 | 16 | 15 | 14 | 11 |

B. Ulcerative Colitis Serum (4JHX2)

Blank Individuals

| | SP 11 (μg/mL) | SP 12 (μg/mL) | SP 13 (μg/mL) | SP 14 (μg/mL) | SP 15 (μg/mL) | SP 16 (μg/mL) | SP 17 (μg/mL) | SP 18 (μg/mL) | SP 19 (μg/mL) | SP 20 (μg/mL) |
|---|---|---|---|---|---|---|---|---|---|---|
| | <LLOQ | <LLOQ | <LLOQ | <LLOQ | <LLOQ | <LLOQ | <LLOQ | <LLOQ | <LLOQ | <LLOQ |

Individuals Spiked at the Low QC (7.5 μg/mL)

| | SPF 11 (μg/mL) | SPF 12 (μg/mL) | SPF 13 (μg/mL) | SPF 14 (μg/mL) | SPF 15 (μg/mL) | SPF 16 (μg/mL) | SPF 17 (μg/mL) | SPF 18 (μg/mL) | SPF 19 (μg/mL) | SPF 20 (μg/mL) |
|---|---|---|---|---|---|---|---|---|---|---|
| | 8.83 | 7.62 | 7.57 | 7.47 | 7.38 | 7.43 | 8.2 | 7.86 | 8.06 | 8.01 |
| PDT (%) | 18 | 2 | 1 | 0 | −2 | −1 | 9 | 5 | 7 | 7 |

C. Crohn's Desease Serum (12JHX2)

Blank Individuals

| | SP 21 (μg/mL) | SP 22 (μg/mL) | SP 23 (μg/mL) | SP 24 (μg/mL) | SP 25 (μg/mL) | SP 26 (μg/mL) | SP 27 (μg/mL) | SP 28 (μg/mL) | SP 29 (μg/mL) | SP 30 (μg/mL) |
|---|---|---|---|---|---|---|---|---|---|---|
| | <LLOQ | <LLOQ | <LLOQ | <LLOQ | <LLOQ | <LLOQ | <LLOQ | <LLOQ | <LLOQ | <LLOQ |

Individuals Spiked at the Low QC (7.5 μg/mL)

| | SPF 21 (μg/mL) | SPF 22 (μg/mL) | SPF 23 (μg/mL) | SPF 24 (μg/mL) | SPF 25 (μg/mL) | SPF 26 (μg/mL) | SPF 27 (μg/mL) | SPF 28 (μg/mL) | SPF 29 (μg/mL) | SPF 30 (μg/mL) |
|---|---|---|---|---|---|---|---|---|---|---|
| | 7.55 | 7.27 | 7.36 | 6.84 | 6.66 | 7.03 | 7.13 | 7.97 | 7.5 | 6.37 |
| PDT (%) | 1 | −3 | −2 | −9 | −11 | −6 | −5 | 6 | 0 | −15 |

Interference (Hemolysis)

The effect of hemolysis on study sample quantification was evaluated by analyzing blank and spiked (low and high QC) samples prepared in hemolyzed serum. Ten individual donors exhibiting a low level of hemolysis (hemoglobin concentration of approximately 70 mg/dL as specified by the vendor) and ten individual donors exhibiting a high level of hemolysis (hemoglobin concentration of approximately 550 mg/dL as specified by the vendor) were evaluated using freshly prepared calibration curves prepared in normal human serum. Single replicates (n=1, 2 wells) of the blank, Low QC and High QC samples were prepared from each hemolyzed sample and analyzed. Hemolysis data for each of the spiked hemolysis samples were expected to have PCV values<20% and the accuracy of the mean value was expected to be within ±20% of the theoretical value for that pool. Blank samples were expected to have a PCV less than 20% and quantitate lower than the LLOQ. At least 80% of hemolysis samples at each level were required to meet acceptance criteria.

Interference in Samples Exhibiting a Low Level of Hemolysis

Ten individual samples exhibiting a low level of hemolysis were analyzed in run 10JHX2. One of the 10 individual samples (HS 1-10) analyzed at the blank level had a replicate PCV value of 33% and did not meet the acceptance criteria, although both of the duplicate determinations for this sample quantitated below CAL 1 (anchor) and the LLOQ. The remaining nine blank individuals quantitated below the LLOQ with PCV values less than or equal to 13%. All 10 of the individual samples spiked at the low QC level (HEMQC 1-10) had acceptable PCV values, ranging from 0% to 6%, and acceptable PDT values ranging from −18% to −1%. One of the 10 individuals spiked at the High QC level (HEMQC 11-20) failed to quantitate with an acceptable PDT (HEMQC 12; PDT=−23%). The remaining nine individuals spiked at the High QC level had acceptable PCV values ranging from 0% to 5% and acceptable PDT values ranging from −7% to 16%. Overall, the acceptance criteria for samples exhibiting a low level of hemolysis were met at the blank (90% acceptable), low (100% acceptable), and high (90% acceptable) QC levels. These data are summarized in Table 20A.

TABLE 20

Hemolysis Interference Data
A. Interference in Individual Samples with a Low Level of Hemolysis (10JHX2)

| | Blank Hemolyzed Samples (Hemoglobin ~70 mg/dL) | | | | | | | | | |
|---|---|---|---|---|---|---|---|---|---|---|
| | HS 1 (µg/mL) | HS 2 (µg/mL) | HS 3 (µg/mL) | HS 4 (µg/mL) | HS 5 (µg/mL) | HS 6 (µg/mL) | HS 7 (µg/mL) | HS 8 (µg/mL) | HS 9 (µg/mL) | HS 10 (µg/mL) |
| Mean | <LLOQ | <LLOQ | <LLOQ | <LLOQ | <LLOQ | <LLOQ | RCV | <LLOQ | <LLOQ | <LLOQ |
| PCV (%) | 13 | 13 | 0 | 0 | 0 | 0 | 33 | 0 | 0 | 0 |

| | Hemolyzed Samples (Hemoglobin ~70 mg/dL) Spiked at the Low QC (7.5 µg/mL) | | | | | | | | | |
|---|---|---|---|---|---|---|---|---|---|---|
| | HEMQC 1 (µg/mL) | HEMQC 2 (µg/mL) | HEMQC 3 (µg/mL) | HEMQC 4 (µg/mL) | HEMQC 5 (µg/mL) | HEMQC 6 (µg/mL) | HEMQC 7 (µg/mL) | HEMQC 8 (µg/mL) | HEMQC 9 (µg/mL) | HEMQC 10 (µg/mL) |
| Mean | 6.49 | 6.59 | 7.44 | 7.14 | 7.44 | 6.14 | 6.19 | 6.14 | 6.99 | 6.29 |
| PCV (%) | 3 | 3 | 0 | 2 | 6 | 2 | 1 | 0 | 5 | 1 |
| PDT (%) | −13 | −12 | −1 | −5 | −1 | −18 | −18 | −18 | −7 | −16 |

| | Hemolyzed Samples (Hemoglobin ~70 mg/dL) Spiked at the High QC (200 µg/mL) | | | | | | | | | |
|---|---|---|---|---|---|---|---|---|---|---|
| | HEMQC 11 (µg/mL) | HEMQC 12** (µg/mL) | HEMQC 13 (µg/mL) | HEMQC 14 (µg/mL) | HEMQC 15 (µg/mL) | HEMQC 16 (µg/mL) | HEMQC 17 (µg/mL) | HEMQC 18 (µg/mL) | HEMQC 19 (µg/mL) | HEMQC 20 (µg/mL) |
| | 203 | 154** | 221 | 218 | 211 | 199 | 204 | 186 | 201 | 231 |
| PCV (%) | 0 | 2 | 3 | 1 | 1 | 5 | 4 | 3 | 1 | 1 |
| PDT (%) | 2 | −23** | 11 | 9 | 5 | 0 | 2 | −7 | 0 | 16 |

Interference in Samples Exhibiting a High Level of Hemolysis

Ten individual samples exhibiting a high level of hemolysis were analyzed in run 11JHX2. One of the 10 individual samples (HS 101-110) analyzed at the blank level had a replicate PCV value of 24% and did not meet acceptance criteria, although both of the duplicate determinations for this sample quantitated below CAL 1 (anchor) and the LLOQ. The remaining nine blank individuals quantitated below the LLOQ with PCV values less than or equal to 16%. All 10 of the individual samples spiked at the low QC level (HEMQC 101-110) had acceptable PCV values ranging from 1% to 6% and acceptable PDT values ranging from −15% to 8%. All 10 of the individuals spiked at the High QC level (HEMQC 111-120) also had acceptable PCV values ranging from 0% to 6% and acceptable PDT values ranging from −7% to 12%. Overall, the acceptance criteria for samples exhibiting a high level of hemolysis were met at the blank (90% acceptable), Low (100% acceptable), and High (100% acceptable) QC levels. These data are summarized in Table 20B.

TABLE 20

Hemolysis Interference Data (Cont.)
B. Interference in Individual Samples with a High Level of Hemolysis (11JHX2)

| | Blank Hemolyzed Samples (Hemoglobin ~550 mg/dL) | | | | | | | | | |
|---|---|---|---|---|---|---|---|---|---|---|
| | HS 101 (µg/mL) | HS 102 (µg/mL) | HS 103 (µg/mL) | HS 104 (µg/mL) | HS 105 (µg/mL) | HS 106 (µg/mL) | HS 107 (µg/mL) | HS 108 (µg/mL) | HS 109 (µg/mL) | (µg/mL) |
| Mean | <LLOQ | <LLOQ | <LLOQ | <LLOQ | <LLQQ | <LLOQ | RCV | <LLOQ | <LLOQ | <LLOQ |
| PCV (%) | 0 | 11 | 13 | 0 | 0 | 16 | 24 | 0 | 0 | 13 |

| | Hemolyzed Samples (Hemoglobin ~550 mg/dL) Spiked at the Low QC (7.5 µg/mL) | | | | | | | | | |
|---|---|---|---|---|---|---|---|---|---|---|
| | HEMQC 101 (µg/mL) | HEMQC 102 (µg/mL) | HEMQC 103 (µg/mL) | HEMQC 104 (µg/mL) | HEMQC 105 (µg/mL) | HEMQC 106 (µg/mL) | HEMQC 107 (µg/mL) | HEMQC 108 (µg/mL) | HEMQC 109 (µg/mL) | HEMQC 110 (µg/mL) |
| Mean | 6.40 | 7.40 | 6.59 | 8.01 | 7.54 | 7.40 | 8.11 | 6.54 | 7.54 | 6.73 |
| PCV (%) | 1 | 2 | 1 | 6 | 5 | 2 | 3 | 4 | 1 | 2 |
| PDT (%) | −15 | −1 | −12 | 7 | 1 | −1 | 8 | −13 | 1 | −10 |

TABLE 20-continued

Hemolysis Interference Data (Cont.)
B. Interference in Individual Samples with a High Level of Hemolysis (11JHX2)

Hemolyzed Samples (Hemoglobin ~550 mg/dL) Spiked at the High QC (200 pg/μg/mL)

|  | HEMQC 111 (μg/mL) | HEMQC 112 (μg/mL) | HEMQC 113 (μg/mL) | HEMQC 114 (μg/mL) | HEMQC 115 (μg/mL) | HEMQC 116 (μg/mL) | HEMQC 117 (μg/mL) | HEMQC 118 (μg/mL) | HEMQC 119 (μg/mL) | HEMQC 130 (μg/mL) |
|---|---|---|---|---|---|---|---|---|---|---|
| Mean | 203 | 186 | 213 | 208 | 224 | 218 | 213 | 224 | 214 | 204 |
| PCV (%) | 2 | 3 | 2 | 2 | 1 | 0 | 6 | 1 | 5 | 2 |
| PDT (%) | 2 | −7 | 7 | 4 | 12 | 9 | 7 | 12 | 7 | 2 |

Legend:
PDT Percent Difference from Theoretical
RCV Replicate Analysis Coefficient of Variation Unacceptable
**PDT Exceeds 20% and Does Not Meet Acceptance Criteria Analyte Stability in Matrix
Thawed Matrix Stability at 2-8° C.

The stability of MDX-1100 in thawed matrix was evaluated at 2-8° C. to determine whether holding samples in a thawed state for a period of time adversely affected analyte stability in normal human serum. Six replicates (n=6, 12 wells) of the low QC and high QC were thawed and allowed to stay in a refrigerator for approximately 24 hours prior to analysis in 5JHX2. In order for the data for the stability samples to be considered acceptable, the PCV of the replicate determinations was expected to not exceed 20% and accuracy of the mean value for each level was expected to be within 20% of the theoretical concentration. The overall PCV for the low and high stability QCs was 4% and 5%, respectively. Percent difference from the theoretical for the low and high QCs was −11% and 10%, respectively. These data indicate that MDX-1100 is stable at 2-8° C. for approximately 24 hours.

Stability at Room Temperature

To determine the stability at room temperature (bench top), six replicates (n=6, 12 wells) of the low QC and high QC were thawed and allowed to stay at room temperature for approximately 24 hours prior to analysis in 6JHX2. To meet acceptance criteria, stability samples were to have PCV≤20% and to quantitate within 20% of the theoretical concentration. The overall PCV for the low and high stability QCs was 9% and 8%, respectively. Percent difference from the theoretical for the low and high QCs was −12% and 6%, respectively. These data indicate that MDX-1100 is stable in thawed matrix at room temperature for approximately 24 hours.

Freeze-Thaw Stability

Freeze-Thaw stability was assessed after cycling the low and high QC 5 times. Each cycle consisted of keeping the sample frozen (for at least 24 hours for the first cycle and for at least twelve hours for all subsequent cycles) and then keeping the sample at ambient room temperature for at least thirty minutes but no longer than 2 hours. Six replicates (n=6, 12 wells) of the cycled low QC and high QC were analyzed in 9JHX2. To meet acceptance criteria, freeze-thaw samples were expected to have PCV≤20% and to quantitate within 20% of the theoretical concentration. The overall PCV for the low and high stability QCs was 4% and 8%, respectively. Percent difference from the theoretical for the low and high QCs was −13% and −8%, respectively, and therefore establishes stability for five freeze-thaw cycles.

Short Term Stability at −20° C. and −80° C.

To validate the use of frozen calibration standards, MDX-1100 stability in frozen human serum was demonstrated for a period covering the age of the oldest calibration standard or QC pool used during validation (15 days). To test this, the LQC and HQC that were frozen at −20° C. and −80° C. for 15 days were compared to a freshly prepared calibration curve and acceptance QCs. Six replicates (n=6, 12 wells) of the LQC and HQC samples at each temperature were assayed in 14JHX2. To meet acceptance criteria, the short-term stability samples stored at both temperatures must have PCV values must be ≤20% and PDT values must be within ±20%. The overall PCV for the low and high short-term stability samples at −80° C. was 16% and 5%, respectively, and the PDT values were 0% and 13%, respectively. For the −20° C. short-term stability samples, the overall PCV values were 7% and 4%, respectively, and the PDT values were −6% and 4%, respectively. These data indicate that MDX-1100 is stable in normal human serum when stored at −80° C. or −20° C. for approximately 15 days.

Cross-Validation of ICD 426 with ICD 274

To evaluate method changes and determine if results obtained using the method ICD 426 were consistent with those obtained using method ICD 274, samples analyzed in BMS study IM129-004 (PPD Project Code: NDT) that were representative of high, mid and low study concentrations were pooled (≥3 individual samples per pool) to generate 15 test sample pools. One replicate (n=1, 2 wells) of each pooled sample and two replicates (n=2, 4 wells) of each acceptance QC listed in Method ICD 274 (QC 1: 3 μg/mL; QC 2: 7.5 μg/mL; QC 3: 25 μg/mL) were analyzed using methods ICD 426 and ICD 274. For the methods to be considered cross-validated, two-thirds of the results for the pooled samples and three-fourths of the QC levels were expected to have a percent difference (% DIFF) of ≤20% (values obtained using ICD 426 vs. those obtained using ICD 274). A separate project code, JHX4, was created in order to import data acquired using the previously validated method (ICD 274) into Assist.

Cross-validation runs were initially performed in runs 13JHX2 and 1JHX4. Of the 15 sample pools, 13 (87%) met acceptance criteria with % DIFF values ranging from 3% to 18%. The two remaining pools, had % DIFF values of 29% and 38%. Overall, 87% of the pooled samples met the acceptance criteria for cross-validation.

QCs 1-3 were also analyzed in 13JHX2 and 1JHX4. QC 2 and QC 3 had % DIFF of 13% and 7%, respectively, and met the acceptance criteria. QC 1 failed to meet the acceptance criteria with a % DIFF value of 35%. A second comparison between the methods for QC 1 was performed by plating 4 replicates of QC 1 (n=4, 8 wells) in runs 14JHX2 and 2JHX4. One outlier was identified in 14JHX2 and removed for comparison. The % DIFF for this second comparison of QC 1 was 18%. Together, all acceptance criteria for the comparisons of the pooled samples and the QCs were met to cross-validate Method ICD 426 and ICD 274.

SOP Deviation

There were no SOP deviations noted during the validation.

Example 5

Structural Characterization of Mouse Anti-MDX-1100 Idiotypic Antibodies

The cDNA sequences encoding the heavy and light chain variable regions of the monoclonal antibodies expressed by the 10C8, 6C9, 2F5, and 23H10 clones described in Example 2 were sequenced using standard DNA sequencing techniques and the expressed proteins were characterized by standard protein chemistry analysis.

The nucleotide and amino acid sequences of the heavy chain variable region of 10C8 are shown in FIG. 13A and in SEQ ID NOs: 11 and 12, respectively. The CDR1, CDR2 and CDR3 regions are delineated (SEQ ID NOs: 13, 14, and 15, respectively).

The nucleotide and amino acid sequences of the light chain variable region of 10C8 are shown in FIG. 13B and in SEQ ID NOs: 16 and 17, respectively. The CDR1, CDR2 and CDR3 regions are delineated (SEQ ID NOs: 18, 19, and 20, respectively).

The nucleotide and amino acid sequences of the heavy chain variable region of 6C9 are shown in FIG. 14A and in SEQ ID NOs: 21 and 22, respectively. The CDR1, CDR2 and CDR3 regions are delineated (SEQ ID NOs: 23, 24, and 25, respectively).

The nucleotide and amino acid sequences of the light chain variable region of 6C9 are shown in FIG. 14B and in SEQ ID NOs: 26 and 27, respectively. The CDR1, CDR2 and CDR3 regions are delineated (SEQ ID NOs: 28, 29, and 30, respectively).

The nucleotide and amino acid sequences of the heavy chain variable region of 2F5 are shown in FIG. 15A and in SEQ ID NOs: 31 and 32, respectively. The CDR1, CDR2 and CDR3 regions are delineated (SEQ ID NOs: 33, 34, and 35, respectively).

The nucleotide and amino acid sequences of the light chain variable region of 2F5 are shown in FIG. 15B and in SEQ ID NOs: 36 and 37, respectively. The CDR1, CDR2 and CDR3 regions are delineated (SEQ ID NOs: 38, 39, and 40, respectively).

The nucleotide and amino acid sequences of the heavy chain variable region of 23H10 are shown in FIG. 16A and in SEQ ID NOs: 41 and 42, respectively. The CDR1, CDR2 and CDR3 regions are delineated (SEQ ID NOs: 43, 44, and 45, respectively).

The nucleotide and amino acid sequences of the light chain variable region of 23H10 are shown in FIG. 16B and in SEQ ID NOs: 46 and 47, respectively. The CDR1, CDR2 and CDR3 regions are delineated (SEQ ID NOs: 48, 49, and 50, respectively).

SUMMARY OF SEQUENCE LISTING

| SEQ ID NO: | SEQUENCE |
| --- | --- |
| 1 | VH nucleotide MDX1100 |
| 2 | VH a.a. MDX1100 |
| 3 | VH CDR1 a.a. MDX1100 |
| 4 | VH CDR2 a.a. MDX1100 |
| 5 | VH CDR3 a.a. MDX1100 |
| 6 | Vk nucleotide MDX1100 |
| 7 | Vk a.a. MDX1100 |
| 8 | Vk CDR1 a.a. MDX1100 |
| 9 | Vk CDR2 a.a. MDX1100 |
| 10 | Vk CDR3 a.a. MDX1100 |
| 11 | VH nucleotide 10C8 |
| 12 | VH a.a. 10C8 |
| 13 | VH CDR1 a.a. 10C8 |
| 14 | VH CDR2 a.a. 10C8 |
| 15 | VH CDR3 a.a. 10C8 |
| 16 | Vk nucleotide 10C8 |
| 17 | Vk a.a. 10C8 |
| 18 | Vk CDR1 a.a. 10C8 |
| 19 | Vk CDR2 a.a. 10C8 |
| 20 | Vk CDR3 a.a. 10C8 |
| 21 | VH nucleotide 6C9 |
| 22 | VH a.a. 6C9 |
| 23 | VH CDR1 a.a. 6C9 |
| 24 | VH CDR2 a.a. 6C9 |
| 25 | VH CDR3 a.a. 6C9 |
| 26 | Vk nucleotide 6C9 |
| 27 | Vk a.a. 6C9 |
| 28 | Vk CDR1 a.a. 6C9 |
| 29 | Vk CDR2 a.a. 6C9 |
| 30 | Vk CDR3 a.a. 6C9 |
| 31 | VH nucleotide 2F5 |
| 32 | VH a.a. 2F5 |
| 33 | VH CDR1 a.a. 2F5 |
| 34 | VH CDR2 a.a. 2F5 |
| 35 | VH CDR3 a.a. 2F5 |
| 36 | Vk nucleotide 2F5 |
| 37 | Vk a.a. 2F5 |
| 38 | Vk CDR1 a.a. 2F5 |
| 39 | Vk CDR2 a.a. 2F5 |
| 40 | Vk CDR3 a.a. 2F5 |
| 41 | VH nucleotide 23H10 |
| 42 | VH a.a. 23H10 |
| 43 | VH CDR1 a.a. 23H10 |
| 44 | VH CDR2 a.a. 23H10 |
| 45 | VH CDR3 a.a. 23H10 |
| 46 | Vk nucleotide 23H10 |
| 47 | Vk a.a. 23H10 |
| 48 | Vk CDR1 a.a. 23H10 |
| 49 | Vk CDR2 a.a. 23H10 |
| 50 | Vk CDR3 a.a. 23H10 |

EQUIVALENTS

Those skilled in the art will recognize or be able to ascertain, using no more than routine experimentation, many equivalents of the specific embodiments of the invention described herein. Such equivalents are intended to be encompassed by the following claims.

We claim:

1. An isolated monoclonal anti-idiotypic antibody, or an antigen binding portion thereof, which binds to the anti-Interferon gamma inducible protein 10 (IP-10) antibody MDX-1100 and comprises:
   (a) a heavy chain variable region CDR1 comprising SEQ ID NO: 13;
   (b) a heavy chain variable region CDR2 comprising SEQ ID NO: 14;
   (c) a heavy chain variable region CDR3 comprising SEQ ID NO: 15;
   (d) a light chain variable region CDR1 comprising SEQ ID NO: 18;
   (e) a light chain variable region CDR2 comprising SEQ ID NO: 19; and
   (f) a light chain variable region CDR3 comprising SEQ ID NO: 20;
   (a) a heavy chain variable region CDR1 comprising SEQ ID NO: 23;
   (b) a heavy chain variable region CDR2 comprising SEQ ID NO: 24;
   (c) a heavy chain variable region CDR3 comprising SEQ ID NO: 25;
   (d) a light chain variable region CDR1 comprising SEQ ID NO: 28;
   (e) a light chain variable region CDR2 comprising SEQ ID NO: 29; and
   (f) a light chain variable region CDR3 comprising SEQ ID NO: 30;
   (a) a heavy chain variable region CDR1 comprising SEQ ID NO: 33;
   (b) a heavy chain variable region CDR2 comprising SEQ ID NO: 34;
   (c) a heavy chain variable region CDR3 comprising SEQ ID NO: 35;
   (d) a light chain variable region CDR1 comprising SEQ ID NO: 38;
   (e) a light chain variable region CDR2 comprising SEQ ID NO: 39; and
   (f) a light chain variable region CDR3 comprising SEQ ID NO: 40; or
   (a) a heavy chain variable region CDR1 comprising SEQ ID NO: 43;

(b) a heavy chain variable region CDR2 comprising SEQ ID NO: 44;
(c) a heavy chain variable region CDR3 comprising SEQ ID NO: 45;
(d) a light chain variable region CDR1 comprising SEQ ID NO: 48;
(e) a light chain variable region CDR2 comprising SEQ ID NO: 49; and
(f) a light chain variable region CDR3 comprising SEQ ID NO: 50.

2. The anti-idiotypic antibody, or an antigen binding portion thereof, of claim 1, selected from a murine antibody, a chimeric antibody, a humanized antibody, and a human antibody.

3. The anti-idiotypic antibody, or an antigen binding portion thereof, of claim 1, which comprises:
(a) a heavy chain variable region CDR1 comprising SEQ ID NO: 13;
(b) a heavy chain variable region CDR2 comprising SEQ ID NO: 14;
(c) a heavy chain variable region CDR3 comprising SEQ ID NO: 15;
(d) a light chain variable region CDR1 comprising SEQ ID NO: 18;
(e) a light chain variable region CDR2 comprising SEQ ID NO: 19; and
(f) a light chain variable region CDR3 comprising SEQ ID NO: 20.

4. The anti-idiotypic antibody, or an antigen binding portion thereof, of claim 1, which comprises:
(a) a heavy chain variable region CDR1 comprising SEQ ID NO: 23;
(b) a heavy chain variable region CDR2 comprising SEQ ID NO: 24;
(c) a heavy chain variable region CDR3 comprising SEQ ID NO: 25;
(d) a light chain variable region CDR1 comprising SEQ ID NO: 28;
(e) a light chain variable region CDR2 comprising SEQ ID NO: 29; and
(f) a light chain variable region CDR3 comprising SEQ ID NO: 30.

5. The anti-idiotypic antibody, or an antigen binding portion thereof, of claim 1, which comprises:
(a) a heavy chain variable region CDR1 comprising SEQ ID NO: 33;
(b) a heavy chain variable region CDR2 comprising SEQ ID NO: 34;
(c) a heavy chain variable region CDR3 comprising SEQ ID NO: 35;
(d) a light chain variable region CDR1 comprising SEQ ID NO: 38;
(e) a light chain variable region CDR2 comprising SEQ ID NO: 39; and
(f) a light chain variable region CDR3 comprising SEQ ID NO: 40.

6. The anti-idiotypic antibody, or an antigen binding portion thereof, of claim 1, which comprises:
(a) a heavy chain variable region CDR1 comprising SEQ ID NO: 43;
(b) a heavy chain variable region CDR2 comprising SEQ ID NO: 44;
(c) a heavy chain variable region CDR3 comprising SEQ ID NO: 45;
(d) a light chain variable region CDR1 comprising SEQ ID NO: 48;
(e) a light chain variable region CDR2 comprising SEQ ID NO: 49; and
(f) a light chain variable region CDR3 comprising SEQ ID NO: 50.

7. The anti-idiotypic antibody, or an antigen binding portion thereof, of claim 1, which comprises:
(a) a heavy chain variable region comprising the amino acid sequence of SEQ ID NO: 12; and a light chain variable region comprising the amino acid sequence of SEQ ID NO: 17;
(b) a heavy chain variable region comprising the amino acid sequence of SEQ ID NO: 22; and a light chain variable region comprising the amino acid sequence of SEQ ID NO: 27;
(c) a heavy chain variable region comprising the amino acid sequence of SEQ ID NO: 32; and a light chain variable region comprising the amino acid sequence of SEQ ID NO: 37; or
(d) a heavy chain variable region comprising the amino acid sequence of SEQ ID NO: 42; and a light chain variable region comprising the amino acid sequence of SEQ ID NO: 47.

8. The anti-idiotypic antibody, or an antigen binding portion thereof, of claim 7, which comprises a heavy chain variable region comprising the amino acid sequence of SEQ ID NO: 12; and a light chain variable region comprising the amino acid sequence of SEQ ID NO: 17.

9. The anti-idiotypic antibody, or an antigen binding portion thereof, of claim 7, which comprises a heavy chain variable region comprising the amino acid sequence of SEQ ID NO: 22; and a light chain variable region comprising the amino acid sequence of SEQ ID NO: 27.

10. The anti-idiotypic antibody, or an antigen binding portion thereof, of claim 7, which comprises a heavy chain variable region comprising the amino acid sequence of SEQ ID NO: 32; and a light chain variable region comprising the amino acid sequence of SEQ ID NO: 37.

11. The anti-idiotypic antibody, or an antigen binding portion thereof, of claim 7, which comprises a heavy chain variable region comprising the amino acid sequence of SEQ ID NO: 42; and a light chain variable region comprising the amino acid sequence of SEQ ID NO: 47.

12. A kit comprising: (1) the anti-idiotypic antibody, or antigen-binding portion thereof, of claim 1; and (2) reagents necessary for facilitating an antibody-antigen complex formation.

13. A hybridoma cell line which produces the monoclonal anti-idiotypic antibody of claim 1.

* * * * *

SEQUENCE LISTING

<160> NUMBER OF SEQ ID NOS: 50

<210> SEQ ID NO 1
<211> LENGTH: 372
<212> TYPE: DNA
<213> ORGANISM: Homo Sapien

<400> SEQUENCE: 1

```
caaatgcagc tggtggagtc tgggggaggc gtggtccagc ctgggaggtc cctgagactc    60
tcctgtacag cgtctggatt caccttcagt aacaatggca tgcactgggt ccgccaggct   120
ccaggcaagg gctggagtg gtggcagtt atatggtttg atggaatgaa taaattctat   180
gtagactccg tgaagggccg attcaccatc tccagagaca attccaagaa cacgctgtat   240
ctggaaatga acagcctgag agccgaggac acggctatat attactgtgc gagagaaggg   300
gatggttcgg ggatttatta ctactacggt atggacgtct ggggccaagg gaccacggtc   360
accgtctcct ca                                                      372
```

<210> SEQ ID NO 2
<211> LENGTH: 125
<212> TYPE: PRT
<213> ORGANISM: Homo Sapien

<400> SEQUENCE: 2

```
Gln Met Gln Leu Val Glu Ser Gly Gly Gly Val Val Gln Pro Gly Arg
 1               5                  10                  15

Ser Leu Arg Leu Ser Cys Thr Ala Ser Gly Phe Thr Phe Ser Asn Asn
             20                  25                  30

Gly Met His Trp Val Arg Gln Ala Pro Gly Lys Gly Leu Glu Trp Val
         35                  40                  45

Ala Val Ile Trp Phe Asp Gly Met Asn Lys Phe Tyr Val Asp Ser Val
     50                  55                  60

Lys Gly Arg Phe Thr Ile Ser Arg Asp Asn Lys Asn Thr Leu Tyr
 65                  70                  75                  80

Leu Glu Met Asn Ser Leu Arg Ala Glu Asp Thr Ala Ile Tyr Tyr Thr
                 85                  90                  95

Cys Ala Arg Glu Gly Asp Gly Ser Gly Ile Tyr Tyr Tyr Gly Met
            100                 105                 110

Asp Val Trp Gly Gln Gly Thr Thr Val Thr Val Ser Ser
        115                 120                 125
```

<210> SEQ ID NO 3
<211> LENGTH: 5
<212> TYPE: PRT
<213> ORGANISM: Homo Sapien

<400> SEQUENCE: 3

```
Asn Asn Gly Met His
 1               5
```

<210> SEQ ID NO 4
<211> LENGTH: 17
<212> TYPE: PRT
<213> ORGANISM: Homo Sapien

<400> SEQUENCE: 4

```
Val Ile Trp Phe Asp Gly Met Asn Lys Phe Tyr Val Asp Ser Val Lys
 1               5                  10                  15

Gly
```

<210> SEQ ID NO 5
<211> LENGTH: 15
<212> TYPE: PRT
<213> ORGANISM: Homo Sapien

-continued

<400> SEQUENCE: 5

Glu Gly Asp Gly Ser Gly Ile Tyr Tyr Tyr Tyr Gly Met Asp Val
1               5                   10                  15

<210> SEQ ID NO 6
<211> LENGTH: 327
<212> TYPE: DNA
<213> ORGANISM: Homo Sapien

<400> SEQUENCE: 6

```
gaaattgtgt tgacgcagtc tccaggcacc ctgtctttgt ctccagggga aagagccacc    60
ctctcctgca gggccagtca gagtgttagc agcagctatt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctat attcactttc   300
ggccctggga ccaaagtgga tatcaaa                                       327
```

<210> SEQ ID NO 7
<211> LENGTH: 109
<212> TYPE: PRT
<213> ORGANISM: Homo Sapien

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
            100                 105

<210> SEQ ID NO 8
<211> LENGTH: 12
<212> TYPE: PRT
<213> ORGANISM: Homo Sapien

<400> SEQUENCE: 8

Arg Ala Ser Gln Ser Val Ser Ser Ser Tyr Leu Ala
1               5                   10

<210> SEQ ID NO 9
<211> LENGTH: 7
<212> TYPE: PRT
<213> ORGANISM: Homo Sapien

<400> SEQUENCE: 9

Gly Ala Ser Ser Arg Ala Thr
1               5

<210> SEQ ID NO 10
<211> LENGTH: 10

```
<212> TYPE: PRT
<213> ORGANISM: Homo Sapien

<400> SEQUENCE: 10

Gln Gln Tyr Gly Ser Ser Pro Ile Phe Thr
1               5                   10

<210> SEQ ID NO 11
<211> LENGTH: 354
<212> TYPE: DNA
<213> ORGANISM: Homo Sapien

<400> SEQUENCE: 11
gaggtgaagc ttctcgagtc tggaggtggc ctggtgcagc ctggaggatc cctgaaactc      60
tcctgtgcag cctcaggatt cgatttagt agatactgga tgatttgggt ccggcaggct     120
ccagggaaag ggctagaatg gattggagaa attaatccag atagcagtac gataaactat    180
acgccatctc taaaggataa attcatcatc tccagagaca acgccaaaaa tacgctgtac    240
ctgcaaatga gcaaagtgag atctgaggac acagcccttt attactgtgc aagacccctc    300
tacggctacg ggtttgctta ctggggccaa gggactctgg tcactgtctc tgca          354

<210> SEQ ID NO 12
<211> LENGTH: 118
<212> TYPE: PRT
<213> ORGANISM: Homo Sapien

<400> SEQUENCE: 12

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ile Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Leu Tyr Gly Tyr Gly Phe Ala Tyr Trp Gly Gln Gly Thr
            100                 105                 110

Leu Val Thr Val Ser Ala
        115

<210> SEQ ID NO 13
<211> LENGTH: 5
<212> TYPE: PRT
<213> ORGANISM: Homo Sapien

<400> SEQUENCE: 13

Arg Tyr Trp Met Ile
1               5

<210> SEQ ID NO 14
<211> LENGTH: 17
<212> TYPE: PRT
<213> ORGANISM: Homo Sapien

<400> SEQUENCE: 14
```

```
Glu Ile Asn Pro Asp Ser Ser Thr Ile Asn Tyr Thr Pro Ser Leu Lys
1               5                   10                  15

Asp

<210> SEQ ID NO 15
<211> LENGTH: 9
<212> TYPE: PRT
<213> ORGANISM: Homo Sapien

<400> SEQUENCE: 15

Pro Leu Tyr Gly Tyr Gly Phe Ala Tyr
1               5

<210> SEQ ID NO 16
<211> LENGTH: 321
<212> TYPE: DNA
<213> ORGANISM: Homo Sapien

<400> SEQUENCE: 16
gacattgtga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaactact gattttctcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctcctcggac gttcggtgga     300
ggcaccaagg tggaaatcaa a                                              321

<210> SEQ ID NO 17
<211> LENGTH: 107
<212> TYPE: PRT
<213> ORGANISM: Homo Sapien

<400> SEQUENCE: 17

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Val Glu Ile Lys
            100                 105

<210> SEQ ID NO 18
<211> LENGTH: 11
<212> TYPE: PRT
<213> ORGANISM: Homo Sapien

<400> SEQUENCE: 18

Lys Ala Ser Gln Asp Val Ser Thr Ala Val Ala
1               5                   10

<210> SEQ ID NO 19
<211> LENGTH: 8
```

```
<212> TYPE: PRT
<213> ORGANISM: Homo Sapien

<400> SEQUENCE: 19

Ser Ala Ser Tyr Arg Tyr Thr Gly
1               5

<210> SEQ ID NO 20
<211> LENGTH: 9
<212> TYPE: PRT
<213> ORGANISM: Homo Sapien

<400> SEQUENCE: 20

Gln Gln His Tyr Ser Thr Pro Arg Thr
1               5

<210> SEQ ID NO 21
<211> LENGTH: 351
<212> TYPE: DNA
<213> ORGANISM: Homo Sapien

<400> SEQUENCE: 21
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacct acactggaga gccaacatat     180
gctgatgact tcaagggacg gtttgccttc tctttggaaa cctctgccag cactgcctat     240
ttgcagatca caaccctcaa aaatgaggac acggctacat atttctgtgc aaaggacggg     300
acgggtgcta tggactactg gggtcaagga acctcagtca ccgtctcctc a              351

<210> SEQ ID NO 22
<211> LENGTH: 117
<212> TYPE: PRT
<213> ORGANISM: Homo Sapien

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Lys Asp Gly Thr Gly Ala Met Asp Tyr Trp Gly Gln Gly Thr Ser
            100                 105                 110

Val Thr Val Ser Ser
        115

<210> SEQ ID NO 23
<211> LENGTH: 5
<212> TYPE: PRT
<213> ORGANISM: Homo Sapien

<400> SEQUENCE: 23
```

Asn Tyr Gly Met Asn
1               5

<210> SEQ ID NO 24
<211> LENGTH: 17
<212> TYPE: PRT
<213> ORGANISM: Homo Sapien

<400> SEQUENCE: 24

Trp Ile Asn Thr Tyr Thr Gly Glu Pro Thr Tyr Ala Asp Asp Phe Lys
1               5                   10                  15

Gly

<210> SEQ ID NO 25
<211> LENGTH: 8
<212> TYPE: PRT
<213> ORGANISM: Homo Sapien

<400> SEQUENCE: 25

Asp Gly Thr Gly Ala Met Asp Tyr
1               5

<210> SEQ ID NO 26
<211> LENGTH: 321
<212> TYPE: DNA
<213> ORGANISM: Homo Sapien

<400> SEQUENCE: 26

```
gacattgtga tgactcagtc tccagccacc ctgtctgtga ctccaggaga tagagtctct      60
ctttcctgca gggccagcca gagtattagc gactacttac actggtatca acaaaaatca    120
catgagtctc caaggcttct catcaaatat gcttcccaat ccatctctgg gatcccctcc    180
aggttcagtg gcagtggatc agggtcagat ttcactctca gtatcaacag tgtggaacct    240
gaagatgttg gagtgtatta ctgtcaaaat ggtcacagct ttccgtacac gttcggaggg    300
gggaccaagc tggaaataaa a                                               321
```

<210> SEQ ID NO 27
<211> LENGTH: 107
<212> TYPE: PRT
<213> ORGANISM: Homo Sapien

<400> SEQUENCE: 27

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 28
<211> LENGTH: 11

<212> TYPE: PRT
<213> ORGANISM: Homo Sapien

<400> SEQUENCE: 28

Arg Ala Ser Gln Ser Ile Ser Asp Tyr Leu His
1               5                   10

<210> SEQ ID NO 29
<211> LENGTH: 7
<212> TYPE: PRT
<213> ORGANISM: Homo Sapien

<400> SEQUENCE: 29

Tyr Ala Ser Gln Ser Ile Ser
1               5

<210> SEQ ID NO 30
<211> LENGTH: 9
<212> TYPE: PRT
<213> ORGANISM: Homo Sapien

<400> SEQUENCE: 30

Gln Asn Gly His Ser Phe Pro Tyr Thr
1               5

<210> SEQ ID NO 31
<211> LENGTH: 351
<212> TYPE: DNA
<213> ORGANISM: Homo Sapien

<400> SEQUENCE: 31
cagatccagt tggtgcagtc tggacctgag ctgaagaagc ctggagagac agtcaagatc      60
tcctgcaagg cttctgggta taccttcaca aattatggaa tgaactgggt gaagcaggct     120
ccaggaaagg gtttaaagtg gatgggctgg ataaacacct acactggaga gtcagcatat     180
gctgatgact caaggggacg gtttgccttc tccttggaaa cctctgccag cactgcctat     240
ttgcagatca acaacctcaa aaatgaggac acggctacat atttctgtgc aaccgggggt     300
tactatggta tggactactg gggtcaagga acctcagtca ccgtctcctc a              351

<210> SEQ ID NO 32
<211> LENGTH: 118
<212> TYPE: PRT
<213> ORGANISM: Homo Sapien

<400> SEQUENCE: 32

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Ser Ala Tyr Ala Asp Asp Phe
    50                  55                  60

Lys Gly Arg Phe Ala Phe Ser Leu Glu Thr Ser Ala Ser Thr Ala Thr
65                  70                  75                  80

Tyr Leu Gln Ile Asn Asn Leu Lys Asn Glu Asp Thr Ala Thr Tyr Phe
                85                  90                  95

Cys Ala Thr Gly Gly Tyr Tyr Gly Met Asp Tyr Trp Gly Gln Gly Thr
            100                 105                 110

```
Ser Val Thr Val Ser Ser
        115

<210> SEQ ID NO 33
<211> LENGTH: 5
<212> TYPE: PRT
<213> ORGANISM: Homo Sapien

<400> SEQUENCE: 33

Asn Tyr Gly Met Asn
1               5

<210> SEQ ID NO 34
<211> LENGTH: 17
<212> TYPE: PRT
<213> ORGANISM: Homo Sapien

<400> SEQUENCE: 34

Trp Ile Asn Thr Tyr Thr Gly Glu Ser Ala Tyr Ala Asp Asp Phe Lys
1               5                   10                  15

Gly

<210> SEQ ID NO 35
<211> LENGTH: 8
<212> TYPE: PRT
<213> ORGANISM: Homo Sapien

<400> SEQUENCE: 35

Gly Gly Tyr Tyr Gly Met Asp Tyr
1               5

<210> SEQ ID NO 36
<211> LENGTH: 320
<212> TYPE: DNA
<213> ORGANISM: Homo Sapien

<400> SEQUENCE: 36
gacattgtga tgactcagtc tccagccacc ctgtctgtga ctccaggaga tagagtctct    60
ctttcctgca gggccagcca gagtattagc gactacttac actggtatca acaaaaatca   120
catgagtctc caaggcttct catcaaatat gcttcccaat ccatctctgg gatcccctcc   180
aggttcagtg gcagtggatc agggtcagat ttcactctag tatcaacagt gtggaacctg   240
aagatgttgg agtgtattac tgtcaaaatg gtcacagctt ccgctcacg ttcggtgctg    300 ggaccaagct ggagctgaaa                                               320

<210> SEQ ID NO 37
<211> LENGTH: 107
<212> TYPE: PRT
<213> ORGANISM: Homo Sapien

<400> SEQUENCE: 37

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
```

```
                65                  70                  75                  80
Glu Asp Val Gly Val Tyr Tyr Cys Gln Asn Gly His Ser Phe Pro Leu
                    85                  90                  95
Thr Phe Gly Ala Gly Thr Lys Leu Glu Leu Lys
            100                 105
```

<210> SEQ ID NO 38
<211> LENGTH: 11
<212> TYPE: PRT
<213> ORGANISM: Homo Sapien

<400> SEQUENCE: 38

```
Arg Ala Ser Gln Ser Ile Ser Asp Tyr Leu His
1               5                   10
```

<210> SEQ ID NO 39
<211> LENGTH: 7
<212> TYPE: PRT
<213> ORGANISM: Homo Sapien

<400> SEQUENCE: 39

```
Tyr Ala Ser Gln Ser Ile Ser
1               5
```

<210> SEQ ID NO 40
<211> LENGTH: 9
<212> TYPE: PRT
<213> ORGANISM: Homo Sapien

<400> SEQUENCE: 40

```
Gln Asn Gly His Ser Phe Pro Leu Thr
1               5
```

<210> SEQ ID NO 41
<211> LENGTH: 351
<212> TYPE: DNA
<213> ORGANISM: Homo Sapien

<400> SEQUENCE: 41

```
cagatccagt tggtgcagtc tggacctgag ctgaagaagc ctggagagac agtcaagatc      60
tcctgcaagg cttctggtt taccttcaca aactatggaa tgaactgggt gaagcaggct     120
ccaggaaagg gtttaaagtg gatgggctgg ataaacacct acactggaga gccaacatat    180
gctgatgact tcaagggacg gtttgccttc tctttggaaa cctctgccag cactgcctat    240
ttgcagatca caaccctcaa aaatgaggac acggctacat atttctgtgc aacgggggt     300
tactatggta tggactactg gggtcaagga acctcagtca ccgtctcctc a             351
```

<210> SEQ ID NO 42
<211> LENGTH: 117
<212> TYPE: PRT
<213> ORGANISM: Homo Sapien

<400> SEQUENCE: 42

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Phe Thr Phe Thr Asn Tyr
                20                  25                  30
Gly Met Asn Trp Val Lys Gln Ala Pro Gly Lys Gly Leu Lys Trp Met
            35                  40                  45
Gly Trp Ile Asn Thr Tyr Thr Gly Glu Pro Thr Tyr Ala Asp Asp Phe
```

```
                        50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Thr Gly Gly Tyr Tyr Gly Met Asp Tyr Trp Gly Gln Gly Thr Ser
            100                 105                 110

Val Thr Val Ser Ser
            115
```

<210> SEQ ID NO 43
<211> LENGTH: 5
<212> TYPE: PRT
<213> ORGANISM: Homo Sapien

<400> SEQUENCE: 43

```
Asn Tyr Gly Met Asn
1               5
```

<210> SEQ ID NO 44
<211> LENGTH: 17
<212> TYPE: PRT
<213> ORGANISM: Homo Sapien

<400> SEQUENCE: 44

```
Trp Ile Asn Thr Tyr Thr Gly Glu Pro Thr Tyr Ala Asp Asp Phe Lys
1               5                  10                  15

Gly
```

<210> SEQ ID NO 45
<211> LENGTH: 8
<212> TYPE: PRT
<213> ORGANISM: Homo Sapien

<400> SEQUENCE: 45

```
Gly Gly Tyr Tyr Gly Met Asp Tyr
1               5
```

<210> SEQ ID NO 46
<211> LENGTH: 321
<212> TYPE: DNA
<213> ORGANISM: Homo Sapien

<400> SEQUENCE: 46

```
gacattgtga tgactcagtc tccagccacc ctgtctgtga ctccaggaga tagagtctct      60
ctttcctgca gggccagcca gagtattagc gactacttac actggtatca acaaaaatca     120
catgagtctc caaggcttct catcaaatat gcttcccaat ccatctctgg gatcccctcc     180
aggttcagtg gcagtggatc agggtcagat ttcactctca gtatcaacag tgtggaacct     240
gaagacgttg gagtgtatta ctgtcaaaat ggtcacagct ttccgctcac gttcggtgct     300
gggaccaagc tggaggtgaa a                                               321
```

<210> SEQ ID NO 47
<211> LENGTH: 107
<212> TYPE: PRT
<213> ORGANISM: Homo Sapien

<400> SEQUENCE: 47

```
Asp Ile Val Met Thr Gln Ser Pro Ala Thr Leu Ser Val Thr Pro Gly
1               5                  10                  15
```

```
Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Val Lys
            100                 105

<210> SEQ ID NO 48
<211> LENGTH: 11
<212> TYPE: PRT
<213> ORGANISM: Homo Sapien

<400> SEQUENCE: 48

Arg Ala Ser Gln Ser Ile Ser Asp Tyr Leu His
1               5                   10

<210> SEQ ID NO 49
<211> LENGTH: 7
<212> TYPE: PRT
<213> ORGANISM: Homo Sapien

<400> SEQUENCE: 49

Tyr Ala Ser Gln Ser Ile Ser
1               5

<210> SEQ ID NO 50
<211> LENGTH: 9
<212> TYPE: PRT
<213> ORGANISM: Homo Sapien

<400> SEQUENCE: 50

Gln Asn Gly His Ser Phe Pro Leu Thr
1               5
```